United States Patent
Pentikis et al.

(10) Patent No.: US 12,280,037 B2
(45) Date of Patent: *Apr. 22, 2025

(54) METHOD AND PHARMACEUTICAL COMPOSITION FOR TREATING OR PREVENTING TRICHOMONIASIS AND USES THEREOF

(71) Applicant: EVOFEM BIOSCIENCES, INC., San Diego, CA (US)

(72) Inventors: Helen S. Pentikis, Baltimore, MD (US); David Palling, Philadelphia, PA (US); Carol J. Braun, Baltimore, MD (US); Richard Holl, Rolla, MO (US); Gregory Kaufman, Short Hills, NJ (US)

(73) Assignee: EVOFEM BIOSCIENCES, INC., San Diego, CA (US)

( * ) Notice: Subject to any disclaimer, the term of this patent is extended or adjusted under 35 U.S.C. 154(b) by 445 days.

This patent is subject to a terminal disclaimer.

(21) Appl. No.: 17/028,838

(22) Filed: Sep. 22, 2020

(65) Prior Publication Data
US 2022/0087978 A1    Mar. 24, 2022

(51) Int. Cl.
| | |
|---|---|
| *A61K 31/4164* | (2006.01) |
| *A61K 9/00* | (2006.01) |
| *A61K 9/16* | (2006.01) |
| *A61K 31/566* | (2006.01) |
| *A61K 31/567* | (2006.01) |
| *A61K 31/69* | (2006.01) |
| *A61K 31/702* | (2006.01) |
| *A61P 33/02* | (2006.01) |

(52) U.S. Cl.
CPC ........ *A61K 31/4164* (2013.01); *A61K 9/0056* (2013.01); *A61K 9/16* (2013.01); *A61K 31/566* (2013.01); *A61K 31/567* (2013.01); *A61K 31/69* (2013.01); *A61K 31/702* (2013.01); *A61P 33/02* (2018.01)

(58) Field of Classification Search
None
See application file for complete search history.

(56) References Cited

U.S. PATENT DOCUMENTS

| | | |
|---|---|---|
| 3,376,311 A | 4/1968 | Butler |
| 4,803,066 A | 2/1989 | Edwards |
| 4,920,141 A | 4/1990 | Horstmann et al. |
| 4,925,950 A | 5/1990 | Massonneau et al. |
| 4,925,951 A | 5/1990 | Massonneau et al. |
| 4,925,952 A | 5/1990 | Massonneau et al. |
| 4,957,918 A | 9/1990 | Martin et al. |
| 5,023,361 A | 6/1991 | Massonneau et al. |
| 5,026,694 A | 6/1991 | Skov et al. |
| 5,140,055 A | 8/1992 | Hirata et al. |
| 5,329,003 A | 7/1994 | Bruchmann |
| 5,549,911 A | 8/1996 | Leduc et al. |
| 5,574,167 A | 11/1996 | Jaber |
| 5,614,545 A | 3/1997 | Martin et al. |
| 5,904,937 A | 5/1999 | Augello et al. |
| 6,103,262 A | 8/2000 | Desai et al. |
| 6,214,386 B1 | 4/2001 | Santus et al. |
| 6,653,333 B2 | 11/2003 | Yotsuya et al. |
| 6,794,372 B2 | 9/2004 | Del Soldato et al. |
| 6,794,411 B1 | 9/2004 | Lebon et al. |
| 7,485,729 B2 | 2/2009 | Hsieh et al. |
| 7,691,831 B2 | 4/2010 | Bonner, Jr. et al. |
| 7,700,076 B2 | 4/2010 | Tamarkin et al. |
| 7,820,145 B2 | 10/2010 | Tamarkin et al. |
| 7,884,090 B2 | 2/2011 | Bonner, Jr. et al. |
| 7,893,097 B2 | 2/2011 | Yang et al. |
| 8,088,846 B2 | 1/2012 | Hsieh et al. |
| 8,158,152 B2 | 4/2012 | Palepu |

(Continued)

FOREIGN PATENT DOCUMENTS

| | | |
|---|---|---|
| AU | 1995/15803 B2 | 8/1995 |
| CN | 1546020 A | 11/2004 |

(Continued)

OTHER PUBLICATIONS

Ghosh, Arindam P., Cheri Aycock, and Jane R. Schwebke. "In vitro study of the susceptibility of clinical isolates of Trichomonas vaginalis to metronidazole and secnidazole." Antimicrobial Agents and Chemotherapy 62.4 (2018): e02329-17. (Year: 2018).*

Nyirjesy, Paul, et al. "Difficult-to-treat trichomoniasis: results with paromomycin cream." Clinical infectious diseases 26.4 (1998): 986-988. (Year: 1998).*

Aug. 3, 2020 Decision of Rejection issued by the Japanese Patent Office in connection with Japanese Patent Application No. 2018-228992 [English translation included].

(Continued)

*Primary Examiner* — Bethany P Barham
*Assistant Examiner* — Peter Anthopolos
(74) *Attorney, Agent, or Firm* — PROCOPIO, CORY, HARGREAVES & SAVITCH LLP

(57) ABSTRACT

Method of treating or preventing trichomoniasis or *T. vaginalis* infection in a subject in need thereof, the method involving administering to the subject a therapeutically effective amount of secnidazole or a pharmaceutically acceptable salt in a microgranule formulation, wherein the microgranule formulation comprises a plurality of microgranules. The subject can also have bacterial vaginosis, is HIV-positive, and/or is suffering with metronidazole-resistant trichomoniasis and/or tinidazole-resistant trichomoniasis. The subject can also be a sexual partner of a person with trichomoniasis. The microgranule formulation can also be administered with paromomycin, tinidazole, metronidazole, boric acid or a combination thereof. Pharmaceutical compositions and uses for treating or preventing trichomoniasis or *T. vaginalis* infection in a subject in need thereof are also contemplated herein.

29 Claims, 8 Drawing Sheets

(56) References Cited

U.S. PATENT DOCUMENTS

| | | | |
|---|---|---|---|
| 8,309,103 | B2 | 11/2012 | Hernandez-Ramirez et al. |
| 8,318,132 | B2 | 11/2012 | Kolb et al. |
| 8,642,660 | B2 | 2/2014 | Goldfarb |
| 8,658,678 | B2 | 2/2014 | Yang et al. |
| 8,772,242 | B2 | 7/2014 | Borody |
| 8,853,247 | B2 | 10/2014 | Ren et al. |
| 8,877,792 | B2 | 11/2014 | Yang et al. |
| 8,912,113 | B2 | 12/2014 | Ravichandran et al. |
| 8,946,276 | B2 | 2/2015 | Nordsiek et al. |
| 8,999,360 | B2 | 4/2015 | Borody et al. |
| 9,006,316 | B2 | 4/2015 | Hsieh et al. |
| 9,016,221 | B2 | 4/2015 | Brennan et al. |
| 10,335,390 | B2 | 7/2019 | Pentikis et al. |
| 10,682,338 | B2 | 6/2020 | Pentikis et al. |
| 10,849,884 | B2 | 12/2020 | Pentikis et al. |
| 10,857,133 | B2 | 12/2020 | Pentikis et al. |
| 2003/0017210 | A1 | 1/2003 | Debregeas et al. |
| 2003/0091540 | A1 | 5/2003 | Ahmad et al. |
| 2003/0092754 | A1 | 5/2003 | Nishimuta et al. |
| 2004/0033968 | A1 | 2/2004 | Lin et al. |
| 2005/0026982 | A1 | 2/2005 | Johannsen et al. |
| 2005/0043408 | A1 | 2/2005 | Yeboah et al. |
| 2005/0069566 | A1 | 3/2005 | Tamarkin et al. |
| 2005/0165077 | A1 | 7/2005 | Hernandez-Ramirez et al. |
| 2005/0186142 | A1 | 8/2005 | Tamarkin et al. |
| 2005/0222169 | A1 | 10/2005 | Ahmad et al. |
| 2005/0261298 | A1 | 11/2005 | Solow-Cordero et al. |
| 2005/0262647 | A1 | 12/2005 | Hoeffkes et al. |
| 2006/0024243 | A1 | 2/2006 | Arkin et al. |
| 2006/0137684 | A1 | 6/2006 | Evans et al. |
| 2006/0140984 | A1 | 6/2006 | Tamarkin et al. |
| 2006/0140990 | A1 | 6/2006 | Bortz et al. |
| 2006/0142304 | A1 | 6/2006 | Southall et al. |
| 2006/0269485 | A1 | 11/2006 | Friedman et al. |
| 2007/0015841 | A1 | 1/2007 | Tawa et al. |
| 2007/0154516 | A1 | 7/2007 | Bortz et al. |
| 2007/0255064 | A1 | 11/2007 | Szarvas et al. |
| 2007/0287714 | A1 | 12/2007 | Ahmad et al. |
| 2007/0292355 | A1 | 12/2007 | Tamarkin et al. |
| 2008/0139664 | A1 | 6/2008 | Yeboah et al. |
| 2008/0171709 | A1 | 7/2008 | Remmal |
| 2008/0171768 | A1 | 7/2008 | Remmal |
| 2009/0131342 | A1 | 5/2009 | Ellis |
| 2010/0159035 | A1 | 6/2010 | Shemer |
| 2010/0304998 | A1 | 12/2010 | Sem |
| 2011/0002866 | A1 | 1/2011 | Lubit et al. |
| 2011/0046378 | A1 | 2/2011 | Kolb et al. |
| 2011/0053941 | A1 | 3/2011 | Mautino et al. |
| 2011/0207702 | A1 | 8/2011 | Jacobs et al. |
| 2012/0219500 | A1 | 8/2012 | Sakurai et al. |
| 2012/0295839 | A1 | 11/2012 | Paull et al. |
| 2013/0309219 | A1 | 11/2013 | Ratner et al. |
| 2014/0065230 | A1 | 3/2014 | Shah et al. |
| 2014/0080778 | A1 | 3/2014 | Defrance |
| 2014/0271923 | A1 | 9/2014 | Reid |
| 2014/0378520 | A1 | 12/2014 | Ren et al. |
| 2015/0196536 | A1 | 7/2015 | Yang et al. |
| 2016/0067218 | A1* | 3/2016 | Pentikis .................. A61P 43/00 548/330.1 |
| 2016/0346252 | A1 | 12/2016 | Palling et al. |
| 2020/0038372 | A1 | 2/2020 | Pentikis et al. |
| 2020/0206192 | A1 | 7/2020 | Pentikis et al. |
| 2020/0289470 | A1 | 9/2020 | Pentikis et al. |
| 2020/0306228 | A1 | 10/2020 | Pentikis et al. |

FOREIGN PATENT DOCUMENTS

| | | |
|---|---|---|
| CN | 1789250 A | 6/2006 |
| CN | 1973838 A | 6/2007 |
| CN | 101255175 A | 9/2008 |
| CN | 102266284 A | 12/2011 |
| CN | 102335433 A | 2/2012 |
| EP | 0216453 A2 | 7/1986 |
| EP | 0206625 A2 | 12/1986 |
| EP | 0293090 A2 | 4/1988 |
| EP | 0348808 A2 | 1/1990 |
| EP | 0406665 A1 | 6/1990 |
| EP | 0378137 A2 | 7/1990 |
| EP | 0413533 A1 | 2/1991 |
| EP | 0717992 A2 | 6/1996 |
| GB | 2033232 A | 10/1978 |
| GB | 2103927 A | 3/1983 |
| JP | H9-507499 | 7/1997 |
| WO | WO 85/03000 A | 7/1985 |
| WO | WO 87/06129 A1 | 10/1987 |
| WO | WO 91/17744 | 11/1991 |
| WO | WO 93/12771 A | 7/1993 |
| WO | WO 96/35436 A | 11/1996 |
| WO | WO 97/05168 | 2/1997 |
| WO | WO 2000/059468 A1 | 10/2000 |
| WO | WO 2012/075015 A2 | 6/2012 |
| WO | WO 2014/121298 A2 | 8/2014 |
| WO | WO 2016/037131 A1 | 3/2016 |
| WO | WO 2016/196653 A1 | 12/2016 |

OTHER PUBLICATIONS

Takashi, I., et al., "Estimation of Crystallite Size by Powder X-ray Diffractometry," The Journal of Society of Power Technology in Japan, (2003) 40:177-184.
Shekunov, B.Y., et al., "Particle Size Analysis in Pharmaceutics: Principles, Methods, and Applications," Pharmaceutical Research, (Feb. 2007), 24(2):203-227.
Anderson, B. L., "Effect of Trichomoniasis Therapy on Genital HIV Viral Burden Among African Women," Sexually Transmitted Diseases, (2012) 39(8):638-642.
Kissinger, P., et al., "Single-dose versus 7-day-dose metronidazole for the treatment of trichomoniasis in women: an open-label, randomised controlled trial," Lancet Infectious Diseases, (2018) 18:1251-1250.
Menezes, C.B., et al., "Trichomoniasis—are we giving the deserved attention to the most common non-viral sexually transmitted disease worldwide?" Microbial Cell, (2016) 3(9) 404-418.
Sutton, M., et al., "The Prevalence of Trichomonas vaginalis Infection among Reproductive-Age Women in the United States, 2001-2004." Clinical Infectious Diseases, (2007) 45:1319-1326.
"Sexually Transmitted Diseases Treatment Guidelines, 2015," CDC Morbidity and Mortality Weekly Report, (2015) 64(3):1-137.
"Vaginitis in Nonpregnant Patients," Obstetrics & Gynecology, (2020) 135(1):1-17.
Alessio, C., et al., "Management of Resistant Trichomoniasis," Current Infectious Reports (2019), 21(31):1-7.
Bartley, J.B., et al., "Personal Digital Assistants Used to Document Compliance of Bacterial Vaginosis Treatment," Sexually Transmitted Diseases (2004), 31(8):488-491.
Pentikis, H.S., et al., "In vitro metabolic profile and drug-drug interaction assessment of secnidazole, a high-dose 5-nitroimidazole antibiotic for the treatment of vacterial vaginosis," Pharmacol. Res. Perspect. (2020), 8(4):e00634, https://doi.org/10.1002/prp2.634.
Wei, M.J., et al., "Bioequivalent study of secnidazole in healthy volunteers," Chinese Journal of Infection and Chemotherapy (2006), 6(3):159-162.
Zhu, D.Q., et al., "Evaluation of the Bioequivalence and Pharmacokinetics of Two Formulations of Secnidazole after Single Oral Administration in Healthy Volunteers," Arzneimittel-Forschung (Drug Research) (2007) 57(11):723-726.
Sobel, J.D., "Mixed vaginitis—more than coinfection and with therapeutic implications," Current Infectious Diseases Report, (2013), 15(2):104-108.
Dubreuil et al., "Le secnidazole: activité antibactérienne sur les anaérobies stricts," Antibiotiques (2005), 7:239-246 [English Abstract].
Hangargekar et al., "Formulation and Evaluation of Guar Gum Based Colon Targeted Tablets of Secnidazole and its β-Cyclodextrin Complex to Treat Amoebiasis," International Journal of Pharmacy and Pharmaceutical Sciences (2011), 3(4):294-298.
Malholtra, "Ciprofloxacin-tinidazol combination, fluconazole-azithromycin-secnidazole-kit and Doxycycline-Metronidazole Combination Therapy in Syndromic Management of Pelvic Inflamma-

(56) References Cited

OTHER PUBLICATIONS tory Disease: A Prospective Randomized Controlled Trial," Indian Journal of Medicinal Sciences (Dec. 1, 2003), 57 (12):549-555.
Narayana et al., "Formulation and In Vitro Evaluation of In Situ Gels Containing Secnidazole for Vaginitis," Yakugaku Zasshi (2009), 129(5):569-574.
Rao et al., "In Vitro Susceptibility Testing of Nonsporing Anaerobes to Ten Antimicrobial Agents," Indian J. Pathol. Microbial, (2000), 43(1):139-142.
Australian Patent Application No. 15803/95, filed Jan. 12, 1995, which is a national stage entry of PCT/FR1995/00039.
Baichwal et al., "Microencapsulation of Metronidazole," Indian J. Pharma. Sciences, (1980), 42(2):48-51.
Aug. 27, 2018 Decision of Rejection in connection with Japanese Patent Application No. 2017-512757 [English translation included].
Amsel, Richard, et al. "Nonspecific Vaginitis. Diagnostic Criteria and Microbial and Epidemiologic Associations," Am. J. Med., 74 (1): 14-22 (1983).
Dec. 27, 2018 Notice of Final Rejection in connection with Korean Patent Application No. 2017-7009154 [English translation included].
Miller, et al., "HIV, the Clustering of Sexually Transmitted Infections, and Sex Risk Among African American Women Who Use Drugs," Sexually Transmitted Diseases (2008), 35(7):696-702.
Kissinger, et al., "Trichomonas Vaginalis Treatment Reduces Vaginal HIV-1 Shedding," Sexually Transmitted Diseases (2009), 36(1):11-16.
Sutcliffe, et al., "Prevalence and Correlates of Trichomonas vaginalis Infection Among Female US Federal Prison Inmates," Sexually Transmitted Diseases (2010), 37(9):585-590.
Sosman, et al., "Sexually Transmitted Infections and Hepatitis in Men With a History of Incarceration," Sexually Transmitted Diseases (2011), 38(7):634-639.
Satterwhite, et al., "Sexually Transmitted Infections Among US Women and Men: Prevalence and Incidence Estimates, 2008," Sexually Transmitted Diseases (2013), 40(3):187-193.
Meites, et al., "Trichomonas vaginalis in Selected US Sexually Transmitted Disease Clinics: Testing, Screening, and Prevalence," Sexually Transmitted Diseases (2013), 40(11):865-869.
Kissinger, et al., "A Randomized Treatment Trial: Single Versus 7-Day Dose of Metronidazole for The Treatment of Trichomonas Vaginalis Among HIV-Infected Women," Journal of Acquired Immune Defficiency Syndrome (2010), 55(5):565-571.
Crosby, et al., "Condom effectiveness against non-viral sexually transmitted infections: a prospective study using electronic daily diaries," Sexually Transmitted Infections (2012), 88:484-489.
Peterman, et al., "High Incidence of New Sexually Transmitted Infections in the Year following a Sexually Transmitted Infection: A Case for Rescreening," Annals of Internal Medicine (2006), 145:564-572.
McClelland, et al., "Infection with Trichomonas vaginalis Increases the Risk of HIV-1 Acquisition," Journal of Infectious Diseases (2007), 195:698-702.
Van Der Pol, et al., "Trichomonas vaginalis Infection and HumanImmunodeficiency Virus Acquisition in African Women," Journal of Infectious Diseases (2008), 197:548-554.
"Incidence, Prevalence, and Cost of Sexually Transmitted Infections in the United States," CDC Fact Sheet, National Center for HIV/AIDS, Viral Hepatitis, STD, and TB Prevention, (Feb. 2013), pp. 1-4.
Ginocchio, et al., "Prevalence of Trichomonas vaginalis and Coinfection with Chlamydia trachomatis and Neisseria gonorrhoeae in the United States as Determined by the Aptima Trichomonas vaginalis Nucleic Acid Amplification Assay," Journal of Clinical Microbiology (2012), 50(8):2601-2608.
Rossignol, et al., "Nitroimidazoles in the treatment of trichomoniasis, giardiasis, and amebiasis," International Journal of Clinical Pharmacology, Therapy, and Toxicology (1984), 22(2):63-72.
Cudmore, et al., "Treatment of Infections Caused by Metronidazole-Resistant Trichomonas vaginalis," Clinical Microbiology Reviews (2004), 17(4):783-793.

Sena, et al., "Trichomonas vaginalis Infection in Male Sexual Partners: Implications for Diagnosis, Treatment, and Prevention," Clinical Infectious Diseases (2007), 44:13-22.
Moodley, et al., "Trichomonas vaginalis Is Associated with Pelvic Inflammatory Disease in Women Infected with Human Immunodeficiency Virus," Clinical Infectious Diseases (2002), 34:519-522.
"2015 Sexually Transmitted Diseases Treatment Guidelines—Trichomoniasis," Centers for Disease Control and Prevention, pp. 1-5.
Minkoff, et al., "Risk factors for prematurity and premature rupture of membranes: A prospective study of the vaginal flora In pregnancy," American Journal of Obstetrics and Gynecology (1984), 150(8):965-972.
Sosman, et al., "Screening for sexually transmitted diseases and hepatitis in 18-29-year-old men recently released from prison: feasibility and acceptability," International Journal of Sexually Transmitted Diseases & AIDS (2005), 1:117-122.
Videau et al., "Secnidazole: A 5-nitroimidazole derivative with a long half-life," British Journal of Veneral Diseases (1978), 54:77-80.
Jun. 1, 2020 Decision of Appeal issued by the Korean Intellectually Property Office in connection with Korean Patent Application No. 2017-7009154. [Incl. English translation].
Schwebke et al., "Intravaginal Metronidazole/Miconazole for the Treatment of Vaginal Trichomoniasis," Sexually Transmitted Diseases (2013), 40(9):710-714.
Austin et al., "Metronidazole in a single dose for the treatment of trichomoniasis," British Journal of Veneral Diseases (1982), 58:121-123.
Patel et al., "Prevalence and Correlates of Trichomonas vaginalis Infection Among Men and Women in the United States," Clinical Infectious Diseases (2018), 67:211-217.
Ozbilgin et al., "Trichomoniasis in Non-Gonococcic Urethritis Among Male Patients," Journal of the Egyptian Society of Parasitology (1994), 24(3):621-625.
Siboulet, et al., "Urogenital Trichomoniasis. Trials with a Long Half-Life Imidazole: Secnidazole," Médecine et Maladies Infectieuses, (1977) 7-9:400-409.
Cotch, et al., "Trichomonis vaginalis Associated With Low Birth Weight and Preterm Delivery," Sexually Transmitted Diseases (1997), 24(6):353-360.
Shuter, et al., "Rates of and Risk Factors of Trichomoniasis Among Pregnant Inmates in New York City," Secually Transmitted Diseases (1998), 25(6):303-307.
Cu-Uvin, et al., "Prevalence, Incidence, and Persistence or Recurrence of Trichomoniasis among Human Immunodeficiency Virus (HIV)-Positive Women and among HIV-Negative Women at High Risk for HIV Infection," (2002), 34:1406-1411.
International Search Report and Written Opinion for PCT/US2016/035299 dated Aug. 22, 2016.
Bohbot et al., "Treatment of Bacterial Vaginosis: A Multicenter, Double-Blind, Double-Dummy, Randomised Phase III Study.," Hindawi Pub. Corp., Infectious Diseas. (2010), 1-6.
Nunez et al., "Low-dose secnidazole in the treatment of bacterial vaginosis," International Journal of Gynecology and Obstetrics (2005), 88:281-285.
Menard, John-Pierre, "Antibacterial treatment of bacterial vaginosis: current and emerging therapies," International Journal of Women's Health (2011), 3:295-305.
International Search Report and Written Opinion for PCT/US2015/048681 dated Jan. 19, 2016.
International Search Report for PCT/FR95/00039 dated Jun. 14, 1995.
Gillis, et al., "Secnidazole—A review of its Antimicrobial Activity, Pharmacokinetic Properties and Therapeutic Use in the Management of Protozoal Infections and Bacterial Vaginosis," Drugs (1996), 51(4):621-638.
Rinshou to Kenkyu (2003), 80(5):45. [No English version available].
Acar et al., "Le secnidazole, un nouveau 5-nitro imidazole," Antibiotiques (2005), 7:177-182 [English Abstract].

(56) References Cited

OTHER PUBLICATIONS

De Backer et al., "In vitro activity of secnidazole against Atopoblum vaginae, an anaerobic pathogen involved in bacterial vaginosis," Clin. Microbiol. Infect. (Jun. 22, 2009), 16:470-472.

* cited by examiner

METHOD AND PHARMACEUTICAL COMPOSITION FOR TREATING OR PREVENTING TRICHOMONIASIS AND USES THEREOF

INCORPORATION BY REFERENCE

All U.S. patents, U.S. patent application publications, foreign patents, foreign and PCT published applications, articles and other documents, references and publications noted herein, and all those listed as References Cited in any patent or patents that issue herefrom, are hereby incorporated by reference in their entirety. The information incorporated is as much a part of this application as if all the text and other content was repeated in this application, and will be treated as part of the text and content of this application as filed.

The following patents and applications and the contents therein are hereby incorporated by reference in their entirety: U.S. Ser. No. 62/046,731, filed Sep. 5, 2014; 62/101,636, filed Jan. 9, 2015; 62/169,369, filed Jun. 1, 2015; Ser. No. 14/846,505, filed Sep. 4, 2015 (now U.S. Pat. No. 10,335,390); Ser. No. 16/049,032, filed Jul. 30, 2018 (now U.S. Pat. No. 10,682,338, issued Jun. 16, 2020); Ser. No. 15/170,572, filed Jun. 1, 2016; Ser. No. 16/403,176, filed May 3, 2019; Ser. No. 16/586,372, filed Sep. 27, 2019; Ser. No. 16/586,339, filed Sep. 27, 2019; Ser. No. 16/817, 246, filed Mar. 12, 2020; Ser. No. 16/890,526, filed Jun. 2, 2020; and Ser. No. 16/901,739, filed Jun. 15, 2020; PCT International Application Nos. PCT/US15/48681, filed Sep. 4, 2015, and PCT/US16/35299, filed Jun. 1, 2016.

FIELD OF THE INVENTION

This invention relates to method and pharmaceutical composition for treating or preventing trichomoniasis or *Trichomonas vaginalis* (*T. vaginalis*) infection in a subject and uses thereof.

BACKGROUND OF THE INVENTION

The following includes information that may be useful in understanding the invention. It is not an admission that any of the information, publications or documents specifically or implicitly referenced herein is prior art, or essential, to the presently described or claimed invention.

Trichomoniasis is a sexually transmitted disease caused by the parasite, *T. vaginalis*, and the most common non-viral sexually transmitted infection ("STI") in the world. The World Health Organization estimates an incidence of trichomoniasis of 276 million new cases each year and prevalence of 187 million of infected individuals. (Menezes, et al., "Trichomoniasis—are we giving the deserved attention to the most common non-viral sexually transmitted disease worldwide?", *Microb. Cell,* 3(9):404-419 (2016) ("Menezes")). In the United States, trichomoniasis affects an estimated 3.7 million persons. (Satterwhite, et al. "Sexually transmitted infections among US women and men; prevalence and incidence estimates," *Sex. Transm. Dis.,* 40:187- 93 (2013)). Health disparities persist in the epidemiology of *T. vaginalis* infection in the United States—*T. vaginalis* infection prevalence was 4.2% among black males, 8.9% among black females, and 0.03% and 0.8%, respectively, among males and females of other races/ethnicities, and infection is more common in women than in men (Patel, et al., "Prevalence and Correlates of Trichomoniasis *vaginalis* Infection Among Men and Women in the United States," *Clinical Infectious Diseases,* 67(2):211-7 (2018)). Also, *T. vaginalis* infection affects>11% of women aged≥40 years, and older women are more likely than younger women to be infected (Ginocchio, et al., "Prevalence of *Trichomonas vaginalis* and Coinfection with *Chlamydia trachomatis* and *Neisseria gonorrhoeae* in the United States as Determined by the Aptima *Trichomonas vaginalis* Nucleic Acid Amplification Assay," *J. Clinical Microbiology,* 50(8):2601-2608 (2012)). *T. vaginalis* infection is also commonly detected in sexually transmitted diseases ("STDs") clinic patients (Meites, et al. "*Trichomonas vaginalis* in selected U.S. sexually transmitted disease clinics: testing, screening, and prevalence," *Sex. Transm. Dis.,* 40:865-9 (2013) (26% of symptomatic women and 6.5% asymptomatic women tested). Additionally, high prevalence of trichomoniasis is detected among incarcerated persons—approximately 9% to 32% of incarcerated women, and approximately 2% to 9% of incarcerated men. (Sutcliffe, et al., "Prevalence and correlates of *Trichomonas vaginalis* infection among female US federal prison inmates," *Sex. Transm. Dis.,* 37:585-90 (2010); Sosman, et al., "Project START Biologics Study Group. Sexually transmitted infections and hepatitis in men with a history of incarceration," *Sex Transm Dis,* 38:634-9 (2011); Shuter, et al. "Rates of and risk factors for trichomoniasis among pregnant inmates in New York City," *Sex. Trasnm. Dis.,* 25:303-7 (1998); Sosman, et al., "Screening for sexually transmitted diseases and hepatitis in 18-29-year old men recently released from prison: feasibility and acceptability," *Int'l J. STD and AIDS,* 16:117-22 (2005)).

Men infected with trichomoniasis can experience symptoms of urethritis, epididymitis, or prostatitis, and women infected with trichomoniasis can experience discomfort with urination; itching, burning, redness or soreness of the genitals; or a change in their vaginal discharge, which may be diffuse, malodorous, and/or yellow-green with or without vulvar irritation. However, most people who are infected with trichomoniasis (approximately 70% to 85%) are asymptomatic or have minimal symptoms, and, as a result, are unaware of the infection and do not seek treatment. Untreated infections may last for months or years, and sexual partners may readily pass their infection through sexual intercourse. (Peterman, et al., "High incidence of new sexually transmitted infections in the year following a sexually transmitted infection: a case for rescreening," *Ann. Intern. Med.,* 145:564-72 (2006); Sutton, et al., "The prevalence of *Trichomonas vaginalis* infection among reproductive-age women in the United States, 2001-2004" *Clin. Infect. Dis.,* 45:1319-26 (2007); Sena, et al., "*Trichomonas vaginalis* infection in male sexual partners; implications for diagnosis, treatment, and prevention," *Clin. Infect Dis.,* 44:13-22 (2007)).

While it is understood that the best way to prevent transmission of trichomoniasis or *T. vaginalis* infection is through abstinence or, if sexually active, proper condom or dam use, successful application of these practices require consistency and dedication, which may be difficult to achieve. (Crosby, et al., "Condom effectiveness against non-viral sexually transmitted infections: a prospective study using electronic daily diaries," *Sex. Transm. Infect.,* 88:484-9 (2012)). Access to condom or dams is also required to help reduce the transmission of trichomoniasis, but not everyone and not every place has such access.

Screening procedures and diagnostic testing for *T. vaginalis* in a subject (such as human—male or female) presently exist, and routine screening of asymptomatic women with HIV infection for *T. vaginalis* is recommended because of the adverse events associated with asymptomatic trichomoniasis and Human Immunodeficiency Virus ("HIV") infection. See, e.g., Centers for Disease Control and Prevention's ("CDC's") 2015 Sexually Transmitted Disease Treatment Guidelines, 2015—https://www.cdc.gov/std/tg2015/default.htm; ("CDC's 2015 STD Treatment Guidelines") CDC's 2015 Sexually Transmitted Disease Treatment Guidelines—Trichomoniasis—https://www.cdc.gov/std/tg2015/trichomoniasis.htm; ("CDC 2015 Guidelines—Trichomoniasis"); ACOG Practice Bulletin—Vaginitis in Nonpregnant Patients, *Obstetrics & Gynecology*, 135(1):e1-e17 (Jan. 2020) ("2020 ACOG Practice Bulletin"). As recommended by the CDC, diagnostic testing for *T. vaginalis* should be performed in women seeking care for vaginal discharge, and screening may be considered for persons receiving care in high-prevalence settings (e.g., STD clinics and correctional facilities) and for asymptomatic persons at high risk for infection (e.g., persons with multiple sex partners, exchanging for payment, illicit drug use, or a history of STD). See CDC 2015 Guidelines—Trichomoniasis." Screening for *T. vaginalis* should be performed in women seeking care for vaginal discharge. See id. Also, because of the high rate of reinfection among women treated for trichomoniasis, retesting for *T. vaginalis* is recommended for all sexually active women within 3 months following initial treatment, regardless of whether they believe their sex partners were treated. See id. Testing by nucleic acid amplification testing ("NAAT"), which is the preferred diagnostic test for *T. vaginalis* infection, can be conducted as soon as 2 weeks after treatment. See id. & 2020 ACOG Practice Bulletin, p.e5-e7. Alternative diagnostic options include FDA-approved commercial tests (such as DNA hybridization probe tests (such as BD Affirm™ VPIII Microbial Identification System from Becton Dickinson in Sparks, MD), multiplex PCR panel tests (such as BD MAX™ CT/GC/TV Assay using the BD MAX™ System from Becton Dickinson in Sparks, MD) & antigen-detection testing (such as OSOM® *Trichomonas* Rapid Test from Sekisui Diagnostics in Framingham, MA)) or vaginal culture. See id.

Trichomoniasis or *T. vaginalis* infection is associated with serious health consequences, such as preterm birth, adverse pregnancy outcomes, infertility, HIV acquisition and cancer. (Menezes; McClelland, et al. "Infection with *Trichomonas vaginalis* increases the risk of HIV-1 acquisition," *J. Infect. Dis.*, 195:698-702 (2007); Van Der Pol, et al., "*Trichomonas vaginalis* infection and human immunodeficiency virus acquisition in African women," *J. Infect. Dis.*, 197:548-54 (2008) (Trichomoniasis associated with two- to threefold increased risk for HIV acquisition)). Among women with HIV infection, *T. vaginalis* infection in HIV-infected women also have increased risk for pelvic inflammatory disease ("PID") (Minkoff, et al., "Risk factors for prematurity and premature rupture of membranes: a prospective study of the vaginal flora in pregnancy," *Am. J. Obstet. Gynecol.*, 150:965-72 (1984); Cotch, et al., "*Trichomonas vaginalis* associated with low birth weight and preterm delivery," Sex. Transm. Dis., 24:353-60 (1997); Moodley, et al., "*Trichomonas vaginalis* is associated with pelvic inflammatory disease in women infected with human immunodeficiency virus," *Clin. Infect. Dis.*, 34:519-22 (2002) ("Moodley")).

As stated in the CDC 2015 Guidelines—Trichomoniasis, nitroimidazoles are the only class of antimicrobial medications known to be effective against *T. vaginalis* infections, and from this class, metronidazole and tinidazole have been cleared by the U.S. Food & Drug Administration ("FDA") for the oral or parenteral treatment of trichomoniasis. The CDC 2015 Guidelines—Trichomoniasis recommends the following treatment regimen for trichomoniasis: metronidazole (2 grams orally in a single dose) or tinidazole (2 grams orally in a single dose) or, as an alternative regimen, metronidazole (500 mg orally twice a day for 7 days). The CDC 2015 Guidelines—Trichomoniasis additionally states that tinidazole is generally more expensive, reaches higher levels in serum and the genitourinary tract, has a longer half-life than metronidazole (12.5 hours versus 7.3 hours), and has fewer gastrointestinal side effects. Also, the CDC 2015 Guidelines—Trichomoniasis states in randomized clinical trials, recommended metronidazole regimens have resulted in cure rates of approximately 84%-98%, and the recommended tinidazole regimen has resulted in cure rates of approximately 92%-100%. Further, the CDC 2015 Guidelines—Trichomoniasis states randomized controlled trials comparing single 2 g doses of metronidazole and tinidazole suggest that tinidazole is equivalent or superior to metronidazole in achieving parasitological cure and resolution of symptoms.

Furthermore, subjects with trichomoniasis or *T. vaginalis* infection may have one or more additional diseases or medical complications, such as HIV and/or bacterial vaginosis, and such subjects experience persistent or recurrent trichomoniasis or *T. vaginalis* infection. As stated in the CDC 2015 Guidelines—Trichomoniasis, up to 53% of women with HIV infection also are infected with *T. vaginalis* infection, and *T. vaginalis* infection in these women is tightly correlated with PID. (Cu-Uvin, et al., "Prevalence, incidence, and persistence or recurrence of trichomoniasis among human immunodeficiency virus (HIV)-positive women and among HIV-negative women at high risk for HIV infection," *Clin. Infect. Dis.* 34:1406-11 (2002); Miller, et al., "HIV, the clustering of sexually transmitted infections, and sex risk among African American women who use drugs," *Sex. Transm. Dis.* 35:696-702 (2008); Moodley). Also, treatment of trichomoniasis is connected to significant reductions in genital-tract HIV viral load and viral shedding. (Anderson, et al., "Effect of trichomoniasis therapy on genital HIV viral burden among African women," *Sex. Transm. Dis.*, 39:638-42 (2012); Kissinger, et al., "*Trichomonas vaginalis* treatment reduces vaginal HIV-1 shedding," *Sex. Transm. Dis.*, 36:11-6 (2009)). Typical treatment for these subjects is the CDC's alternative regimen of metronidazole 500 mg orally, twice a day for 7 days, rather than the CDC's recommended single dose treatments, which are shown to be less effective with these subjects. (Kissinger, et al., "A randomized treatment trial: single versus 7-day dose of metronidazole for the treatment of *Trichomonas vaginalis* among HIV-infected women," *J. Acquir. Immune Defic. Syndr.*, 55:565-71 (2010)).

The CDC warns that are factors that decrease the effectiveness of the recommended single dose treatments for trichomoniasis in these subjects, including impaired immunity, increased resistance to metronidazole and/or tinidazole, changes in vaginal ecology, use of antiretroviral therapy and increased rates of asymptomatic bacterial vaginosis co-infections. (CDC 2015 Guidelines—Trichomoniasis). For example, there is increasing evidence showing single-dose treatment of metronidazole may be insufficient to treat trichomoniasis. A prior meta-analysis of six published studies found that women who received 7 day-dose metronidazole had 46% fewer treatment failures compared to women who received single-dose and test of cure ("TOC") positive rates after single-dose metronidazole ranged from 6.2% to 18.0%. Kissinger et al., A randomized trial of metronidazole in a single 2 g dose versus 500 mg twice daily for 7 days for the treatment of trichomoniasis in women," *Lancet Infect.*

*Dis.*, 18(11):1251-1259 (2018). Further, a 2018 comparison study between single-dose 2-gram metronidazole treatment vs 7-day dose metronidazole treatment (500 mg twice daily for 7 days) showed that single-dose 2-gram metronidazole treatment in HIV-uninfected, non-pregnant women with trichomoniasis resulted in 45% increase in treatment failures than the 7-day dose metronidazole treatment. Id. As a result, there is a growing urgency to change the metronidazole treatment recommendations from single-dose to at least a 7-day dose regimen.

When a subject is infected with metronidazole-resistant *Trichomonas*, tinidazole is typically used as a second-line therapy for such subject. However, tinidazole is about ten times more expensive than metronidazole, and hence presenting a financial barrier for those who are in need of a metronidazole alternative to treat their trichomoniasis or *T. vaginalis* infection. Alesso, et al., "Management of Resistant Trichomoniasis," *Curr. Infect. Dis. Rep*, 21(9):31 (2019) Also, there is a growing number of subjects infected with tinidazole-resistant trichomoniasis, who are in need of alternative therapies. Presently, high-level metronidazole and tinidazole-resistant trichomoniasis is treated with a high dose oral and vaginal tinidazole (e.g., 500 mg taken orally, twice a day+500 mg taken vaginally twice a day for 14 days; or 1 gram taken orally, three times a day+500 mg taken vaginally, three times a day for 14 days; or 400 mg taken orally, three times a day for 10 days; or 500 mg taken orally, three times a day for at least 10 days;) or a combination of high-dose oral tinidazole (1 gram, three times a day) and intravaginal paromomycin cream (6.25%, 5 grams vaginally nightly) for 14 days. Id. However, high doses of tinidazole can be expensive and create increased adverse effects, such as GI intolerance and nausea. High doses of paromomycin can bring vaginal ulcerations and pain. Id. In addition, these alternative therapies have a high rate of patient non-compliance since they involve long treatment periods with multiple dosing per day.

Therefore, in light of the above, there is still a need for alternative methods for treating or preventing trichomoniasis or *T. vaginalis* infection in a subject in need thereof, which have improved efficacy, safety profiles, manufacturing, patient compliance, patient tolerability (such as fewer side effects and/or increased palatability) and/or cost, and can be a single dose treatment.

SUMMARY OF THE INVENTION

The invention described and claimed herein has many attributes and embodiments including, but not limited to, those set forth or described or referenced in this Summary of the Invention. It is not intended to be all-inclusive and the invention described and claimed herein is not limited to or by the features or embodiments identified in this introduction, which is intended for purposes of illustration only and not restriction.

Embodiments described herein are directed to a method of treating or preventing trichomoniasis or *T. vaginalis* infection in a subject in need thereof, the method comprising administering to the subject a therapeutically effective amount of secnidazole or a pharmaceutically acceptable salt thereof in a microgranule formulation. In some embodiments, the secnidazole or the pharmaceutically acceptable salt thereof in the microgranule formulation is administered orally. In some embodiments, the secnidazole or the pharmaceutically acceptable salt thereof in the microgranule formulation comprises a plurality of microgranules. In some embodiments, each microgranule comprises an inactive core (such as a sugar core, microcrystalline cellulose core or any core that does not contain any active pharmaceutical ingredient ("API")) and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, wherein the therapeutically effective amount of secnidazole is an amount of secnidazole that exhibits a maximum plasma concentration ($C_{max}$) of secnidazole in the subject of about 17.4 μg/ml and about 26.5 μg/ml, or about 34.5 μg/ml to about 58.3 μg/ml, or about 26 μg/ml to about 34 μg/ml, or about 26 μg/ml to about 58 μg/ml. In some embodiments, wherein the therapeutically effective amount of secnidazole is an amount of secnidazole that exhibits a time to maximum plasma concentration ($T_{max}$) of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a time to drug elimination half-life ($t_{1/2}$) of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semi-solid, or soft food. In some embodiments, the food substance may include, but not limited to, applesauce, yogurt, pudding or the like. In some embodiments, integration of the secnidazole microgranule formulation into a food substance has a taste masking function.

In another embodiment, a method of treating or preventing trichomoniasis or *T. vaginalis* infection in a subject in need thereof, the method comprising administering to the subject a microgranule formulation comprising a therapeutically effective amount of secnidazole, wherein the microgranule formulation comprises a plurality of microgranules having a volume-weighted particle size distribution within a microgranule population, wherein the volume-weighted particle size distribution as measured by mean diameter from a representative sample of the microgranule population comprises (a) at least 10% of the microgranule population having a volume-weighted particle size equal to or larger than about 470 micrometers, and/or (b) 50% of the microgranule population having a volume-weighted particle size in a range of from about 640 micrometers to about 810 micrometers; and/or (c) 90% of the microgranule population having a volume-weighted particle size smaller than about 1170 micrometers. In some embodiments, the mean diameter is measured by laser diffraction. In some embodiments, wherein each microgranule comprises a sugar core or a microcrystalline cellulose core, and a layer outside of the sugar core or the microcrystalline cellulose core, the layer comprising secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, wherein the therapeutically effective amount of secnidazole is an amount of secnidazole that exhibits a $C_{max}$ of secnidazole in the subject of about 17.4 µg/ml and about 26.5 µg/ml, or about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

Embodiments described herein are directed to a method of treating or preventing trichomoniasis or *T. vaginalis* infection in a subject in need thereof, the method comprising administering to the subject a microgranule formulation comprising a therapeutically effective amount of nitroimidazole compound or a pharmaceutically acceptable salt thereof, wherein the microgranule formulation comprises a plurality of microgranules, wherein each microgranule comprises a core and a coating, wherein the core comprises the nitroimidazole compound or the pharmaceutically acceptable salt thereof, and wherein the coating surrounds the core. In some embodiments, the nitroimidazole compound is secnidazole, metronidazole, tinidazole, nimorazole, dimetridazole, 6-Amino PA824, orinidazole, megazol, azanidazole, benznidazole, pimonidazole or a combination thereof. In some embodiments, the nitroimidazole compound is secnidazole. In some embodiments, the nitroimidazole compound is in the core. In some embodiments, the nitroimidazole compound comprises at least 70% of the core by weight. In some embodiments, the coating covers partially or all of the exterior surface of the core. In some embodiments, the coating does not contain a nitroimidazole compound. In some embodiments, the nitroimidazole compound comprises at least about 70% of the core by weight; at least about 75% of the core by weight; at least about 80% of the core by weight; at least about 85% of the core by weight; at least about 90% of the core by weight; or about at least about 95% of the core by weight. In some embodiments, the nitroimidazole compound comprises about 70% of the core by weight; about 75% of the core by weight; about 80% of the core by weight; about 85% of the core by weight; about 90% of the core by weight; or about 95% of the core by weight. In some embodiments, the plurality of microgranules comprise about 1 gram to about 4 grams of the nitroimidazole compound. In some embodiments, the plurality of microgranules comprises a therapeutically effective amount of nitroimidazole compound. In some embodiments, the core further comprises at least one polymer. In some embodiments, the polymer can be, but not limited to, Avicel®, Methocel®, hydroxyl propyl cellulose, acacia, guar gum, povidone, lactose monohydrate, or a combination thereof. In some embodiments, the core further comprises Avicel®, Methocel® or a combination thereof. In some embodiments, the core further comprises cellulose microcrystalline (such as the product cellulose microcrystalline sold under the trademark Avicel® PH-101), methyl cellulose (such as the product methyl cellulose sold under the trademark Methocel® AV15LV) or a combination thereof. In some embodiments, the polymer comprises about 30% of the core by weight. In some embodiments, the ratio of the nitroimidazole compound to the at least one polymer in the core may be about 70:30, or lesser than about 70:30, or more than greater than 70:30. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function. In some embodiments, the core comprises an active ingredient and at least one polymer. In some embodiments, the active ingredient is secnidazole or other nitroimidazole compounds described herein.

In some embodiments, the core further comprises one or more dispersion agent or binding agent. In some embodiments, the dispersion agent or binding agent includes, but not limited to, microcrystalline cellulose, methylcellulose, hydroxyl propyl cellulose, acacia, guar gum, povidone, lactose monohydrate, or a combination thereof.

In some embodiments, the core further comprises one or more microlubricant or anti-tacking agent. In some embodiments, the microlubricant or anti-tacking agent includes, but not limited to, sodium stearate, magnesium stearate, stearic acid, talc or a combination thereof. In some embodiments, the core further comprises a binder (such as, but not limited to, starch).

In some embodiments, the coating may be modified to modulate drug absorption of the drug by varying the composition of the coating, the percentage weight of the composition, or any combination thereof.

In some embodiments, the coating comprises a polymer. In some embodiment, the polymer includes, but not limited to, polyvinylpyrrolidone, ethylcellulose, the product 2-Methylprop-2-enoic acid-N—N-dimethylmethanamine (2/1) sold under the trademark Eudragit® RL, the product anionic copolymers of methacrylic acid and methyl methacrylate at a ratio of approximately 1:1 sold under the trademark Eudragit® L, the product amino methacrylate copolymer sold under the trademark Eudragit® E, the product anionic copolymers of methacrylic acid and methyl methacrylate at a ratio of approximately 1:2 sold under the trademark Eudragit® S, cellulose acetate, polyvinyl alcohol, shellac, methacrylic acid copolymers, cellulose acetate phthalate, hydroxypropylmethylcellulose phthalate, hydroxypropylmethylcellulose acetate succinate, cellulose acetate trimellitate and polyvinyl acetate phthalate. In some embodiments, the polymer can be, but not limited to, Eudagrit®, ethyl cellulose, Methocel®, glyceryl behenate, or a combination thereof. In some embodiments, the polymer is the product ethyl acrylate-methyl methacrylate copolymer sold under the trademark Eudagrit® NE30D. In some embodiments, the polymer is the product ethyl acrylate-methyl methacrylate copolymer sold under the trademark Eudagrit® NE30D comprises about 5.795% of the composition of weight.

In some embodiments, the coating further comprises a polyether polymer. In some embodiments, the polyether polymer can be, but limited to, polyethylene glycol ("PEG"), acetyl tributyl citrate, triethyl citrate, dibutyl phthalate, dibutyl sebacate, gelatin, propylene glycol, triacetin or a combination thereof. In some embodiments, the polyether polymer is PEG. In some embodiments, the PEG is PEG 4000. In some embodiments, the coating comprises about 10% to about 13% of the composition by weight. In some embodiments, the coating comprises about 13% or less than about 13% of the composition by weight. In some embodiments, the coating comprises about 10% or more than 10% of the composition by weight. In some embodiments, the PEG (such as PEG 4000) comprises about 1.75% of the composition by weight. In some embodiments, the PEG (such as PEG 4000) comprises about 1.75% of an individual microgranule by weight.

In some embodiments, other auxiliary coating aids such as a minor amount (about 1 to about 5% by weight based on the active core component and the total weight of the final coating) of a plasticizer such as, but not limited to, acetyltributyl citrate, triacetin, acetylated monoglyceride, grape seed oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethyl citrate, tributyl citrate, glyceroltributyrate, polyethyleneglycol, propylene glycol or a combination thereof with or without an antisticking agent (such as, but limited to, a silicate such as, but not limited to, talc). In some embodiments, the coating further comprises talc.

In some embodiments, the pharmaceutical composition further comprises talc. In some embodiments, the plurality of microgranules further comprises talc. In some embodiments, the talc is a blending agent.

In some embodiments, the core comprises a spheronized microgranule. In some embodiments, the microgranules may be formed by wet granulation followed by extrusion and spheronization. In some embodiments, the core further comprises a binder. In some embodiments, the binder may be starch.

It is also known in the art that the active ingredients may be contained in such compositions with pharmaceutically acceptable diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, G. S. Banker & C. T. Rhodes, 4$^{th}$ Edition, CRC Press (2002); *Goodman & Gilman's The Pharmaceutical Basis of Therapeutics*, L. L. Brunton, R. Hilal-Dandan & B. C. Knollmann, 13th Edition, McGraw-Hill Education (2018); *Remington's Pharmaceutical Sciences* by E. W. Martin; and *Remington: The Science and Practice of Pharmacy*, Loyd V. Allen (Ed.), 22$^{nd}$ Edition, Pharmaceutical Press (2013) can be consulted.

In some embodiments, the therapeutically effective amount of secnidazole in the microgranule formulation is 1 gram or 2 grams. In some embodiments, the therapeutically effective amount of secnidazole in the microgranule formulation is 2 grams, 4 grams or 6 grams. In some embodiments, the therapeutically effective amount of secnidazole is 2 grams.

In some embodiments, the plurality of microgranules comprising a daily dose amount of a nitroimidazole compound (such as secnidazole). In some embodiments, the plurality of microgranules comprising a daily dose amount of a nitroimidazole compound may be configured as a single unit dose or multiple unit doses. In some embodiments, the multiple unit doses can be two, three or four unit doses per day. In some embodiments, the unit dose may be a portion of the daily dose amount of the nitroimidazole compound. In some embodiments, the nitroimidazole compound is secnidazole and the daily dose amount is about 1 gram, about 2 grams, about 3 grams, about 4 grams, about 5 grams or about 6 grams. In some embodiments, the daily dose amount can be configured as one, two, three, four or more unit doses per day. For example, the plurality of microgranules comprising about 2 grams of secnidazole may be configured as 2 unit doses, each unit dose comprising about 1 gram of secnidazole, or about 4 grams of secnidazole configured as 2 unit doses, each unit dose comprising about 2 grams of secnidazole, or about 6 grams of secnidazole configured as 3 unit doses, each unit dose comprising about 2 grams of secnidazole. Likewise, the plurality of microgranules comprising about 2 grams of secnidazole may be configured as 4 unit doses, each until dose comprising about 0.5 grams of secnidazole. In some embodiments, the unit doses in a multiple unit dose regime may have unit doses of equal or different amounts of secnidazole. For example, the plurality of microgranules comprising about 2 grams of secnidazole may be configured as 3 unit doses, where one unit dose comprises about 1 gram of secnidazole and the other two unit doses each comprises about 0.5 grams of secnidazole. Administration of such multiple unit doses to the subject can done during different times in the day (for example, every 6 hours, 8 hours, or 12 hours) or at the same time.

The microgranule formulations described herein may be prepared, packaged, or sold in bulk, as a single unit dose or as multiple unit doses and may be administered in orally.

In some embodiments, therapeutically effective amounts, daily doses, or single unit doses of the secnidazole (or other nitroimidazole composition) microgranule formulations described herein may be administered once per day or multiple times per day, such as twice per day; 3 times per day; 4 times per day; 5 times per day; or more than 5 times per day. In some embodiments, the treatment or use period can be 1 day, 2 days, 3 days, 4 days, 5 days, 6, days, 7 days, 8 days, 9 days, 10 days, 11 days, 12, days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days. In some embodiments, the dosing schedule of the invention can be about 1 gram, about 2 grams, about 3 grams, or about 4 grams of secnidazole (or other nitroimidazole composition) per day for 1 day, 2 days, 3 days, 4 days, 5 days, 6, days, 7 days, 8 days, 9 days, 10 days, 11 days, 12, days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days. In some embodiments, the dosing can be done with 1 day, 2 days, 3 days, 4 days or more than 4 days apart each dose. For example, the dosing schedule of the invention can be about 2 grams of secnidazole (or other nitroimidazole composition) per day, taken about 3 days or about 4 days apart×2. As another example, the dosing schedule of the invention can be about 2 grams to 4 grams of secnidazole per day for 1 day to 14 days. The invention herein contemplates all of the dosage schedule combinations set forth in this application.

Embodiments are also directed to a dosage regimen for administering a therapeutically effective amount of a nitroimidazole compound (such as secnidazole) for the methods and uses described herein. For example, in some embodiments, the methods and uses described herein can comprises a dosage regimen that includes a plurality of daily doses having an equal amount of the nitroimidazole compound as the initial dose in one or more unit doses. In other embodiments, the dosage regimen can include an initial dose of the nitroimidazole compound in one or more unit doses, then one or more subsequent daily doses having a lower amount of the nitroimidazole compound than the initial doses in one or more unit dose. The dosage regimen may administer one or more initial doses followed by one or more maintenance doses. The one or more doses following the administering of the one or more initial doses can be maintenance doses. Such maintenance doses can have a lower or higher amount of the nitroimidazole compound than the one or more initial doses.

Some embodiments are directed to a method of manufacturing a plurality of microgranules comprising a nitroimidazole compound, such as secnidazole. In some embodiments, the method of manufacturing a plurality of microgranules comprises forming a plurality of microgranule cores. In some embodiments, forming a plurality of microgranule cores comprises a wet granulation step. In some embodiments, the wet granulation step comprises mixing a nitroimidazole compound with one or more polymers to form a mixture, and hydrating the mixture to form a hydrated mixture. In some embodiments, hydrating the mixture comprises the addition of water to the mixture. In some embodiments, the wet granulation step is carried out in a planetary mixer or high shear granulator.

In some embodiments, forming a plurality of microgranules cores further comprises an extrusion step. In some embodiments, the hydrated mixture is passed through an extruder to form a plurality of extruded microgranule cores. In some embodiments, the hydrated mixture is passed through an extruder (such as a Niro Extruder) fitted with a 0.8 mm screen to form a plurality of extruded microgranule cores.

In some embodiments, forming a plurality of microgranule cores further comprises a spheronization step to form a plurality of spheronized microgranule cores. In some embodiments, the extruded microgranule cores are spheronized to form a plurality of spheronized microgranule cores. In some embodiments, the spheronization step is carried out using a spheronizer (such as a Niro Spheronizer).

In some embodiments, forming a plurality of microgranule cores further comprise drying and screening the plurality of spheronized microgranule cores, In some embodiments, the plurality of spheronized microgranule cores is dried using a Glatt fluid bed and screened to remove fine and oversize material to form a plurality of microgranule cores.

In some embodiments, the method of manufacturing a plurality of microgranules comprises coating the plurality of microgranule cores to form a plurality of coated microgranules. In some embodiments, coating the plurality of microgranule cores comprises coating the plurality of microgranule cores comprises coating the plurality of microgranule cores with one or more polymers. In some embodiments, the one or more polymers can be, but not limited to, PEG (such as PEG 4000), Eudragit® (such as the product ethyl acrylate-methyl methacrylate copolymer sold under the trademark Eudragit® NE30D), talc or a combination thereof, wherein the one or more polymers is sprayed on the plurality of microgranule cores using a Glatt fluid bed to form a plurality of coated microgranules.

In some embodiments, the method of manufacturing a plurality of microgranules further comprises drying and screening the plurality of coated microgranules. In some embodiments, the plurality of coated microgranules are dried in a Glatt fluid bed and screened to remove fine and oversize material.

In some embodiments, the method of manufacturing a plurality of microgranules further comprises blending and curing the plurality of coated microgranules. In some embodiments, blending and curing the plurality of coated microgranules comprises bending the plurality of coated microgranules with talc in a V-blender and curing in a tray dryer at 40° C. for 24 hours.

In some embodiments, administering a therapeutically effective amount of secnidazole to a subject comprises administering a secnidazole or a pharmaceutically acceptable salt thereof in a controlled release form to the subject. In some embodiments, the coating described herein can delay disintegration and absorption in the gastrointestinal tract and thereby providing a controlled and/or sustained action over a longer period than an immediate release composition. Additionally, such coatings can be adapted for release of a secnidazole in a predetermined pattern (e.g., in order to achieve a controlled release composition) or it can be adapted not to release the active compound until after passage of the stomach (enteric coating). Suitable coatings encompassed by such embodiments may include, but are not limited to, sugar coating, film coating (e.g., but not limited to, hydroxypropyl methylcellulose, methylcellulose, methyl hydroxyethyl cellulose, hydroxypropyl cellulose, carboxymethylcellulose, acrylate copolymers, polyethylene glycols, polyvinylpyrrolidone or a combination thereof), or an enteric coating (e.g., but not limited to, methacrylic acid copolymer, cellulose acetate phthalate, hydroxypropylmethylcellulose phthalate, hydroxypropyl methylcellulose acetate succinate, polyvinyl acetate phthalate, shellac, ethyl cellulose or a combination thereof). Furthermore, a time delay material such as, but not limited to, glyceryl monostearate or glyceryl distearate can be incorporated into the coatings of some embodiments. In still other embodiments, the coating can be adapted to protect the composition from unwanted chemical changes, for example, but not limited to, to reduce chemical degradation prior to the release of API.

In some embodiments, particle size of microgranules can be measured using various commonly available methods such as measurement using light (e.g., light-scattering or laser diffraction methods or turbidimetric methods), sedimentation methods (e.g., pipette analysis using an Andreassen pipette, sedimentation scales, photosedimentometers or sedimentation in a centrifugal force), pulse methods (e.g., Coulter counter), or sorting by means of gravitational or centrifugal force.

In some embodiments, pharmacokinetics ("PK") study performed by mainly the compartmental or non-compartmental analysis. Noncompartmental PK analysis is highly dependent on estimation of total drug exposure. Total drug exposure is most often estimated by area under the curve ("AUC") methods, with the trapezoidal rule (numerical integration) the most common method. Compartmental PK analysis uses kinetic models to describe and predict the concentration-time curve. Single compartment models wherein linear pharmacokinetics is so-called because the graph of the relationship between the various factors involved (dose, blood plasma concentrations, elimination, etc.) gives a straight line or an approximation to one. Multi-compartmental models wherein the graph for the non-linear relationship between the various factors is represented by a curve; the relationships between the factors can then be found by calculating the dimensions of different areas under the curve.

In some embodiments, the therapeutically effective amount of secnidazole in a microgranule formulation is administered as a single dose. In some embodiments, the therapeutically effective amount of secnidazole in a microgranule formulation administered as a single dose is the only dose required to be administered to the subject to achieve a post-treatment clinical outcome, resolution of one or more symptoms of trichomoniasis or *T. vaginalis* infection, or a combination thereof.

In some embodiments, microgranule formulation is packaged as a unit dose or a single unit dose. A unit dose, also defined as single dose herein, is a dosage in a form that includes therapeutically effective amount of secnidazole in a microgranule formulation. The unit dose could be administered to a subject as a single unit dose, wherein the therapeutically effective amount of secnidazole in a microgranule formulation is included in a single package, such as, one pouch, packet, sachet, or bottle. In some embodiments, the microgranule formulation is packaged in such a way as to provide a barrier to oxygen and moisture. In some embodiments, the microgranule formulation is packaged in a foil pouch or sachet. In some embodiments, the foil pouch or sachet is made of a polyester-faced laminated or polyethylene-metallocene-lined aluminum foil pouching material that provides a barrier to oxygen and moisture. In some embodiments, the pouch or sachet is made from a material such as, but not limited to, the product polyester-faced laminated pouching material sold under the trademark FASSON® RAPID-ROLL® White Cosmetic Web 350 HB. In some embodiments, the microgranule formulation can include a plurality of microgranules comprising inert cores made from microcrystalline cellulose. For example, the inert cores made from microcrystalline cellulose can replace sugar spheres/sugar cores. In some embodiments, glycerol monostearate (e.g., the product glycerol monostearate sold under the trademark PLASCRYL® T20 by Evonik) can be used as an anti-tacking agent. For example, glycerol monostearate can be used in Eudragit coatings in place of talc.

In some embodiments, the plurality of microgranules may be contained, or encased in a capsule (soft shell or hard shell capsule), a gel capsule or any other suitable encapsulation medium known in the art. In some embodiments, the plurality of microgranules may be configured as a powder for reconstitution as a suspension. In some embodiments, a plurality of microgranules corresponding to a therapeutically effective amount of the nitroimidazole compound (such as secnidazole) may be encased, or encapsulated in one or more sachets, capsules (soft shell or hard shell capsule), gel caps, or any other suitable encapsulation medium known in the art.

In some embodiments, the methods and uses described herein further comprises administering paromomycin, tinidazole, metronidazole, boric acid or a combination thereof to a subject who is resistant or allergic to metronidazole and/or tinidazole, or the subject who is infected metronidazole and/or tinidazole-resistant trichomoniasis with or when metronidazole and/or tinidazole is contraindicated. In some embodiments, the administration of paromomycin, tinidazole, metronidazole, boric acid or a combination thereof to the subject is on the same day or a different day relative to the administration of secnidazole to the subject. In some embodiments, the administration of the compounds of the combination therapy (e.g., secnidazole, paromomycin, tinidazole, metronidazole, boric acid or a combination thereof) are administered concomitantly or sequentially.

In some embodiments, the methods and uses described herein further comprises co-administering an additional compound selected from ethinyl estradiol (EE2), norethindrone (NET), or a combination thereof. In some embodiments, the additional compound is administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound selected from EE2, NET, or a combination thereof. In some embodiments, the subject has a resolution of one or more symptoms of trichomoniasis or *T. vaginalis* infection within up to about seven days after administration to the subject. In some embodiments, the subject has an alleviation of one or more symptoms of trichomoniasis or *T. vaginalis* infection within up to about three days after administration to the subject.

In some embodiments, the subject is a male or female; adult or child. In some embodiments, the subject is a healthy male or healthy female. In some embodiments, the subject is a pregnant female. In some embodiments, the subject is a healthy pregnant female. In some embodiments, the subject has confirmed or suspected trichomoniasis or *T. vaginalis* infection. In some embodiments, the subject is resistant to metronidazole and/or tinidazole. In some embodiments, the subject suffers from recurrent trichomoniasis or *T. vaginalis* infection, that is, the subject having had 2 or more trichomoniasis episodes or *T. vaginalis* infections in the past 12 months. In some embodiments, the subject is also HIV-positive, such as a HIV-positive male, a HIV-positive female or a HIV-positive pregnant female. In some embodiments, the subject is also infected (or co-infected) with bacterial vaginosis. In some embodiments, the subject is a female or pregnant female is HIV-positive and also infected (or co-infected) with bacterial vaginosis. In some embodiments, the subject is a child who is less than 18 years of age, or an adult who is at least 18 years old.

In some embodiments, the subject is a female or pregnant female also infected (or co-infected) with bacterial vaginosis, or has confirmed or suspected bacterial vaginosis. In some embodiments, the subject is a female having had 3 or fewer bacterial vaginosis infections/episodes in the past 12 months. In some embodiments, the subject is a female having had 4 or more bacterial vaginosis infections/episodes in the past 12 months. In some embodiments, the subject is a female presenting with thin, homogeneous vaginal discharge, a positive potassium hydroxide ("KOH") Whiff test, vaginal fluid pH greater than or equal to 4.7, and the presence of "clue cells" greater than 20% of total epithelial cells, or any combination thereof. In some embodiments, the female with bacterial vaginosis presents with the four Amsel criteria parameters and a gram stain slide Nugent score equal to, or higher than four on bacterial analysis of vaginal samples. In some embodiments, the four Amsel criteria parameters are abnormal vaginal discharge (e.g., thin, homogenous vaginal discharge), a positive KOH Whiff test, vaginal fluid pH greater than or equal to 4.7, and the presence of clue cells greater than 20% of total epithelial cells. (See Amsel et al., "Nonspecific vaginitis. Diagnostic criteria and microbial and epidemiologic associations," *Am. J. Med.*, 74(1):14-22 (1983))("Amsel").

Some embodiments further comprise determining a post-treatment clinical outcome. In some embodiments, a post-treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative *T. vaginalis* test, a negative KOH Whiff test, and clue cells less than 20% of total epithelial cells, post-treatment. In some embodiments, a clinical outcome responder is a subject with a gram stain slide Nugent score of less than four, post-treatment. In some embodiments, a clinical outcome responder is a subject with normal vaginal discharge, a negative *T. vaginalis* test, a negative KOH Whiff test, clue cells less than 20% of total epithelial cells), and a gram stain slide Nugent score of less than four, post-treatment. In some embodiments, administering to the subject a therapeutically effective amount of secnidazole in a microgranule formulation results in better than expected effectiveness than U.S. Food & Drug Administration-approved ("FDA-approved") drugs used in the treatment or prevention of trichomoniasis or *T. vaginalis* infection. In some embodiments, administering to the subject a therapeutically effective amount of secnidazole in a microgranule formulation results in superior effectiveness than FDA-approved drugs used in the treatment or prevention of trichomoniasis or *T. vaginalis* infection. In some embodiments, administering to the subject a therapeutically effective amount of secnidazole in a microgranule formulation results in a higher rate of clinical cure than FDA-approved drugs used in the treatment or prevention of trichomoniasis or *T. vaginalis* infection. In some embodiments, administering to the subject a therapeutically effective amount of secnidazole in a microgranule formulation results in a better than expected safety profile than FDA-approved drugs used in the treatment or prevention of trichomoniasis or *T. vaginalis* infection. In some embodiments, administering to the subject a therapeutically effective amount of secnidazole in a microgranule formulation results in a more favorable safety profile than FDA-approved drugs used in the treatment or prevention of trichomoniasis or *T. vaginalis* infection.

In some embodiments, wherein the therapeutically effective amount of secnidazole in the microgranule formulation administered as a single dose is the only dose required to be administered to the subject to achieve a post-treatment clinical outcome by resolution of one or more symptoms of trichomoniasis or *T. vaginalis* infection. By way of example, the one or more symptoms of trichomoniasis or *T. vaginalis* infection include, but not limited to:

For Men: Itching or irritation inside the penis; burning with urination or after ejaculation; and/or discharge from the penis.

For Women: Itching, burning, redness or soreness of the genitals; pain with urination; a change in vaginal discharge (i.e., thin discharge or increased volume) that is clear, white, gray, yellowish or greenish with an unusual fishy smell; and/or pain with sexual intercourse.

Other symptoms of trichomoniasis or *T. vaginalis* infection include, but not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof.

Embodiments herein are also directed to a microgranule formulation for treating or preventing trichomoniasis or *T. vaginalis* infection in a subject in need thereof comprising secnidazole or a pharmaceutically acceptable salt thereof. In some embodiments, the microgranule formulation comprises a therapeutically effective amount of secnidazole or a pharmaceutically acceptable salt thereof. In some embodiments, the secnidazole or the pharmaceutically acceptable salt thereof in the microgranule formulation comprises a plurality of microgranules. In some embodiments, each microgranule comprises an inactive core (such as a sugar core, microcrystalline cellulose core or any core that does not contain any API and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, wherein the therapeutically effective amount of secnidazole is an amount of secnidazole that exhibits a $C_{max}$ of secnidazole in the subject of about 17.4 µg/ml and about 26.5 µg/ml, or about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In another embodiment, a microgranule formulation for treating or preventing trichomoniasis or *T. vaginalis* infection in a subject in need thereof comprising a microgranule formulation comprising a therapeutically effective amount of secnidazole, wherein the microgranule formulation comprises a plurality of microgranules having a volume-weighted particle size distribution within a microgranule population, wherein the volume-weighted particle size distribution as measured by mean diameter from a representative sample of the microgranule population comprises (a) at least 10% of the microgranule population having a volume-weighted particle size equal to or larger than about 470 micrometers, and/or (b) 50% of the microgranule population having a volume-weighted particle size in a range of from about 640 micrometers to about 810 micrometers; and/or (c) 90% of the microgranule population having a volume-weighted particle size smaller than about 1170 micrometers. In some embodiments, the mean diameter is measured by laser diffraction. In some embodiments, wherein each microgranule comprises a sugar core or a microcrystalline cellulose core, and a layer outside of the sugar core or the microcrystalline cellulose core, the layer comprising secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, wherein the therapeutically effective amount of secnidazole is an amount of secnidazole that exhibits a $C_{max}$ of secnidazole in the subject of about 17.4 µg/ml and about 26.5 µg/ml, or about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In another embodiment, a microgranule formulation for treating or preventing trichomoniasis or *T. vaginalis* infection in a subject in need thereof, the microgranule formulation comprising a therapeutically effective amount of nitroimidazole compound or a pharmaceutically acceptable salt thereof, the microgranule formulation comprises a plurality of microgranules, wherein each microgranule comprises a core and a coating, wherein the core comprises the nitroimidazole compound or the pharmaceutically acceptable salt thereof, and wherein the coating surrounds the core. In some embodiments, the nitroimidazole compound is secnidazole, metronidazole, tinidazole, nimorazole, dimetridazole, 6-Amino PA824, orinidazole, megazol, azanidazole, benznidazole, pimonidazole or a combination thereof. In some embodiments, the nitroimidazole compound is secnidazole. In some embodiments, the nitroimidazole compound is in the core. In some embodiments, the nitroimidazole compound comprises at least 70% of the core by weight. In some embodiments, the coating covers partially or all of the exterior surface of the core. In some embodiments, the coating does not contain a nitroimidazole compound. In some embodiments, the nitroimidazole compound comprises at least about 70% of the core by weight; at least about 75% of the core by weight; at least about 80% of the core by weight; at least about 85% of the core by weight; at least about 90% of the core by weight; or about at least about 95% of the core by weight. In some embodiments, the nitroimidazole compound comprises about 70% of the core by weight; about 75% of the core by weight; about 80% of the core by weight; about 85% of the core by weight; about 90% of the core by weight; or about 95% of the core by weight. In some embodiments, the plurality of microgranules comprise about 1 gram to about 6 grams of the nitroimidazole compound. In some embodiments, the plurality of microgranules comprises a therapeutically effective amount of nitroimidazole compound. In some embodiments, the core further comprises at least one polymer. In some embodiments, the polymer can be, but not limited to, Avicel®, Methocel®, hydroxyl propyl cellulose, acacia, guar gum, povidone, lactose monohydrate, or a combination thereof. In some embodiments, the core further comprises Avicel®, Methocel® or a combination thereof. In some embodiments, the core further comprises cellulose microcrystalline (such as the product cellulose microcrystalline sold under the trademark Avicel® PH-101), methyl cellulose (such as the product methyl cellulose sold under the trademark Methocel® AV15LV) or a combination thereof. In some embodiments, the polymer comprises about 30% of the core by weight. In some embodiments, the ratio of the nitroimidazole compound to the at least one polymer in the core may be about 70:30, or lesser than about 70:30, or more than greater than 70:30. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function. In some embodiments, the core comprises an active ingredient and at least one polymer. In some embodiments, the active ingredient is secnidazole or other nitroimidazole compounds described herein.

In some embodiments, the microgranule formulation is a delayed release formulation and comprises a plurality of microgranules. In some embodiments, the delayed release formulation, when administered to a subject provides a secnidazole concentration profile characterized by a change in secnidazole concentration as a function of time that is less than that of an immediate release secnidazole microgranule formulation. In some embodiments, the delayed release formulation, when administered to a subject provides a secnidazole concentration profile characterized by a $T_{max}$ that is greater than that of an immediate release secnidazole microgranule formulation. In some embodiments, the delayed release formulation, when administered to a subject provides a secnidazole concentration profile characterized by a $C_{max}$ that is greater than that of an immediate release secnidazole microgranule formulation. In some embodiments, the delayed release formulation, when administered to a subject provides a secnidazole concentration profile characterized by an Area Under the Receiver Operating Characteristic Curve ("AUC") that is greater than that of an immediate release secnidazole microgranule formulation. In some embodiments, the microgranule formulation comprises about 1 gram to about 6 grams of secnidazole or a pharmaceutically acceptable salt thereof. In some embodiments, each microgranule comprises an inactive core (such as a sugar core, microcrystalline cellulose core or any core that does not contain any API and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, the microgranule formulation comprises about 1 gram, about 2 grams, about 3 grams, about 4 grams, about 5 grams, or about 6 grams of secnidazole or a pharmaceutically acceptable salt thereof. In some embodiments, the microgranule formulation is suitable for oral administration. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

Embodiments herein are also directed to a use of secnidazole or a pharmaceutically acceptable salt thereof in a microgranule formulation in the manufacture of a medicament for the treatment or prevention of trichomoniasis or *T. vaginalis* infection in a subject, wherein the microgranule formulation comprises a therapeutically effective amount of secnidazole or the pharmaceutically acceptable salt thereof in the microgranule formulation. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 34.5 µg/ml and about 58.3 µg/ml, or about 26 µg/ml to about 34 µg/ml, or about 26 µg/ml to about 58 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 17.4 µg/ml and about 26.5 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of about 3 hours to about 4 hours, or about 6 hours to about 24 hours, or about 2 hours to about 24 hours. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of 2 hours to 6 hours, or about 6 hours to about 24 hours, or about 2 hours to about 24 hours. In some embodiments, the plurality of microgranules each having a particle size diameter in the range of about 400 micrometers to about 841 micrometers.

In another embodiment, use of secnidazole or a pharmaceutically acceptable salt thereof in a microgranule formulation for the treatment or prevention of trichomoniasis or *T. vaginalis* infection in a subject, wherein the microgranule formulation comprises a therapeutically effective amount of secnidazole or the pharmaceutically acceptable salt thereof in the microgranule formulation. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 34.5 µg/ml and about 58.3 µg/ml, or about 26 µg/ml to about 34 µg/ml, or about 26 µg/ml to about 58 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 17.4 µg/ml and about 26.5 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of about 3 hours to about 4 hours, or about 6 hours to about 24 hours, or about 2 hours to about 24 hours. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of about 2 hours to about 6 hours, or about 6 hours to about 24 hours, or about 2 hours to about 24 hours. In some embodiments, the plurality of microgranules each having a particle size diameter in the range of about 400 micrometers to about 841 micrometers.

In another embodiment, use of a pharmaceutical composition comprising a plurality of microgranules for treating or preventing trichomoniasis or *T. vaginalis* infection in a subject, wherein the plurality of microgranules comprises a therapeutically effective amount of secnidazole or a pharmaceutically acceptable salt thereof, wherein each microgranule comprises a core and a coating, wherein the core comprises an active ingredient and at least one polymer, wherein the active ingredient is the secnidazole or the pharmaceutically acceptable salt thereof, wherein the secnidazole or the pharmaceutically acceptable salt thereof comprises at least 70% of the core by weight, wherein the coating is on the outside of the core, wherein the therapeutically effective amount of the secnidazole or the pharmaceutically acceptable salt thereof is about 1 gram, about 2 grams, about 3 grams, about 4 grams, about 5 grams or about 6 grams; and wherein the pharmaceutical composition is for oral administration.

In another embodiment, use of a pharmaceutical composition in preparation of a medicament comprising a plurality of microgranules for treating or preventing trichomoniasis or *T. vaginalis* infection in a subject, wherein the plurality of microgranules comprises a therapeutically effective amount of secnidazole or a pharmaceutically acceptable salt thereof, wherein each microgranule comprises a core and a coating, wherein the core comprises an active ingredient and at least one polymer, wherein the active ingredient is the secnidazole or the pharmaceutically acceptable salt thereof, wherein the secnidazole or the pharmaceutically acceptable salt thereof comprises at least 70% of the core by weight, wherein the coating is on the outside of the core, wherein the therapeutically effective amount of the secnidazole or the pharmaceutically acceptable salt thereof is about 1 gram, about 2 grams, about 3 grams, about 4 grams, about 5 grams, or about 6 grams; and wherein the pharmaceutical composition is for oral administration.

Embodiments herein are also directed to a method of making the secnidazole microgranule formulation, the method comprising coating one or more sugar spheres and/or microcrystalline cellulose spheres. In some embodiments, the process comprises (a) layering secnidazole on one or more sugar spheres and/or microcrystalline cellulose spheres; (b) layering a seal coating on top of the secnidazole on the one or more sugar spheres and/or microcrystalline cellulose spheres to produce end products of (b), wherein the seal coating comprises polyethylene glycol (such as polyethylene glycol 4000); (c) layering a top coating on top of the end products of (b) to product end products of (c), wherein the top coating comprises with ethyl acrylate-methyl methacrylate copolymer (such as the product ethyl acrylate-methyl methacrylate copolymer sold under the trademark Eudragit® NE30D); and (d) curing the end products of (c). In some embodiments, the process comprises (a) layering secnidazole on one or more sugar spheres and/or microcrystalline cellulose spheres; (b) layering a seal coating on top of the secnidazole on the one or more sugar spheres and/or microcrystalline cellulose spheres to produce end products of (b), wherein the seal coating comprises ethyl acrylate-methyl methacrylate copolymer (such as the product ethyl acrylate-methyl methacrylate copolymer sold under the trademark Eudragit® NE30D); and (c) curing the end products of (b). In some embodiments, coating with ethyl acrylate-methyl methacrylate copolymer (such as the product ethyl acrylate-methyl methacrylate copolymer sold under the trademark Eudragit® NE30D) provides a delayed release formulation. Other grades of the product ethyl acrylate-methyl methacrylate copolymer sold under the trademark Eudragit® can also be used in the formulations, e.g., Eudragit® E (either E 100 or E PO) or the product methyl methacrylate and diethylaminoethyl methacrylate copolymer dispersion sold under the trademark Kollicoat® SmartSeal. In some embodiments, a method of making the secnidazole microgranule formulation comprises blending with talc. In some embodiments, blending with talc increases the flowability of the secnidazole microgranule formulation.

BRIEF DESCRIPTION OF THE FIGURES

The accompanying drawings, which are incorporated herein and form a part of the specification, illustrate the aspects of the present disclosure and, together with the description, further serve to explain the principles of the aspects and to enable a person skilled in the pertinent art to make and use the aspects. The drawings are for illustration purposes only, show exemplary non-limiting embodiments, and are not necessarily drawn to scale.

and (2) EE2 was administered in conjunction with 2 gram microgranule formulation SYM-1219 on Day 1 of Period 2 (triangle markers).

Figure 3:
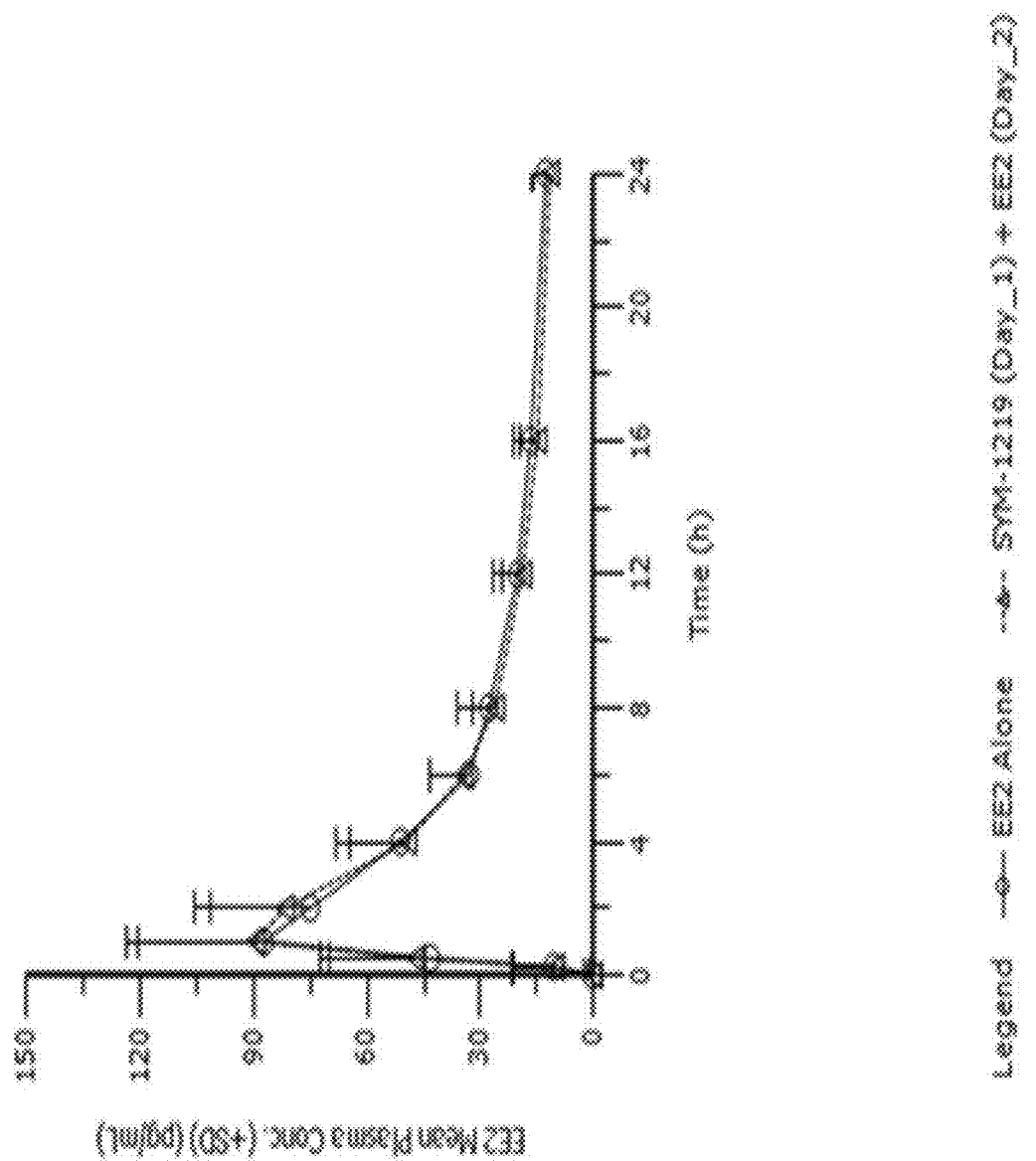

FIG. 3 illustrates the mean (±SD) EE2 plasma concentrations (pg/mL) for Group B2 over time where (1) EE2 was administered alone (circle markers) on Day 1 of Period 1; and (2) 2 gram microgranule formulation SYM-1219 was administered on Day 1 of Period 2 and EE2 was administered on Day 2 of Period 2 (triangle markers).

Figure 4:
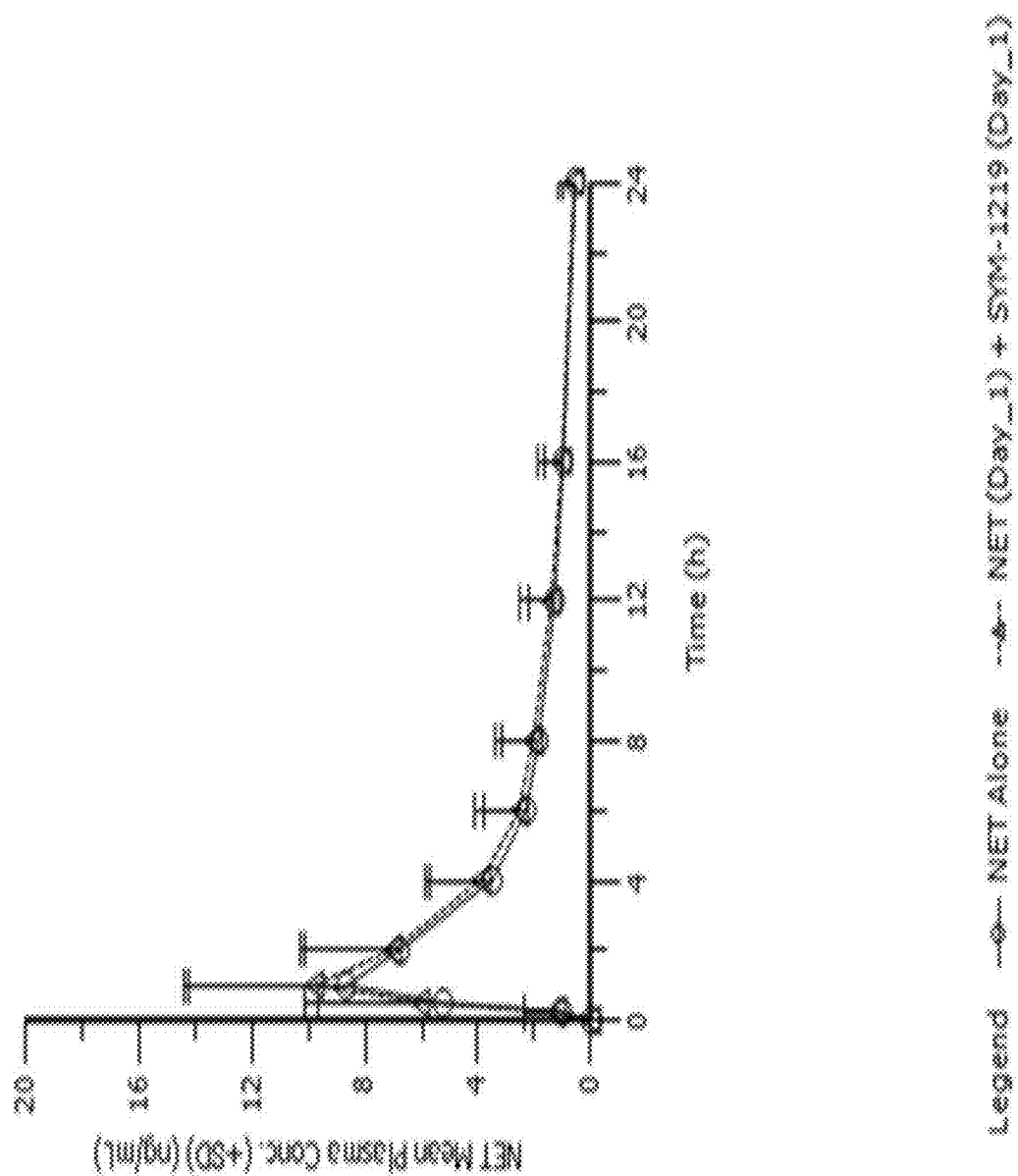

FIG. 4 illustrates the mean (±SD) NET plasma levels (ng/mL) for Group B1 over time where (1) NET alone was administered on Day 1 of Period 1 (circle markers), and (2) NET followed by 2 gram microgranule formulation of SYM-1219 was administered on Day 1 of Period 2 (triangle markers).

Figure 5:
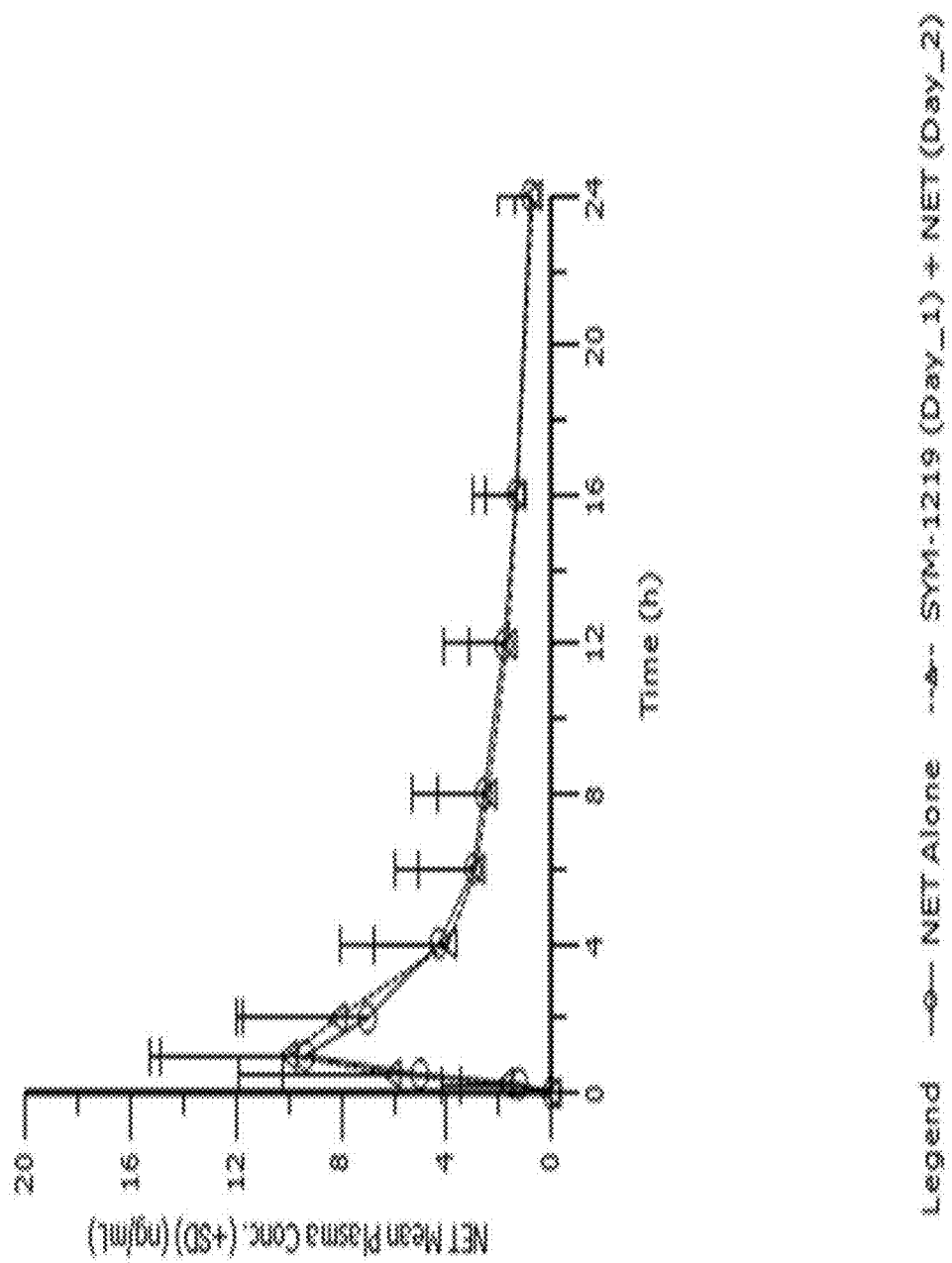

FIG. 5 illustrates the mean (±SD) NET plasma levels (ng/mL) for Group B2 over time where (1) NET alone was administered on Day 1 of Period 1 (circle markers), and (2) 2 gram microgranule formulation of SYM-1219 was administered on Day 1 of Period 2 and NET was administered on Day 2 of Period 2 (triangle markers).

Figure 6:
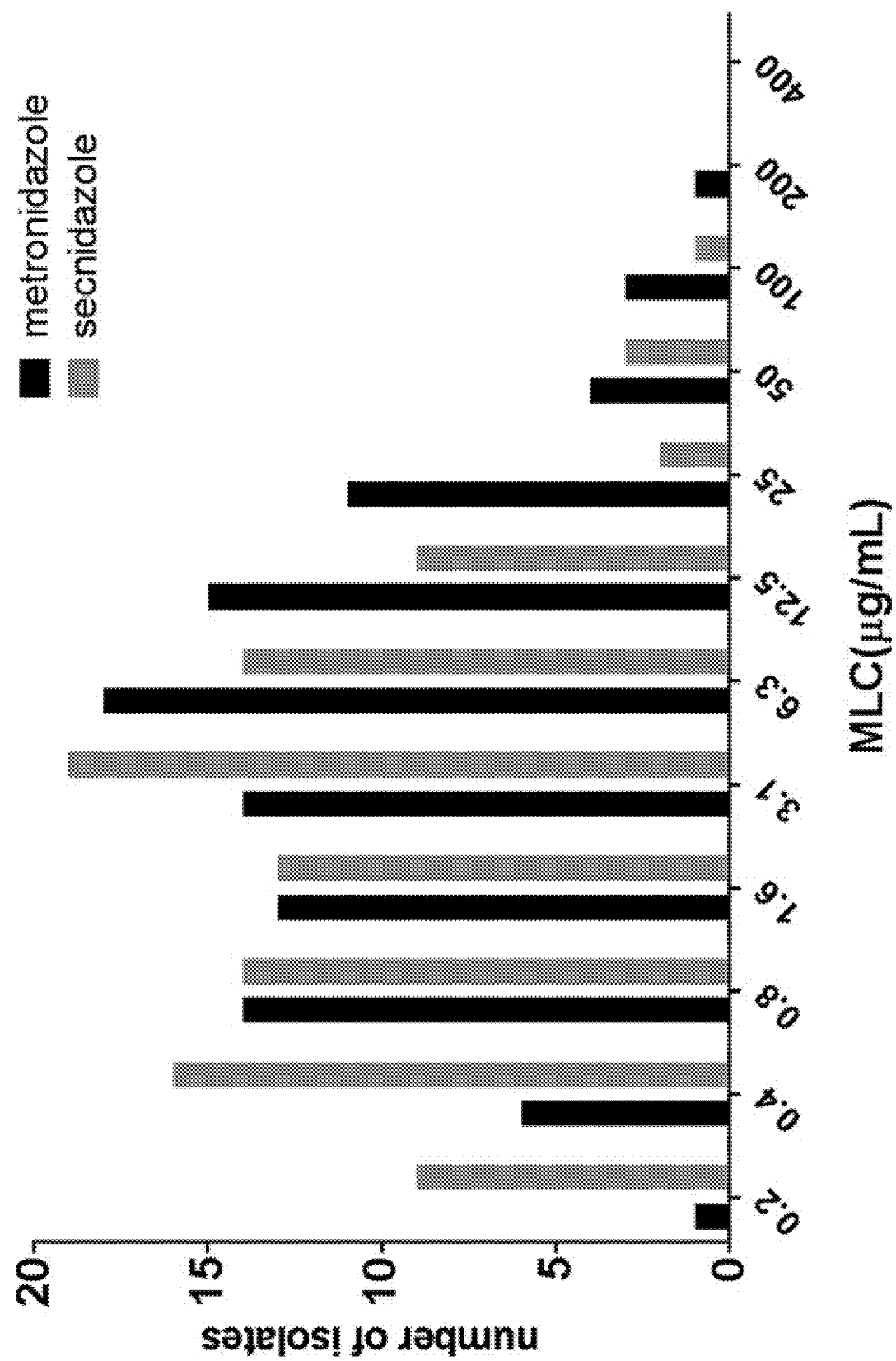

FIG. 6 illustrates a distribution of secnidazole and metronidazole minimum lethal concentrations ("MLCs") for 100 clinical *T. vaginalis* isolates. Susceptibility to metronidazole and secnidazole was defined as MLCs of <25 µg/ml, low-level resistance as MLCs of 50 µg/ml to 100 µg/ml, moderate-level resistance as MLCs of 200 µg/ml, and high-level resistance as MLCs of >400 µg/ml.

Figure 7:
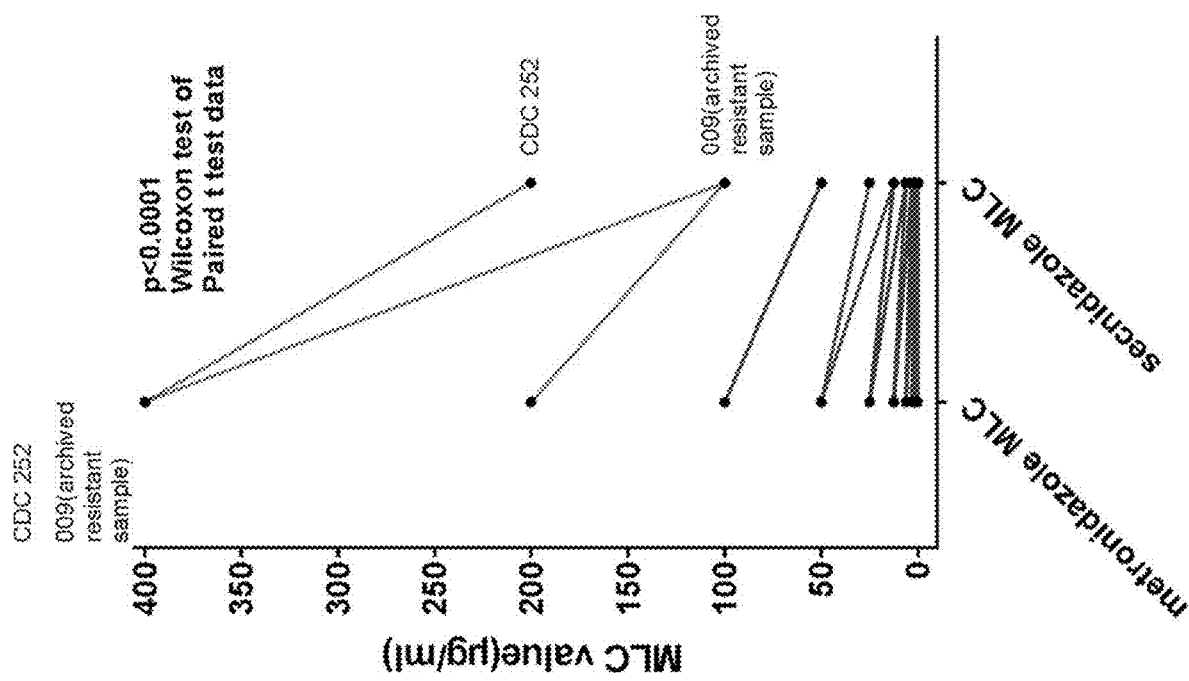

FIG. 7 illustrates a comparison of metronidazole and secnidazole activities in 100 *T. vaginalis* isolates. The MLCs for each drug were determined as described in this Figure in in Example 3—Microbiology—Susceptibility Testing below. The MLCs for metronidazole were consistently higher than for those for secnidazole (P<0.0001, Wilcoxon signed-rank test)

Figure 8:
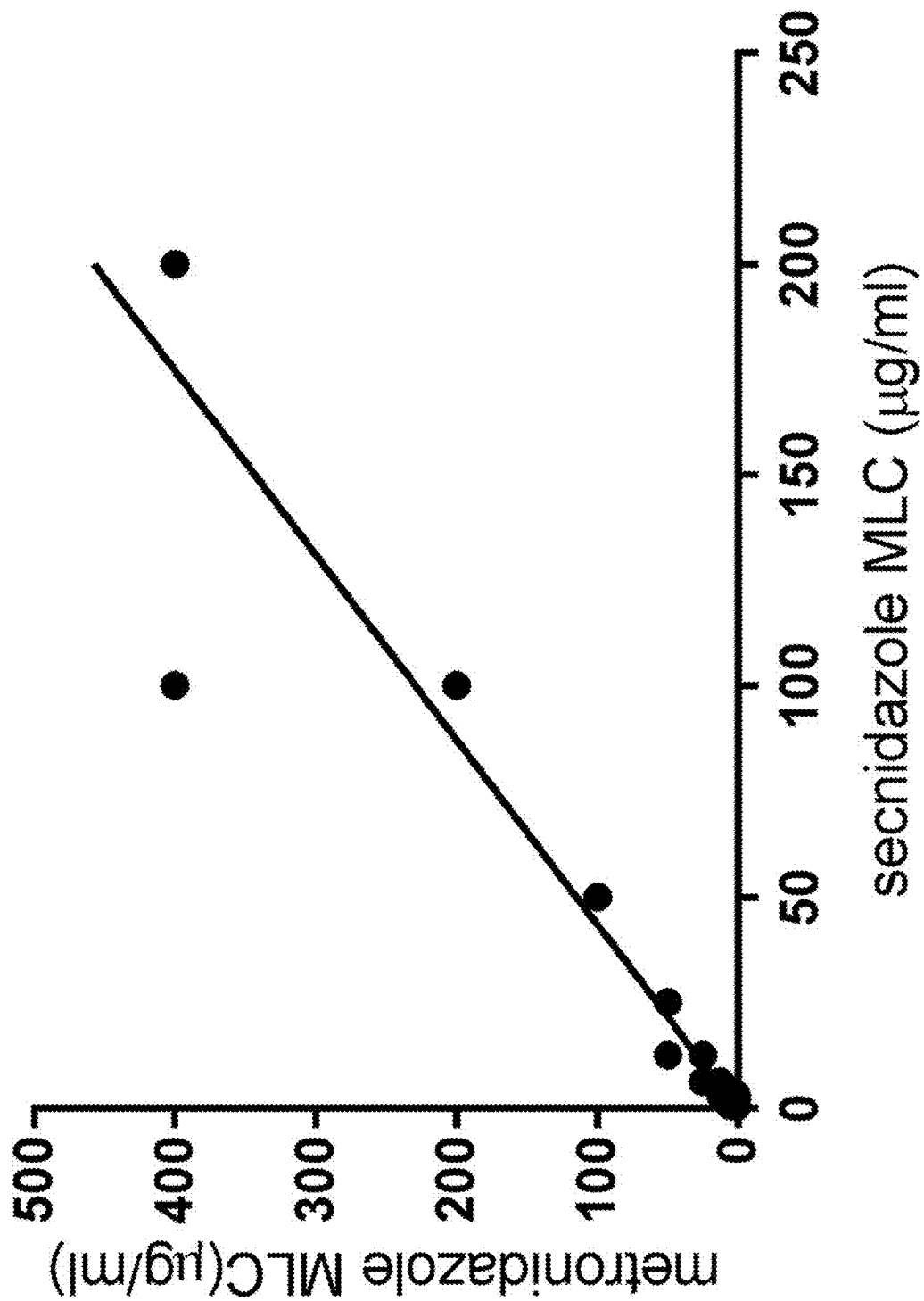

FIG. 8 illustrates a regression analyses of MLCs for metronidazole and secnidazole. The diagonal line represents the line of identity, indicating equal concentrations of the two drugs. The MLCs for metronidazole were strongly correlated with the MLCs for secnidazole (r=0.9496; P<0.0001).

DETAILED DESCRIPTION OF THE INVENTION

This description of the exemplary embodiments is intended to be read in connection with the accompanying drawings, which are to be considered part of the entire written description. Additionally, the section headings used herein are for organizational purposes only, and are not to be construed as limiting the subject matter described.

Before the formulations and methods are described, it is to be understood that this invention is not limited to the particular processes, compounds, or methodologies described, as these may vary. It is also to be understood that the terminology used in the description is for the purpose of describing the particular versions or embodiments only, and is not intended to limit the scope of the invention. Unless defined otherwise, all technical and scientific terms used herein have the same meanings as commonly understood by one of ordinary skill in the art. Although any methods and materials similar or equivalent to those described herein can be used in the practice or testing of embodiments of the invention, the preferred methods, devices, and materials are now described.

Definitions

The purpose of interpreting the specification, the following definition will apply and whenever appropriate, terms used in the singular will also include the plural and vice versa.

As used herein, the singular forms "a," "an" and "the" include plural referents unless the context clearly dictates otherwise.

As used herein, the term "about" is intended to qualify the numerical values that it modifies, denoting such a value as variable within a margin of error. When no particular margin of error (such as, for example, standard deviation to a mean value) is recited, the term "about" means plus or minus 10% of the numerical value of the number with which it is being used. For example, "about 50%" means in the range of 45% to 55%. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independent of the other endpoint. Also, any numerical value inherently contains certain errors necessarily resulting from the standard deviation found in their respective testing measurements.

As used herein, "bioequivalent" or "bioequivalence" is a term of art and is intended to be defined in accordance with Approved Drug Products with Therapeutic Equivalence Evaluations, 34th Edition, which is published by the U.S. Department of Health and Human Services, and is commonly known as the "Orange Book". Bioequivalence of different formulation of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. Detailed guidelines for establishing the bioequivalence of a formulation with a reference formulation have been published by the FDA Office of Generic Drugs, Division of Bioequivalence.

Two formulations whose PK parameters such as $C_{max}$, AUC, or $T_{max}$ differ by −20%/+25% or less are generally considered to be "bioequivalent." Another approach for average bioequivalence involves the calculation of a 90% confidence interval for the ratio of the averages (population geometric means) of the measures for the test and reference products. To establish BE, the calculated confidence interval should fall within usually about 80% to about 125% for the ratio of the product averages. In addition to this general approach, the others approach, including (a) logarithmic transformation of pharmacokinetic data, (b) methods to evaluate sequence effects and (c) methods to evaluate outlier data, may be useful for the establishment of bioequivalence. For example, in the above (a), the confidence interval should fall within usually about 80% to about 125% for the difference in the mean value of the logarithmic converted PK parameter.

As used herein, the term "daily dose amount" refers to the amount of API (such as secnidazole) per day that is administered or prescribed to a subject. This amount can be administered to the subject in multiple unit doses or a single unit dose, in a single time during the day or at multiple times during the day.

As used herein, the term "pharmaceutically acceptable" is that which is useful in preparing a pharmaceutical composition that is generally safe, non-toxic and neither biologically nor otherwise undesirable and includes that which is acceptable for human pharmaceutical use and/or veterinary use.

As used herein, the term "pharmaceutically acceptable salt" refers to a salt of secnidazole that is pharmaceutically acceptable, as defined above, and possesses the desired pharmaceutical activity. Such salt includes an acid addition salt formed with an inorganic acid, such as hydrochloric acid, hydrobromic acid, sulfuric acid, nitric acid, phosphoric acid, and the like, or with an organic acid, such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methylsulfonic acid, ethanesulfonic acid, 1,2-ethane-disulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylaceticacid, tertiary butylacetic acid, lauryl sulfuric acid, gluconic acid, glutamic acid, hydroxynaphthoic acid, salicylic acid, stearic acid, muconic acid, and the like. A pharmaceutically acceptable salt also includes a base addition salt that may be formed when one or more acidic protons present are capable of reacting with an inorganic or organic base. Acceptable inorganic bases include, but not limited to, sodium hydroxide, sodium carbonate, potassium hydroxide, aluminum hydroxide, calcium hydroxide, and the like. Acceptable organic bases include ethanolamine, diethanolamine, triethanolamine, tromethamine, N-methyl-lucamine, and the like.

As used herein, the terms "subject" or "patient" are interchangeable and may be taken to mean any living organism that may be treated with the methods/uses/compounds/compositions of the invention. As such, the term "subject" or "patient" may include, but is not limited to, mammal (non-human and human), primate, and other animals, such as domesticated animals (e.g., household pets, including cats and dogs) and non-domesticated animals (e.g., wildlife). In some embodiments, the term "subject" or "patient" is mammal, such as mice, rats, other rodents, rabbits, dogs, cats, swine, cattle, sheep, horses, primates, or humans. In some embodiments, the term "subject" or "patient" is a human. In some embodiments, the "subject" or "patient" is male or female; adult or child. In some embodiments, the subject is a human male or human female. In some embodiments, the subject is a healthy male or healthy female. In some embodiments, the subject is a pregnant female. In some embodiments, the subject is a healthy pregnant female. In some embodiments, the subject has trichomoniasis or *T. vaginalis* infection. In some embodiments, the subject is resistant to metronidazole and/or tinidazole. In some embodiments, the subject suffers from recurrent trichomoniasis or *T. vaginalis* infection, that is, the subject having had 2 or more trichomoniasis episodes or *T. vaginalis* infections in the past 12 months. In some embodiments, the subject is also HIV-positive, such as a HIV-positive male, a HIV-positive female or a HIV-positive pregnant female. In some embodiments, the subject is also infected (or co-infected) with bacterial vaginosis. In some embodiments, the subject is a female or pregnant female is HIV-positive and also infected (or co-infected) with bacterial vaginosis. In some embodiments, the subject is a child who is less than 18 years of age, or an adult who is at least 18 years old. In some embodiments, the human female is of an age ranging from a post-menarchal adolescent to a premenopausal woman. In some embodiments, the subject is a pregnant human female. In some embodiments, the subject is a female presenting with purulent malodorous discharge (associated with burning, pruritus, dysuria, frequency, lower abdominal pain), dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, an elevated vaginal pH (about 5.0 to about 6.0), or any combination thereof. In some embodiments, the subject is asymptomatic. In some embodiments, the subject is a female with confirmed trichomoniasis, wherein the diagnosis of *T. vaginalis* is confirmed by laboratory testing, including, but not limited to, motile trichomonads on wet mount, positive culture, increase in polymorphonuclear leukocytes, positive nucleic acid amplification test, or positive rapid antigen, nucleic acid probe test cervical cytology, or any combination thereof microscopy, including, but not limited to, culture subjects vaginal discharge on Diamond's medium (which is a key step in the evaluation of vaginal discharge, and is often the first step in the diagnostic evaluation for trichomoniasis) Microscopy is convenient and low cost. In some embodiments, nucleic acid amplification tests ("NAAT") can then be done for subjects with non-diagnostic (or negative) wet mounts. In some embodiments, if NAAT is not available, rapid diagnostic kits or culture are then performed. Additional laboratory tests include, but not limited to, the APTIMA® *T. vaginalis* assay, the APTIMA® TV assay, the Amplicor® assay (a PCR assay for detection of *Neisseria gonorrhoeae* and *Chlamydia trachomatis* that has been modified to detect *T. vaginalis* in vaginal/endocervical swabs or urine); NuSwab® Vaginitis Plus (VG+), or any combination thereof. Positive rapid antigen, nucleic acid probe tests also include, but not limited to, the Affirm® VP III Microbial Identification System, and the OSOM® *Trichomonas* Rapid Test. In some embodiments, the subject is a female with suspected trichomoniasis. In some embodiments, suspected trichomoniasis is indicated by the presence of purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), or any combination thereof. In some embodiments, the subject is a female or pregnant female also infected (or co-infected) with bacterial vaginosis, or has confirmed or suspected bacterial vaginosis. The disclosed methods/uses/compounds/compositions of the invention can be utilized to treat and/or prevent trichomoniasis or *T. vaginalis* infection in a subject in need thereof.

As used herein, the term "subject in need thereof," includes, but not limited to, a subject having or at risk for developing trichomoniasis or a *T. vaginalis* infection.

As used herein, the terms "treat," "treating" or "treatment" of a disease, condition or disorder includes: (a) preventing or delaying the appearance of clinical symptoms of the disease, condition or disorder developing in a subject that may be afflicted with or predisposed to the disease, condition or disorder but does not yet experience or display clinical or subclinical symptoms of the disease, condition or disorder; (b) inhibiting the disease, condition or disorder, i.e., arresting or reducing the development of the disease, condition or disorder or at least one clinical or subclinical symptom thereof; (c) ameliorating or lessening the severity of the disease, condition or disorder or at least one of its clinical or subclinical symptoms; or (d) relieving the disease, condition or disorder, i.e., causing regression of the disease, condition or disorder or at least one of its clinical or subclinical symptoms.

As used herein, the term "therapeutic" means an agent utilized to treat, combat, ameliorate or prevent an unwanted disease, condition or disorder in a subject.

The term "pharmaceutically effective amount" or "therapeutically effective amount" or "therapeutic dose" as used herein are used interchangeably and refer to the amount of an active agent or pharmaceutical compound or composition that elicits a clinical, biological or medicinal response in a tissue, system, animal, individual or human that is being sought by a researcher, veterinarian, medical doctor, or other clinical professional. A clinical, biological or medical response may include, for example, one or more of the following: (1) preventing or delaying a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, (3) ameliorating or lessening the severity of a disease, condition or disorder in an individual that is experiencing or exhibiting the pathology or symptoms of the disease, condition or disorder or reversing the pathology and/or symptoms experienced or exhibited by the individual, or (4) relieving the disease, condition or disorder, i.e., causing regression of the disease, condition or disorder or at least one of its clinical or subclinical symptoms, in the individual. The "therapeutically effective amount" will vary depending on the compound, the disease and its severity and the age, weight, physical condition and responsiveness of the subject to be treated.

As used herein, the term "volume-weighted particle size distribution" refers to a distribution where the contribution of each particle in the distribution relates to the volume of the particle (equivalent to the mass if the density is uniform), i.e., the particles contribution will be proportional to its size (see, e.g., *Powder Sampling and Particle Size Determination* by T. Allen, 1st Edition, Elsevier Science, 2003 and *Particle Size Measurement* by T. Allen, Chapman & Hall, 4th Edition, 1992). Static light scattering techniques such as laser diffraction and other techniques known in the art can be used to determine volume-weighted particle size distribution.

As used herein, the term "$C_{max}$" refers to the maximum concentration that a compound or drug achieves in a tested area in a subject after the drug has been administered and prior to the administration of the next dose. The tested area can be, for example, plasma.

As used herein, the term "$T_{max}$" refers to a period of time between the administration of a given dose of a compound or drug to a subject and the point in time when $C_{max}$ is reached.

Secnidazole

Secnidazole [1-(2-hydroxypropyl)-2-methyl-5-nitromidazole] is a 5-nitroimidazole derivative compound, having a molecular weight of 185.183 g/mol and a molecular formula of $C_7H_{11}N_3O_3$. The structure of secnidazole is shown below:

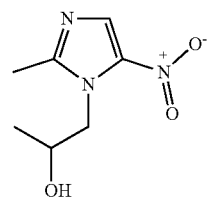

Embodiments described in this application are directed to secnidazole (and pharmaceutically acceptable salts thereof) formulations (such as SYM-1219) and the use of a secnidazole formulation for treating or preventing trichomoniasis or *T. vaginalis* infection in a subject in need thereof. One of the surprising effects of this invention is that it is a more effective therapy for trichomoniasis or *T. vaginalis* infection in a subject in need thereof with decreased side effects.

Embodiments described herein are directed to a method of treating or preventing trichomoniasis or *T. vaginalis* infection in a subject in need thereof comprising administering to the subject a therapeutically effective amount of secnidazole or a pharmaceutically acceptable salt thereof in a microgranule formulation. In some embodiments, the secnidazole or the pharmaceutically acceptable salt thereof in the microgranule formulation is administered orally. In some embodiments, the secnidazole or the pharmaceutically acceptable salt thereof in the microgranule formulation comprises a plurality of microgranules. In some embodiments, each microgranule comprises an inactive core (such as a sugar core, microcrystalline cellulose core or any core that does not contain any API) and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, wherein the therapeutically effective amount of secnidazole is an amount of secnidazole that exhibits a $C_{max}$ of secnidazole in the subject of about 17.4 µg/ml and about 26.5 µg/ml, or about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In another embodiment, a method of treating or preventing trichomoniasis or *T. vaginalis* infection in a subject in need thereof, the method comprising administering to the subject a microgranule formulation comprising a therapeutically effective amount of secnidazole, wherein the microgranule formulation comprises a plurality of microgranules having a volume-weighted particle size distribution within a microgranule population, wherein the volume-weighted particle size distribution as measured by mean diameter from a representative sample of the microgranule population comprises (a) at least 10% of the microgranule population having a volume-weighted particle size equal to or larger than about 470 micrometers, and/or (b) 50% of the microgranule population having a volume-weighted particle size in a range of from about 640 micrometers to about 810 micrometers; and/or (c) 90% of the microgranule population having a volume-weighted particle size smaller than about 1170 micrometers. In some embodiments, the mean diameter is measured by laser diffraction. In some embodiments, wherein each microgranule comprises a sugar core or a microcrystalline cellulose core, and a layer outside of the sugar core or the microcrystalline cellulose core, the layer comprising secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, wherein the therapeutically effective amount of secnidazole is an amount of secnidazole that exhibits a $C_{max}$ of secnidazole in the subject of about 17.4 μg/ml and about 26.5 μg/ml, or about 34.5 μg/ml to about 58.3 μg/ml, or about 26 μg/ml to about 34 μg/ml, or about 26 μg/ml to about 58 μg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In another embodiment, a method of treating or preventing trichomoniasis or *T. vaginalis* infection in a subject in need thereof, the method comprising administering to the subject a microgranule formulation comprising a therapeutically effective amount of nitroimidazole compound or a pharmaceutically acceptable salt thereof, wherein the microgranule formulation comprises a plurality of microgranules, wherein each microgranule comprises a core and a coating, wherein the core comprises the nitroimidazole compound or the pharmaceutically acceptable salt thereof, and wherein the coating surrounds the core. In some embodiments, the nitroimidazole compound is secnidazole, metronidazole, tinidazole, nimorazole, dimetridazole, 6-Amino PA824, orinidazole, megazol, azanidazole, benznidazole, pimonidazole or a combination thereof. In some embodiments, the nitroimidazole compound is secnidazole. In some embodiments, the nitroimidazole compound is in the core. In some embodiments, the nitroimidazole compound comprises at least 70% of the core by weight. In some embodiments, the coating covers partially or all of the exterior surface of the core. In some embodiments, the coating does not contain a nitroimidazole compound. In some embodiments, the nitroimidazole compound comprises at least about 70% of the core by weight; at least about 75% of the core by weight; at least about 80% of the core by weight; at least about 85% of the core by weight; at least about 90% of the core by weight; or about at least about 95% of the core by weight. In some embodiments, the nitroimidazole compound comprises about 70% of the core by weight; about 75% of the core by weight; about 80% of the core by weight; about 85% of the core by weight; about 90% of the core by weight; or about 95% of the core by weight. In some embodiments, the plurality of microgranules comprise about 1 gram to about 6 grams of the nitroimidazole compound. In some embodiments, the plurality of microgranules comprises a therapeutically effective amount of nitroimidazole compound. In some embodiments, the core further comprises at least one polymer. In some embodiments, the polymer can be, but not limited to, Avicel®, Methocel®, hydroxyl propyl cellulose, acacia, guar gum, povidone, lactose monohydrate, or a combination thereof. In some embodiments, the core further comprises Avicel®, Methocel® or a combination thereof. In some embodiments, the core further comprises cellulose microcrystalline (such as the product cellulose microcrystalline sold under the trademark Avicel® PH-101), methyl cellulose (such as the product methyl cellulose sold under the trademark Methocel® AV15LV) or a combination thereof. In some embodiments, the polymer comprises about 30% of the core by weight. In some embodiments, the ratio of the nitroimidazole compound to the at least one polymer in the core may be about 70:30, or lesser than about 70:30, or more than greater than 70:30. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function. In some embodiments, the core comprises an active ingredient and at least one polymer. In some embodiments, the active ingredient is secnidazole or other nitroimidazole compounds described herein.

In some embodiments, the core further comprises one or more dispersion agent or binding agent. In some embodiments, the dispersion agent or binding agent includes, but not limited to, microcrystalline cellulose, methylcellulose, hydroxyl propyl cellulose, acacia, guar gum, povidone, lactose monohydrate, or a combination thereof.

In some embodiments, the core further comprises one or more microlubricant or anti-tacking agent. In some embodiments, the microlubricant or anti-tacking agent includes, but not limited to, sodium stearate, magnesium stearate, stearic acid, talc or a combination thereof. In some embodiments, the core further comprises a binder (such as, but not limited to, starch).

In some embodiments, the coating may be modified to modulate drug absorption of the drug by varying the composition of the coating, the percentage weight of the composition, or any combination thereof.

In some embodiments, the coating comprises a polymer. In some embodiment, the polymer includes, but not limited to, polyvinylpyrrolidone, ethylcellulose, the product 2-Methylprop-2-enoic acid-N—N-dimethylmethanamine (2/1) sold under the trademark Eudragit® RL, the product anionic copolymers of methacrylic acid and methyl methacrylate at a ratio of approximately 1:1 sold under the trademark Eudragit® L, the product amino methacrylate copolymer sold under the trademark Eudragit® E, the product anionic copolymers of methacrylic acid and methyl methacrylate at a ratio of approximately 1:2 sold under the trademark Eudragit® S, cellulose acetate, polyvinyl alcohol, shellac, methacrylic acid copolymers, cellulose acetate phthalate, hydroxypropylmethylcellulose phthalate, hydroxypropylmethylcellulose acetate succinate, cellulose acetate trimellitate and polyvinyl acetate phthalate. In some embodiments, the polymer can be, but not limited to, Eudagrit®, ethyl cellulose, Methocel®, glyceryl behenate, or a combination thereof. In some embodiments, the polymer is the product ethyl acrylate-methyl methacrylate copolymer sold under the trademark Eudagrit® NE30D. In some embodiments, the polymer is the product ethyl acrylate-methyl methacrylate copolymer sold under the trademark Eudagrit® NE30D comprises about 5.795% of the composition of weight.

In some embodiments, the coating further comprises a polyether polymer. In some embodiments, the polyether polymer can be, but limited to, polyethylene glycol ("PEG"), acetyl tributyl citrate, triethyl citrate, dibutyl phthalate, dibutyl sebacate, gelatin, propylene glycol, triacetin or a combination thereof. In some embodiments, the polyether polymer is PEG. In some embodiments, the PEG is PEG 4000. In some embodiments, the coating comprises about 10% to about 13% of the composition by weight. In some embodiments, the coating comprises about 13% or less than about 13% of the composition by weight. In some embodiments, the coating comprises about 10% or more than 10% of the composition by weight. In some embodiments, the PEG (such as PEG 4000) comprises about 1.75% of the composition by weight. In some embodiments, the PEG (such as PEG 4000) comprises about 1.75% of an individual microgranule by weight.

In some embodiments, other auxiliary coating aids such as a minor amount (about 1 to about 5% by weight based on the active core component and the total weight of the final coating) of a plasticizer such as, but not limited to, acetyltributyl citrate, triacetin, acetylated monoglyceride, grape seed oil, olive oil, sesame oil, acetyltriethylcitrate, glycerin sorbitol, diethyldioxaldiate, diethylmaldiate, diethylfumarate, dibutylsuccinate, diethylmdialdionate, dioctylphthaldiate, dibutylsebacate, triethylcitrate, tributyldicitrate, glyceroltributyrate, polyethyleneglycol, propylene glycol or a combination thereof with or without an antisticking agent (such as, but limited to, a silicate such as, but not limited to, talc). In some embodiments, the coating further comprises talc.

In some embodiments, the pharmaceutical composition further comprises talc. In some embodiments, the plurality of microgranules further comprises talc. In some embodiments, the talc is a blending agent.

In some embodiments, the core comprises a spheronized microgranule. In some embodiments, the microgranules may be formed by wet granulation followed by extrusion and spheronization. In some embodiments, the core further comprises a binder. In some embodiments, the binder may be starch.

It is also known in the art that the active ingredients may be contained in such compositions with pharmaceutically acceptable diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, G. S. Banker & C. T. Rhodes, 4$^{th}$ Edition, CRC Press (2002); *Goodman & Gilman's The Pharmaceutical Basis of Therapeutics*, L. L. Brunton, R. Hilal-Dandan & B. C. Knollmann, 13th Edition, McGraw-Hill Education (2018); *Remington's Pharmaceutical Sciences* by E. W. Martin; and *Remington: The Science and Practice of Pharmacy*, Loyd V. Allen (Ed.), 22$^{nd}$ Edition, Pharmaceutical Press (2013) can be consulted.

In some embodiments, the therapeutically effective amount of secnidazole in the microgranule formulation is about 1 gram to about 4 grams, or about 1 gram to about 6 grams.

In some embodiments, the therapeutically effective amount of secnidazole in the microgranule formulation is 1 gram, 2 grams, 3 grams, 4 grams, 5 grams, or 6 grams. In some embodiments, the therapeutically effective amount of secnidazole in the microgranule formulation is 2 grams, 4 grams, or 6 grams.

In some embodiments, the plurality of microgranules comprising a daily dose amount of a nitroimidazole compound (such as secnidazole). In some embodiments, the plurality of microgranules comprising a daily dose amount of a nitroimidazole compound may be configured as a single unit dose or multiple unit doses. In some embodiments, the multiple unit doses can be two, three or four unit doses per day. In some embodiments, the unit dose may be a portion of the daily dose amount of the nitroimidazole compound. In some embodiments, the nitroimidazole compound is secnidazole and the daily dose amount is about 1 gram, about 2 grams, about 3 grams about 4 grams, about 5 grams, or about 6 grams. In some embodiments, the daily dose amount can be configured as one, two, three, four or more unit doses per day. For example, the plurality of microgranules comprising about 2 grams of secnidazole may be configured as 2 unit doses, each unit dose comprising about 1 gram of secnidazole. Likewise, the plurality of microgranules comprising about 2 grams of secnidazole may be configured as 4 unit doses, each until dose comprising about 0.5 grams of secnidazole. In some embodiments, the unit doses in a multiple unit dose regime may have unit doses of equal or different amounts of secnidazole. For example, the plurality of microgranules comprising about 2 grams of secnidazole may be configured as 3 unit doses, where one unit dose comprises about 1 gram of secnidazole and the other two unit doses each comprises about 0.5 grams of secnidazole.

The microgranule formulations described herein may be prepared, packaged, or sold in bulk, as a single unit dose or as multiple unit doses and may be administered in orally.

In some embodiments, microgranule formulation is packaged as a unit dose or a single unit dose. A unit dose, also defined as single dose herein, is a dosage in a form that includes therapeutically effective amount of secnidazole in a microgranule formulation. The unit dose could be administered to a subject as a single unit dose, wherein the therapeutically effective amount of secnidazole in a microgranule formulation is included in a single package, such as, one pouch, packet, sachet, or bottle. In some embodiments, the microgranule formulation is packaged in such a way as to provide a barrier to oxygen and moisture. In some embodiments, the microgranule formulation is packaged in a foil pouch or sachet. In some embodiments, the foil pouch or sachet is made of a polyester-faced laminated or polyethylene-metallocene-lined aluminum foil pouching material that provides a barrier to oxygen and moisture. In some embodiments, the pouch or sachet is made from a material such as, but not limited to, the product polyester-faced laminated pouching material sold under the trademark FASSON® RAPID-ROLL® White Cosmetic Web 350 HB. In some embodiments, the microgranule formulation can include a plurality of microgranules comprising inert cores made from microcrystalline cellulose. For example, the inert cores made from microcrystalline cellulose can replace sugar spheres/sugar cores. In some embodiments, glycerol monostearate (e.g., the product glycerol monostearate sold under the trademark PLASCRYL® T20 by Evonik) can be used as an anti-tacking agent. For example, glycerol monostearate can be used in Eudragit coatings in place of talc.

In some embodiments, therapeutically effective amounts, daily doses, or single unit doses of the secnidazole (or other nitroimidazole composition) microgranule formulations described herein may be administered once per day or multiple times per day, such as twice per day; 3 times per day; 4 times per day; 5 times per day; or more than 5 times per day. In some embodiments, the treatment or use period can be 1 day, 2 days, 3 days, 4 days, 5 days, 6, days, 7 days, 8 days, 9 days, 10 days, 11 days, 12, days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days. In some embodiments, the dosing schedule of the invention can be about 1 gram, about 2 grams, about 3 grams, about 5 grams, or about 6 grams of secnidazole (or other nitroimidazole composition) per day for 1 day, 2 days, 3 days, 4 days, 5 days, 6, days, 7 days, 8 days, 9 days, 10 days, 11 days, 12, days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days. In some embodiments, the dosing can be done with 1 day, 2 days, 3 days, 4 days or more than 4 days apart each dose. For example, the dosing schedule of the invention can be about 2 grams of secnidazole (or other nitroimidazole composition) per day, taken about 3 days or about 4 days apart×2. The invention herein contemplates all of the dosage schedule combinations set forth in this application.

Embodiments are also directed to a dosage regimen for administering a therapeutically effective amount of a nitroimidazole compound (such as secnidazole) for the methods and uses described herein. For example, in some embodiments, the methods and uses described herein can comprises a dosage regimen that includes a plurality of daily doses having an equal amount of the nitroimidazole compound as the initial dose in one or more unit doses. In other embodiments, the dosage regimen can include an initial dose of the nitroimidazole compound in one or more unit doses, then one or more subsequent daily doses having a lower amount of the nitroimidazole compound than the initial doses in one or more unit dose. The dosage regimen may administer one or more initial doses followed by one or more maintenance doses. The one or more doses following the administering of the one or more initial doses can be maintenance doses. Such maintenance doses can have a lower or higher amount of the nitroimidazole compound than the one or more initial doses.

In some embodiments, the therapeutically effective amount of secnidazole in a microgranule formulation is administered as a single dose. In some embodiments, the therapeutically effective amount of secnidazole in a microgranule formulation administered as a single dose is the only dose required to be administered to the subject to achieve a post-treatment clinical outcome, resolution of one or more symptoms of trichomoniasis or *T. vaginalis* infection, or a combination thereof.

In some embodiments, the methods and uses described herein further comprises administering paromomycin, tinidazole, metronidazole, boric acid or a combination thereof to a subject who is resistant or allergic to metronidazole and/or tinidazole, or the subject who is infected metronidazole and/or tinidazole-resistant trichomoniasis with or when metronidazole and/or tinidazole is contraindicated. In some embodiments, the administration of paromomycin, tinidazole, metronidazole, boric acid or a combination thereof to the subject is on the same day or a different day relative to the administration of secnidazole to the subject. In some embodiments, the administration of the compounds of the combination therapy (e.g., secnidazole, paromomycin, tinidazole, metronidazole, boric acid or a combination thereof) are administered concomitantly or sequentially.

In some embodiments, the methods and uses described herein further comprises co-administering an additional compound selected from EE2, NET, or a combination thereof. In some embodiments, the additional compound is administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound selected from EE2, NET, or a combination thereof. In some embodiments, the subject has a resolution of one or more symptoms of trichomoniasis or *T. vaginalis* infection within up to about seven days after administration to the subject. In some embodiments, the subject has an alleviation of one or more symptoms of trichomoniasis or *T. vaginalis* infection within up to about three days after administration to the subject.

In some embodiments, the subject is a male or female; adult or child. In some embodiments, the subject is a healthy male or healthy female. In some embodiments, the subject is a pregnant female. In some embodiments, the subject is a healthy pregnant female. In some embodiments, the subject has confirmed or suspected trichomoniasis or *T. vaginalis* infection. In some embodiments, the subject is resistant to metronidazole and/or tinidazole. In some embodiments, the subject suffers from recurrent trichomoniasis or *T. vaginalis* infection, that is, the subject having had 2 or more trichomoniasis episodes or *T. vaginalis* infections in the past 12 months. In some embodiments, the subject is also HIV-positive, such as a HIV-positive male, a HIV-positive female or a HIV-positive pregnant female. In some embodiments, the subject is also infected (or co-infected) with bacterial vaginosis. In some embodiments, the subject is a female or pregnant female is HIV-positive and also infected (or co-infected) with bacterial vaginosis. In some embodiments, the subject is a child who is less than 18 years of age, or an adult who is at least 18 years old.

In some embodiments, the subject is a female or pregnant female also infected (or co-infected) with bacterial vaginosis, or has confirmed or suspected bacterial vaginosis. In some embodiments, the subject is a female having had 3 or fewer bacterial vaginosis infections/episodes in the past 12 months. In some embodiments, the subject is a female having had 4 or more bacterial vaginosis infections/episodes in the past 12 months. In some embodiments, the subject is a female presenting with thin, homogeneous vaginal discharge, a positive KOH Whiff test, vaginal fluid pH greater than or equal to 4.7, and the presence of "clue cells" greater than 20% of total epithelial cells, or any combination thereof. In some embodiments, the female with bacterial vaginosis presents with the four Amsel criteria parameters and a gram stain slide Nugent score equal to, or higher than four on bacterial analysis of vaginal samples. In some embodiments, the four Amsel criteria parameters are abnormal vaginal discharge (e.g., thin, homogenous vaginal discharge), a positive KOH Whiff test, vaginal fluid pH greater than or equal to 4.7, and the presence of clue cells greater than 20% of total epithelial cells. (See Amsel).

Some embodiments further comprise determining a post-treatment clinical outcome. In some embodiments, a post-treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative *T. vaginalis* test, a negative KOH Whiff test, and clue cells less than 20% of total epithelial cells, post-treatment. In some embodiments, a clinical outcome responder is a subject with a gram stain slide Nugent score of less than four, post-treatment. In some embodiments, a clinical outcome responder is a subject with normal vaginal discharge, a negative *T. vaginalis* test, a negative KOH Whiff test, clue cells less than 20% of total epithelial cells), and a gram stain slide Nugent score of less than four, post-treatment. In some embodiments, administering to the subject a therapeutically effective amount of secnidazole in a microgranule formulation results in better than expected effectiveness than U.S. FDA-approved drugs used in the treatment or prevention of trichomoniasis or *T. vaginalis* infection. In some embodiments, administering to the subject a therapeutically effective amount of secnidazole in a microgranule formulation results in superior effectiveness than FDA-approved drugs used in the treatment or prevention of trichomoniasis or *T. vaginalis* infection. In some embodiments, administering to the subject a therapeutically effective amount of secnidazole in a microgranule formulation results in a higher rate of clinical cure than FDA-approved drugs used in the treatment or prevention of trichomoniasis or *T. vaginalis* infection. In some embodiments, administering to the subject a therapeutically effective amount of secnidazole in a microgranule formulation results in a better than expected safety profile than FDA-approved drugs used in the treatment or prevention of trichomoniasis or *T. vaginalis* infection. In some embodiments, administering to the subject a therapeutically effective amount of secnidazole in a microgranule formulation results in a more favorable safety profile than FDA-approved drugs used in the treatment or prevention of trichomoniasis or *T. vaginalis* infection.

In some embodiments, wherein the therapeutically effective amount of secnidazole in the microgranule formulation administered as a single dose is the only dose required to be administered to the subject to achieve a post-treatment clinical outcome by resolution of one or more symptoms of trichomoniasis or *T. vaginalis* infection. By way of example, the one or more symptoms of trichomoniasis or *T. vaginalis* infection include, but not limited to:

For Men: Itching or irritation inside the penis; burning with urination or after ejaculation; and/or discharge from the penis.

For Women: Itching, burning, redness or soreness of the genitals; pain with urination; a change in vaginal discharge (i.e., thin discharge or increased volume) that is clear, white, gray, yellowish or greenish with an unusual fishy smell; and/or pain with sexual intercourse.

Other symptoms of trichomoniasis or *T. vaginalis* infection include, but not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof.

Embodiments herein are also directed to a microgranule formulation for treating or preventing trichomoniasis or *T.* vaginalis infection in a subject in need thereof comprising secnidazole or a pharmaceutically acceptable salt thereof. In some embodiments, the microgranule formulation comprises a therapeutically effective amount of secnidazole or a pharmaceutically acceptable salt thereof. In some embodiments, the secnidazole or the pharmaceutically acceptable salt thereof in the microgranule formulation comprises a plurality of microgranules. In some embodiments, each microgranule comprises an inactive core (such as a sugar core, microcrystalline cellulose core or any core that does not contain any API and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, wherein the therapeutically effective amount of secnidazole is an amount of secnidazole that exhibits a $C_{max}$ of secnidazole in the subject of about 17.4 µg/ml and about 26.5 µg/ml, or about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In another embodiment, a microgranule formulation for treating or preventing trichomoniasis or *T. vaginalis* infection in a subject in need thereof comprising a microgranule formulation comprising a therapeutically effective amount of secnidazole, wherein the microgranule formulation comprises a plurality of microgranules having a volume-weighted particle size distribution within a microgranule population, wherein the volume-weighted particle size distribution as measured by mean diameter from a representative sample of the microgranule population comprises (a) at least 10% of the microgranule population having a volume-weighted particle size equal to or larger than about 470 micrometers, and/or (b) 50% of the microgranule population having a volume-weighted particle size in a range of from about 640 micrometers to about 810 micrometers; and/or (c) 90% of the microgranule population having a volume-weighted particle size smaller than about 1170 micrometers. In some embodiments, the mean diameter is measured by laser diffraction. In some embodiments, wherein each microgranule comprises a sugar core or a microcrystalline cellulose core, and a layer outside of the sugar core or the microcrystalline cellulose core, the layer comprising secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, wherein the therapeutically effective amount of secnidazole is an amount of secnidazole that exhibits a $C_{max}$ of secnidazole in the subject of about 17.4 µg/ml and about 26.5 µg/ml, or about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In another embodiment, a microgranule formulation for treating or preventing trichomoniasis or *T. vaginalis* infection in a subject in need thereof, the microgranule formulation comprises a plurality of microgranules, wherein the plurality of microgranules comprises a therapeutically effective amount of nitroimidazole compound or a pharmaceutically acceptable salt thereof, wherein each microgranule comprises a core and a coating, wherein the core comprises the nitroimidazole compound or the pharmaceutically acceptable salt thereof, and wherein the coating surrounds the core. In some embodiments, the nitroimidazole compound is secnidazole, metronidazole, tinidazole, nimorazole, dimetridazole, 6-Amino PA824, orinidazole, megazol, azanidazole, benznidazole, pimonidazole or a combination thereof. In some embodiments, the nitroimidazole compound is secnidazole. In some embodiments, the nitroimidazole compound is in the core. In some embodiments, the nitroimidazole compound comprises at least 70% of the core by weight. In some embodiments, the coating covers partially or all of the exterior surface of the core. In some embodiments, the coating does not contain a nitroimidazole compound. In some embodiments, the nitroimidazole compound comprises at least about 70% of the core by weight; at least about 75% of the core by weight; at least about 80% of the core by weight; at least about 85% of the core by weight; at least about 90% of the core by weight; or about at least about 95% of the core by weight. In some embodiments, the nitroimidazole compound comprises about 70% of the core by weight; about 75% of the core by weight; about 80% of the core by weight; about 85% of the core by weight; about 90% of the core by weight; or about 95% of the core by weight. In some embodiments, the plurality of microgranules comprise about 1 gram to about 6 grams of the nitroimidazole compound. In some embodiments, the plurality of microgranules comprises a therapeutically effective amount of nitroimidazole compound. In some embodiments, the core further comprises at least one polymer. In some embodiments, the polymer can be, but not limited to, Avicel®, Methocel®, hydroxyl propyl cellulose, acacia, guar gum, povidone, lactose monohydrate, or a combination thereof. In some embodiments, the core further comprises Avicel®, Methocel® or a combination thereof. In some embodiments, the core further comprises cellulose microcrystalline (such as the product cellulose microcrystalline sold under the trademark Avicel® PH-101), methyl cellulose (such as the product methyl cellulose sold under the trademark Methocel® AV15LV) or a combination thereof. In some embodiments, the polymer comprises about 30% of the core by weight. In some embodiments, the ratio of the nitroimidazole compound to the at least one polymer in the core may be about 70:30, or lesser than about 70:30, or more than greater than 70:30. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function. In some embodiments, the core comprises an active ingredient and at least one polymer. In some embodiments, the active ingredient is secnidazole or other nitroimidazole compounds described herein.

In some embodiments, the microgranule formulation is a delayed release formulation and comprises a plurality of microgranules. In some embodiments, the delayed release formulation, when administered to a subject provides a secnidazole concentration profile characterized by a change in secnidazole concentration as a function of time that is less than that of an immediate release secnidazole microgranule formulation. In some embodiments, the delayed release formulation, when administered to a subject provides a secnidazole concentration profile characterized by a $T_{max}$ that is greater than that of an immediate release secnidazole microgranule formulation. In some embodiments, the delayed release formulation, when administered to a subject provides a secnidazole concentration profile characterized by a $C_{max}$ that is greater than that of an immediate release secnidazole microgranule formulation. In some embodiments, the delayed release formulation, when administered to a subject provides a secnidazole concentration profile characterized by an AUC that is greater than that of an immediate release secnidazole microgranule formulation. In some embodiments, the microgranule formulation comprises about 1 gram to about 6 grams of secnidazole or a pharmaceutically acceptable salt thereof. In some embodiments, each microgranule comprises an inactive core (such as a sugar core, microcrystalline cellulose core or any core that does not contain any API and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, the microgranule formulation comprises about 1 gram, about 2 grams, about 3 grams, about 4 grams, about 5 grams, or about 6 grams of secnidazole or a pharmaceutically acceptable salt thereof. In some embodiments, the microgranule formulation is suitable for oral administration. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

Embodiments herein are also directed to a use of secnidazole or a pharmaceutically acceptable salt thereof in a microgranule formulation in the manufacture of a medicament for the treatment or prevention of trichomoniasis or *T. vaginalis* infection in a subject, wherein the microgranule formulation comprises a therapeutically effective amount of secnidazole or the pharmaceutically acceptable salt thereof in the microgranule formulation. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 34.5 µg/ml and about 58.3 µg/ml, or about 26 µg/ml to about 34 µg/ml, or about 26 µg/ml to about 58 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 17.4 µg/ml and about 26.5 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of about 3 hours to about 4 hours, or about 6 hours to about 24 hours, or about 2 hours to about 24 hours. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of 2 hours to 6 hours, or about 6 hours to about 24 hours, or about 2 hours to about 24 hours. In some embodiments, the plurality of microgranules each having a particle size range of about 400 micrometers to about 841 micrometers.

In another embodiment, use of secnidazole or a pharmaceutically acceptable salt thereof in a microgranule formulation for the treatment or prevention of trichomoniasis or *T. vaginalis* infection in a subject, wherein the microgranule formulation comprises a therapeutically effective amount of secnidazole or the pharmaceutically acceptable salt thereof in the microgranule formulation. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 34.5 µg/ml and about 58.3 µg/ml, or about 26 µg/ml to about 34 µg/ml, or about 26 µg/ml to about 58 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibits a $C_{max}$ of between about 17.4 µg/ml and about 26.5 µg/ml. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of about 3 hours to about 4 hours, or about 6 hours to about 24 hours, or about 2 hours to about 24 hours. In some embodiments, wherein the therapeutically effective amount of secnidazole or the pharmaceutically acceptable salt thereof in the microgranule formulation is an amount of secnidazole or the pharmaceutically acceptable salt thereof, respectively, that exhibit a $T_{max}$ of about 2 hours to about 6 hours. In some embodiments, the plurality of microgranules each having a particle size range of about 400 micrometers to about 841 micrometers.

In another embodiment, use of a pharmaceutical composition comprising a plurality of microgranules for treating or preventing trichomoniasis or *T. vaginalis* infection in a subject, wherein the plurality of microgranules comprises a therapeutically effective amount of secnidazole or a pharmaceutically acceptable salt thereof, wherein the plurality of microgranules having a volume-weighted particle size distribution within a microgranule population, wherein the volume-weighted particle size distribution as measured by mean diameter using laser diffraction from a representative sample of the microgranule population comprises at least about 10% of the microgranule population having a volume-weighted particle size about equal to or larger no less than 470 micrometers, and/or about 50% of the microgranule population having a volume-weighted particle size between about no less than 640 micrometers and about no more than 810 micrometers, and/or about 90% of the microgranule population having a volume-weighted particle size about no more than 1170 micrometers.

In another embodiment, use of a pharmaceutical composition comprising a plurality of microgranules for treating or preventing trichomoniasis or *T. vaginalis* infection in a subject, wherein the plurality of microgranules comprises a therapeutically effective amount of secnidazole or a pharmaceutically acceptable salt thereof, wherein each microgranule comprises a core and a coating, wherein the core comprises an active ingredient and at least one polymer, wherein the active ingredient is the secnidazole or the pharmaceutically acceptable salt thereof, wherein the secnidazole or the pharmaceutically acceptable salt thereof comprises at least 70% of the core by weight, wherein the coating is on the outside of the core, wherein the therapeutically effective amount of the secnidazole or the pharmaceutically acceptable salt thereof is about 1 gram, about 2 grams, about 3 grams, about 4 grams, about 5 grams, or about 6 grams; and wherein the pharmaceutical composition is for oral administration.

In another embodiment, use of a pharmaceutical composition in preparation of a medicament comprising a plurality of microgranules for treating or preventing trichomoniasis or *T. vaginalis* infection in a subject, wherein the plurality of microgranules comprises a therapeutically effective amount of secnidazole or a pharmaceutically acceptable salt thereof, wherein each microgranule comprises a core and a coating, wherein the core comprises an active ingredient and at least one polymer, wherein the active ingredient is the secnidazole or the pharmaceutically acceptable salt thereof, wherein the secnidazole or the pharmaceutically acceptable salt thereof comprises at least 70% of the core by weight, wherein the coating is on the outside of the core, wherein the therapeutically effective amount of the secnidazole or the pharmaceutically acceptable salt thereof is about 1 gram, about 2 grams, about 3 grams, about 4 grams, about 5 grams, or about 6 grams; and wherein the pharmaceutical composition is for oral administration.

Embodiments herein are also directed to a method of making the secnidazole microgranule formulation, the method comprising coating one or more sugar spheres and/or microcrystalline cellulose spheres. In some embodiments, the process comprises (a) layering secnidazole on one or more sugar spheres and/or microcrystalline cellulose spheres; (b) layering a seal coating on top of the secnidazole on the one or more sugar spheres and/or microcrystalline cellulose spheres to produce end products of (b), wherein the seal coating comprises polyethylene glycol (such as polyethylene glycol 4000); (c) layering a top coating on top of the end products of (b) to product end products of (c), wherein the top coating comprises with ethyl acrylate-methyl methacrylate copolymer (such as the product ethyl acrylate-methyl methacrylate copolymer sold under the trademark Eudragit® NE30D); and (d) curing the end products of (c). In some embodiments, the process comprises (a) layering secnidazole on one or more sugar spheres and/or microcrystalline cellulose spheres; (b) layering a seal coating on top of the secnidazole on the one or more sugar spheres and/or microcrystalline cellulose spheres to produce end products of (b), wherein the seal coating comprises ethyl acrylate-methyl methacrylate copolymer (such as the product ethyl acrylate-methyl methacrylate copolymer sold under the trademark Eudragit® NE30D); and (c) curing the end products of (b). In some embodiments, coating with ethyl acrylate-methyl methacrylate copolymer (such as the product ethyl acrylate-methyl methacrylate copolymer sold under the trademark Eudragit® NE30D) provides a delayed release formulation. Other grades of the product ethyl acrylate-methyl methacrylate copolymer sold under the trademark Eudragit® can also be used in the formulations, e.g., Eudragit® E (either E 100 or E PO) or the product methyl methacrylate and diethylaminoethyl methacrylate copolymer dispersion sold under the trademark Kollicoat® Smart-Seal. In some embodiments, a method of making the secnidazole microgranule formulation comprises blending with talc. In some embodiments, blending with talc increases the flowability of the secnidazole microgranule formulation.

Some embodiments are directed to a method of manufacturing a plurality of microgranules comprising a nitroimidazole compound, such as secnidazole. In some embodiments, the method of manufacturing a plurality of microgranules comprises forming a plurality of microgranule cores. In some embodiments, forming a plurality of microgranule cores comprises a wet granulation step. In some embodiments, the wet granulation step comprises mixing a nitroimidazole compound with one or more polymers to form a mixture, and hydrating the mixture to form a hydrated mixture. In some embodiments, hydrating the mixture comprises the addition of water to the mixture. In some embodiments, the wet granulation step is carried out in a planetary mixer or high shear granulator.

In some embodiments, forming a plurality of microgranules cores further comprises an extrusion step. In some embodiments, the hydrated mixture is passed through an extruder to form a plurality of extruded microgranule cores. In some embodiments, the hydrated mixture is passed through an extruder (such as a Niro Extruder) fitted with a 0.8 mm screen to form a plurality of extruded microgranule cores.

In some embodiments, forming a plurality of microgranule cores further comprises a spheronization step to form a plurality of spheronized microgranule cores. In some embodiments, the extruded microgranule cores are spheronized to form a plurality of spheronized microgranule cores. In some embodiments, the spheronization step is carried out using a spheronizer (such as a Niro Spheronizer).

In some embodiments, forming a plurality of microgranule cores further comprise drying and screening the plurality of spheronized microgranule cores, In some embodiments, the plurality of spheronized microgranule cores is dried using a Glatt fluid bed and screened to remove fine and oversize material to form a plurality of microgranule cores.

In some embodiments, the method of manufacturing a plurality of microgranules comprises coating the plurality of microgranule cores to form a plurality of coated microgranules. In some embodiments, coating the plurality of microgranule cores comprises coating the plurality of microgranule cores comprises coating the plurality of microgranule cores with one or more polymers. In some embodiments, the one or more polymers can be, but not limited to, PEG (such as PEG 4000), Eudragit® (such as the product ethyl acrylate-methyl methacrylate copolymer sold under the trademark Eudragit® NE30D), talc or a combination thereof, wherein the one or more polymers is sprayed on the plurality of microgranule cores using a Glatt fluid bed to form a plurality of coated microgranules.

In some embodiments, the method of manufacturing a plurality of microgranules further comprises drying and screening the plurality of coated microgranules. In some embodiments, the plurality of coated microgranules are dried in a Glatt fluid bed and screened to remove fine and oversize material.

In some embodiments, the method of manufacturing a plurality of microgranules further comprises blending and curing the plurality of coated microgranules. In some embodiments, blending and curing the plurality of coated microgranules comprises bending the plurality of coated microgranules with talc in a V-blender and curing in a tray dryer at 40° C. for 24 hours.

In some embodiments, administering a therapeutically effective amount of secnidazole to a subject comprises administering a secnidazole or a pharmaceutically acceptable salt thereof in a controlled release form to the subject. In some embodiments, the coating described herein can delay disintegration and absorption in the gastrointestinal tract and thereby providing a controlled and/or sustained action over a longer period than an immediate release composition. Additionally, such coatings can be adapted for release of a secnidazole in a predetermined pattern (e.g., in order to achieve a controlled release composition) or it can be adapted not to release the active compound until after passage of the stomach (enteric coating). Suitable coatings encompassed by such embodiments may include, but are not limited to, sugar coating, film coating (e.g., but not limited to, hydroxypropyl methylcellulose, methylcellulose, methyl hydroxyethyl cellulose, hydroxypropyl cellulose, carboxymethylcellulose, acrylate copolymers, polyethylene glycols, polyvinylpyrrolidone or a combination thereof), or an enteric coating (e.g., but not limited to, methacrylic acid copolymer, cellulose acetate phthalate, hydroxypropylmethylcellulose phthalate, hydroxypropyl methylcellulose acetate succinate, polyvinyl acetate phthalate, shellac, ethyl cellulose or a combination thereof). Furthermore, a time delay material such as, but not limited to, glyceryl monostearate or glyceryl distearate can be incorporated into the coatings of some embodiments. In still other embodiments, the coating can be adapted to protect the composition from unwanted chemical changes, for example, but not limited to, to reduce chemical degradation prior to the release of API.

In some embodiments, multiple doses may be given at pre-determined intervals such as but not limited to once a week, bi-weekly, monthly, bimonthly for the duration of treatment. In some embodiment, the duration of treatment may be at least one week. In some embodiment, the duration of treatment may be at least one month. In some embodiments, the duration of treatment is about six months.

Some embodiments are directed to a method of reducing the incidence and/or risk of a preterm birth. Trichomoniasis or *T. vaginalis* infection may increase the risk of a preterm birth in a subject. In some embodiments, a method of reducing the incidence and/or risk of a preterm birth in a subject comprises administering to the subject a therapeutically effective amount of secnidazole or a pharmaceutically acceptable salt thereof. In some embodiments, a method of reducing the incidence and/or risk of a preterm birth in a subject in need thereof, the method comprising administering to the subject a therapeutically effective amount of secnidazole or a pharmaceutically acceptable salt thereof in a microgranule formulation. In some embodiments, the secnidazole or the pharmaceutically acceptable salt thereof in the microgranule formulation is administered orally. In some embodiments, the secnidazole or the pharmaceutically acceptable salt thereof in the microgranule formulation comprises a plurality of microgranules. In some embodiments, each microgranule comprises an inactive core (such as a sugar core, microcrystalline cellulose core or any core that does not contain any API) and a layer outside of the inactive core. In some embodiments, the layer outside of the inactive core comprises secnidazole. In some embodiments, each microgranule further comprises a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, wherein the therapeutically effective amount of secnidazole is an amount of secnidazole that exhibits a $C_{max}$ of secnidazole in the subject of about 17.4 µg/ml and about 26.5 µg/ml, or about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the secnidazole in a microgranule formulation may be mixed, stirred, or otherwise integrated into a food substance. In some embodiments, the food substance includes, but not limited to, a liquid, semi-solid, or soft food. In some embodiments, the food substance may include, but not limited to, applesauce, yogurt, pudding or the like. In some embodiments, integration of the secnidazole microgranule formulation into a food substance has a taste masking function. In some embodiments, the method of reducing the incidence and/or risk of a preterm birth in a subject in need thereof, the method comprising administering to the subject a microgranule formulation comprising a therapeutically effective amount of nitroimidazole compound (such as secnidazole) or a pharmaceutically acceptable salt thereof, wherein the microgranule formulation comprises a plurality of microgranules, wherein each microgranule comprises a core and a coating, wherein the core comprises the nitroimidazole compound or the pharmaceutically acceptable salt thereof, and wherein the coating surrounds the core. In some embodiments, the nitroimidazole compound is secnidazole, wherein secnidazole comprises at least 70% of the core by weight.

In some embodiments, the secnidazole comprises about 1 gram to about 6 grams of the microgranule formulation. In some embodiments, the secnidazole microgranule formulation is co-administered with an additional compound selected from EE2, NET, or a combination thereof. In some embodiments, the additional compound is administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound. In some embodiments, the amount of the food substance is about 4-6 ounces.

In some embodiments, a method of reducing the incidence and/or risk of a preterm birth in a subject further comprises a term birth. In some embodiments, a method of reducing the incidence and/or risk of a preterm birth in a subject further comprises determining a post-treatment clinical outcome. In some embodiments, a post-treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative *T. vaginalis* test, a negative KOH Whiff test, and clue cells less than or equal to 20% of the total epithelial cells on microscopic examination of a vaginal saline wet mount after treatment with a microgranule formulation comprising about 1 gram to about 6 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2-gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2-gram single dose of secnidazole. In some embodiments, a post-treatment clinical outcome is observable after about 24 hours, about 48 hours, about 72 hours, about 96 hours, about 120 hours, about 168 hours after administration to the subject. In some embodiments, a post-treatment clinical outcome is observable after about 7 days to about 10 days, about 11 days to about 20 days or about 21 days to about 30 days after administration to the subject.

In some embodiments, a method of reducing the incidence and/or risk of a preterm birth in a subject further comprises an alleviation of one or more symptoms of trichomoniasis or *T. vaginalis* infection within up to about three days after administration to the subject. In some embodiments, a method of treating trichomoniasis or *T. vaginalis* infection further comprises an alleviation of one or more symptoms of trichomoniasis or *T. vaginalis* infection within up to about three days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, alleviation refers to a lessening of the severity of one or more symptoms. In some embodiments, alleviation of one or more symptoms of trichomoniasis or *T. vaginalis* infection occurs within about 24 hours, about 48 hours, about 72 hours, about 96 hours, about 120 hours, about 144 hours or about 168 hours after administration to the subject. In some embodiments, alleviation of one or more symptoms of trichomoniasis or *T. vaginalis* infection occurs within about 7 days to about 10 days, about 11 days to about 20 days or about 21 days to about 30 days after administration to the subject.

In some embodiments, a method of reducing the incidence and/or risk of a preterm birth in a subject further comprises a resolution of one or more symptoms of trichomoniasis or *T. vaginalis* infection within up to about seven days after administration to the subject. In some embodiments, a method of treating trichomoniasis or *T. vaginalis* infection further comprises a resolution of one or more symptoms of trichomoniasis or *T. vaginalis* infection within up to about seven days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, resolution of one or more symptoms of trichomoniasis or *T. vaginalis* infection occurs within about 24 hours, about 48 hours, about 72 hours, about 96 hours, about 120 hours, or 144 hours or about 168 hours after administration to the subject. In some embodiments, resolution of one or more symptoms of trichomoniasis or *T. vaginalis* infection occurs within about 7 days to about 10 days, about 11 days to about 20 days or about 21 days to about 30 days after administration to the subject.

Some embodiments are directed to a method of reducing the incidence and/or risk of a subject transmitting HIV to or acquiring HIV from a sexual partner. *T. vaginalis* infection may increase the risk of a HIV transmission to or acquiring HIV from sexual partner. In some embodiments, a method of reducing the incidence and/or risk of the subject transmitting HIV to or acquiring HIV from a sexual partner comprises administering to the subject or sexual partner a therapeutically effective amount of secnidazole or a pharmaceutically acceptable salt thereof. In some embodiments, a method of reducing the incidence and/or risk of the subject transmitting HIV to or acquiring HIV from a sexual partner, the method comprising administering to the subject or sexual partner a therapeutically effective amount of secnidazole or a pharmaceutically acceptable salt thereof in a microgranule formulation. In some embodiments, the secnidazole or the pharmaceutically acceptable salt thereof in the microgranule formulation is administered orally. In some embodiments, the secnidazole or the pharmaceutically acceptable salt thereof in the microgranule formulation comprises a plurality of microgranules. In some embodiments, each microgranule comprises an inactive core (such as a sugar core, microcrystalline cellulose core or any core that does not contain any API) and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, wherein the therapeutically effective amount of secnidazole is an amount of secnidazole that exhibits a $C_{max}$ of secnidazole in the subject or sexual partner of about 17.4 µg/ml and about 26.5 µg/ml, or about 34.5 m/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject or sexual partner of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject or sexual partner. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit®

NE30D), talc, colloidal silicon dioxide, and a combination thereof. In some embodiments, the method of reducing the incidence and/or risk of a subject transmitting HIV to or acquiring HIV from a sexual partner, the method comprising administering to the subject a microgranule formulation comprising a therapeutically effective amount of nitroimidazole compound (such as secnidazole) or a pharmaceutically acceptable salt thereof, wherein the microgranule formulation comprises a plurality of microgranules, wherein each microgranule comprises a core and a coating, wherein the core comprises the nitroimidazole compound or the pharmaceutically acceptable salt thereof, and wherein the coating surrounds the core. In some embodiments, the nitroimidazole compound is secnidazole, wherein secnidazole comprises at least 70% of the core by weight. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In some embodiments, a method of reducing the incidence and/or risk of a subject transmitting HIV to or acquiring HIV from a sexual partner comprises administering to the subject a single dose of a therapeutically effective amount of secnidazole in a microgranule formulation, wherein the secnidazole comprises about 1 gram to about 6 grams of the microgranule formulation. In some embodiments, the secnidazole microgranule formulation is co-administered with an additional compound selected from EE2, NET, or a combination thereof. In some embodiments, the additional compound is administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound. In some embodiments, the secnidazole microgranule formulation is mixed into a semisolid or soft food substance, such as but not limited to applesauce yogurt and pudding. In some embodiments, the amount of the food substance is about 4-6 ounces.

In some embodiments, a method of reducing the incidence and/or risk of a subject transmitting HIV to or acquiring HIV from a sexual partner further comprises the absence of HIV transmission. In some embodiments, a method of reducing the incidence and/or risk of a subject transmitting HIV to or acquiring HIV from a sexual partner further comprises determining a post-treatment clinical outcome. In some embodiments, a post-treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject or sexual partner with normal vaginal discharge, a negative KOH Whiff test, and clue cells less than or equal to 20% of the total epithelial cells on microscopic examination of a vaginal saline wet mount after treatment with a microgranule formulation comprising about 1 gram to about 6 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2-gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2-gram single dose of secnidazole. In some embodiments, a post-treatment clinical outcome is observable after about 24 hours, about 28 hours, about 72 hours, about 96 hours, about 120 hours, about 144 hours or about 168 hours after administration to the subject of sexual partner. In some embodiments, a post-treatment clinical outcome is observable after about 7 days to about 10 days, about 11 days to about 20 days or about 21 days to about 30 after administration to the subject or sexual partner.

In some embodiments, a method of reducing the incidence and/or risk of a subject transmitting HIV to or acquiring HIV from a sexual partner further comprises an alleviation of one or more symptoms of trichomoniasis or *T. vaginalis* infection within up to about three days after administration to the subject or sexual partner. In some embodiments, a method of treating trichomoniasis or *T. vaginalis* infection further comprises an alleviation of one or more symptoms of trichomoniasis or *T. vaginalis* infection within up to about three days after administration to the subject or sexual partner. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, alleviation refers to a lessening of the severity of one or more symptoms. In some embodiments, alleviation of one or more symptoms of trichomoniasis or *T. vaginalis* infection occurs within about 24 hours, about 48 hours, about 72 hours, about 96 hours, about 120 hours, about 144 hours or about 168 hours after administration to the subject or sexual partner. In some embodiments, alleviation of one or more symptoms of trichomoniasis or *T. vaginalis* infection occurs within about 7 days to about 10 days, about 11 days to about 20 days or about 21 days to about 30 days after administration to the subject or sexual partner.

In some embodiments, a method of reducing the incidence and/or risk of a subject transmitting HIV to or acquiring HIV from a sexual partner further comprises a resolution of one or more symptoms of trichomoniasis or *T. vaginalis* infection within up to about seven days after administration to the subject or sexual partner. In some embodiments, a method of treating trichomoniasis or *T. vaginalis* infection further comprises a resolution of one or more symptoms of trichomoniasis or *T. vaginalis* infection within up to about seven days after administration to the subject or sexual partner. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, resolution of one or more symptoms of trichomoniasis or *T. vaginalis* infection occurs within about 24 hours, about 48 hours, about 72 hours, about 96 hours, about 120 hours, about 144 hours or about 168 hours after administration to the subject or sexual partner. In some embodiments, resolution of one or more symptoms of trichomoniasis or *T. vaginalis* infection occurs within about 7 days to about 10 days, about 11 days to about 20 days or about 21 days to about 30 days after administration to the subject or sexual partner.

Some embodiments are directed to a method of reducing the incidence and/or risk of a subject acquiring a STI from or transmitting a STI to a sexual partner. Trichomoniasis or *T. vaginalis* infection may increase the risk of acquiring a STI from or transmitting a STI to a sexual partner. In some embodiments, STIs include, but not limited to, chlamydia, gonorrhea, bacterial vaginosis, herpes simplex virus 2 ("HSV-2") and human papillomavirus ("HPV"). In some embodiments, a method of reducing the incidence and/or risk of the subject acquiring a STI from or transmitting a STI to a sexual partner comprises administering to the subject a therapeutically effective amount of secnidazole or a pharmaceutically acceptable salt thereof. In some embodiments, a method of reducing the incidence and/or risk of subject acquiring a STI from or transmitting a STI to a sexual partner, the method comprising administering to the subject a therapeutically effective amount of secnidazole or a pharmaceutically acceptable salt thereof in a microgranule formulation. In some embodiments, the secnidazole or the pharmaceutically acceptable salt thereof in the microgranule formulation is administered orally. In some embodiments, the secnidazole or the pharmaceutically acceptable salt thereof in the microgranule formulation comprises a plurality of microgranules. In some embodiments, each microgranule comprises an inactive core (such as a sugar core, microcrystalline cellulose core or any core that does not contain any API) and a layer outside of the inactive core. In some embodiments, the layer outside of the inactive core comprises secnidazole. In some embodiments, each microgranule further comprises as a coating layer that is outside of the layer outside of the inactive core. In some embodiments, the coating layer comprises a delayed release element (such as ethyl acrylate-methyl methacrylate copolymer) and/or an anti-tacking element (such as glycerol monostearate). In some embodiments, the plurality of microgranules has a particle size diameter in the range of about 400 micrometers to about 841 micrometers. In some embodiments, the particle size diameter of the microgranule is measured using laser diffraction. In some embodiments, wherein the therapeutically effective amount of secnidazole is an amount of secnidazole that exhibits a $C_{max}$ of secnidazole in the subject of about 17.4 µg/ml and about 26.5 µg/ml, about 34.5 µg/ml to about 58.3 µg/ml, or about 26 µg/ml to about 34 µg/ml, or about 26 µg/ml to about 58 µg/ml. In some embodiments, wherein the therapeutically effective amount of secnidazole is an amount of secnidazole that exhibits a $T_{max}$ of secnidazole in the subject of about 2 hours to about 6 hours, or about 3 hours to about 4 hours, or about 6 hours to about 24 hours, or about 2 hours to about 24 hours. In some embodiments, wherein the therapeutically effective amount of secnidazole is an amount of secnidazole that exhibits a $t_{1/2}$ of about 11 hours to about 20 hours in the subject. In some embodiments, wherein secnidazole is the sole drug in the microgranule formulation. In some embodiments, the secnidazole microgranule formulation further comprises one or more of the following ingredients selected from at least one inert core (sugar spheres being preferred); at least one binding agent (povidone being preferred); at least one plasticizer (polyethylene glycol being preferred, and polyethylene glycol 4000 being most preferred); at least one film-forming polymer (poly(meth)acrylates being preferred and ethyl acrylate-methyl methacrylate copolymer being most preferred), at least one anti-tacking agent (talc being preferred); at least one anti-static agent (talc being preferred); and a combination thereof. In some embodiments, the microgranule formulation further comprises at least one compound selected from the group consisting of sugar spheres, povidone, polyethylene glycol (such as polyethylene glycol 4000), ethyl acrylate-methyl methacrylate copolymer (such as the product ethyl acrylate-methyl methacrylate copolymer sold under the trademark Eudragit® NE30D), talc, colloidal silicon dioxide, and a combination thereof. In some embodiments, the method of reducing the incidence and/or risk of the subject acquiring a STI from or transmitting a STI to a sexual partner comprises administering to the subject a microgranule formulation comprising a therapeutically effective amount of nitroimidazole compound (such as secnidazole) or a pharmaceutically acceptable salt thereof, wherein the microgranule formulation comprises a plurality of microgranules, wherein each microgranule comprises a core and a coating, wherein the core comprises the nitroimidazole compound or the pharmaceutically acceptable salt thereof, and wherein the coating surrounds the core. In some embodiments, the nitroimidazole compound is secnidazole, wherein secnidazole comprises at least 70% of the core by weight. In some embodiments, the secnidazole in a microgranule formulation may be mixed, stirred, or otherwise integrated into a food substance. In some embodiments, the food substance includes, but not limited to, a liquid, semisolid, or soft food. In some embodiments, the food substance may include, but not limited to, applesauce, yogurt, pudding or the like. In some embodiments, integration of the secnidazole microgranule formulation into a food substance has a taste masking function.

In some embodiments, a method of reducing the incidence and/or risk of a subject acquiring a STI from or transmitting a STI to a sexual partner comprises administering to the subject a single dose of a therapeutically effective amount of secnidazole in a microgranule formulation, wherein the secnidazole comprises about 1 gram to about 6 grams of the microgranule formulation. In some embodiments, the secnidazole microgranule formulation is co-administered with an additional compound selected from EE2, NET, or a combination thereof. In some embodiments, the additional compound is administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound. In some embodiments, the secnidazole microgranule formulation is mixed into a semisolid or soft food substance, such as but not limited to applesauce yogurt and pudding. In some embodiments, the amount of the food substance is about 4-6 ounces.

In some embodiments, a method of reducing the incidence and/or risk of a subject acquiring a STI from or transmitting a STI to a sexual partner further comprises the absence of an STI transmission or acquisition of an STI by the subject. In some embodiments, a method of reducing the incidence and/or risk of a subject acquiring an STI from a sexual partner further comprises determining a post-treatment clinical outcome. In some embodiments, a post-treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with a microgranule formulation comprising about 1 gram to about 6 grams of secnidazole. In some embodiments, a clinical outcome responder has a gram stain slide Nugent score of less than four (4) after treatment with a single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of secnidazole. In some embodiments, a clinical outcome responder has a gram stain slide Nugent score of less than four (4) after treatment with a 2-gram single dose of secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a 2-gram single dose of secnidazole. In some embodiments, a post-treatment clinical outcome is observable after about 24 hours, about 48 hours, about 72 hours, about 96 hours, about 120 hours, about 144 hours or about 168 hours after administration to the subject. In some embodiments, a post-treatment clinical outcome is observable after about 7 to about 10 days, about 11 to about 20 days or about 21 to about 30 days after administration to the subject.

In some embodiments, a method of reducing the incidence and/or risk of a subject acquiring a STI from or transmitting a STI to a sexual partner further comprises an alleviation of one or more symptoms of trichomoniasis or *T. vaginalis* infection within up to about three days after administration to the subject. In some embodiments, a method of treating trichomoniasis or *T. vaginalis* infection further comprises an alleviation of one or more symptoms of trichomoniasis or *T. vaginalis* infection within up to about three days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, alleviation refers to a lessening of the severity of one or more symptoms. In some embodiments, alleviation of one or more symptoms of trichomoniasis or *T. vaginalis* infection occurs within about 24 hours, about 48 hours, about 72 hours, about 96 hours, about 120 hours, about 144 hours or about 168 hours after administration to the subject. In some embodiments, alleviation of one or more symptoms of trichomoniasis or *T. vaginalis* infection occurs within about 7 days to about 10 days, about 11 days to about 20 days or about 21 days to about 30 days after administration to the subject.

In some embodiments, a method of reducing the incidence and/or risk of a subject acquiring a STI from or transmitting a STI to a sexual partner further comprises a resolution of one or more symptoms of trichomoniasis or *T. vaginalis* infection within up to about seven days after administration to the subject. In some embodiments, a method of treating trichomoniasis or *T. vaginalis* infection further comprises a resolution of one or more symptoms of trichomoniasis or *T. vaginalis* infection within up to about seven days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, resolution of one or more symptoms of trichomoniasis or *T. vaginalis* infection occurs within about 24 hours, about 48 hours, about 72 hours, about 96 hours, about 120 hours, about 144 hours or about 168 hours after administration to the subject or sexual partner. In some embodiments, resolution of one or more symptoms of trichomoniasis or *T. vaginalis* infection occurs within about 7 days to about 10 days, about 11 days to about 20 days or about 21 days to about 30 days after administration to the subject or sexual partner.

In some embodiments, a method of reducing the incidence and/or risk of a subject acquiring a STI from or transmitting a STI to a sexual partner comprises administering to the subject a single dose of a therapeutically effective amount of secnidazole in a microgranule formulation, wherein the secnidazole comprises about 1 gram to about 6 grams of the microgranule formulation. In some embodiments, the secnidazole microgranule formulation is co-administered with an additional compound selected from EE2, NET, or a combination thereof. In some embodiments, the additional compound is administered on the same day as the secnidazole microgranule formulation. In some embodiments, the additional compound is administered on a different day than the secnidazole microgranule formulation. In some embodiments, the secnidazole microgranule formulation does not affect the contraceptive efficacy of the additional compound. In some embodiments, the secnidazole microgranule formulation is mixed into a semisolid or soft food substance, such as but not limited to applesauce, yogurt, and pudding. In some embodiments, the amount of the food substance is about 4-6 ounces.

In some embodiments, a method of treating trichomoniasis or *T. vaginalis* infection in a subject further comprises determining a post-treatment clinical outcome. In some embodiments, a post-treatment clinical outcome is indicative of a clinical outcome responder. In some embodiments, a clinical outcome responder is a subject that is asymptomatic. In some embodiments, a post-treatment clinical outcome is observable after about 24 hours, about 48 hours, about 72 hours, about 96 hours, about 120 hours, about 144 hours or about 168 hours after administration to the subject. In some embodiments, a post-treatment clinical outcome is observable after about 7 days to about 10 days, about 11 to about 20 days or about 21 to about 30 days after administration to the subject.

In some embodiments, a method of treating trichomoniasis or *T. vaginalis* infection further comprises an alleviation of one or more symptoms of trichomoniasis within up to about three days after administration to the subject. In some embodiments, a method of treating trichomoniasis or *T. vaginalis* infection further comprises an alleviation of one or more symptoms of trichomoniasis or *T. vaginalis* infection within up to about three days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, alleviation refers to a lessening of the severity of one or more symptoms. In some embodiments, alleviation of one or more symptoms of trichomoniasis or *T. vaginalis* infection occurs within about 24 hours, about 48 hours, about 72 hours, about 96 hours, about 120 hours, about 168 hours after administration to the subject. In some embodiments, alleviation of one or more symptoms of trichomoniasis or *T. vaginalis* infection occurs within about 7 to about 10 days, about 11 to about 20 days or about 21 to about 30 days after administration to the subject.

In some embodiments, a method of treating trichomoniasis or *T. vaginalis* infection further comprises a resolution of one or more symptoms of trichomoniasis or *T. vaginalis* infection within up to about seven days after administration to the subject. In some embodiments, a method of treating trichomoniasis or *T. vaginalis* infection further comprises a resolution of one or more symptoms of trichomoniasis or *T. vaginalis* infection within up to about seven days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, resolution of one or more symptoms of trichomoniasis occurs within about 24 hours, about 48 hours, about 72 hours, about 96 hours, about 120 hours, about 144 hours or about 168 hours after administration to the subject. In some embodiments, resolution of one or more symptoms of trichomoniasis occurs within about 48 hours after administration. In some embodiments, resolution of one or more symptoms of trichomoniasis or *T. vaginalis* infection occurs within about 7 to about 10 days, about 11 to about 20 days or about 21 to about 30 days after administration to the subject.

In some embodiments, treatment of trichomoniasis or *T. vaginalis* infection with a single, 2-gram dose of secnidazole in a microgranule formulation results in better than expected efficacy compared with FDA-approved drugs used in the treatment of trichomoniasis or *T. vaginalis* infection. In some embodiments, a single dose of 2 grams of secnidazole results in a better than expected efficacy compared with FDA-approved drugs currently used in the treatment of trichomoniasis or *T. vaginalis* infection. In some embodiments, treatment of trichomoniasis or *T. vaginalis* infection with a single, 2-gram dose of secnidazole results in superior efficacy compared with FDA-approved drugs used in the treatment of trichomoniasis or *T. vaginalis* infection. In some embodiments, a single dose of 2 grams of secnidazole results in superior efficacy compared with FDA drugs used in the treatment of trichomoniasis or *T. vaginalis* infection requiring a single dose during treatment.

In some embodiments, treatment of trichomoniasis or *T. vaginalis* infection with a single, 2-gram dose of secnidazole results in a better than expected safety profile compared with FDA-approved drugs used in the treatment of trichomoniasis or *T. vaginalis* infection. In some embodiments, a single dose of 2 grams of secnidazole results in a better than expected safety profile compared with FDA-approved drugs used in the treatment of trichomoniasis or *T. vaginalis* infection requiring multiple doses during treatment. In some embodiments, treatment of trichomoniasis or *T. vaginalis* infection with a single, 2-gram dose of secnidazole results in a superior safety profile compared with FDA-approved drugs used in the treatment of trichomoniasis or *T. vaginalis* infection. In some embodiments, a single dose of 2 grams of secnidazole results in a superior safety profile compared with FDA-approved drugs used in the treatment of trichomoniasis r or *T. vaginalis* infection requiring a single dose during treatment.

In some embodiments, a method of treating trichomoniasis in a subject in need thereof, the method comprising the steps of:
  (a) confirming the subject has trichomoniasis by a trichomoniasis diagnostic test;
  (b) administering to the subject the single oral dose of SYM-1219 (microgranule formulation of 2 grams of secnidazole); and
  (c) within 6 days to 12 days after step (b), evaluating the subject for a primary endpoint of microbiological cure.

In some embodiments, the trichomoniasis diagnostic test includes, but not limited to, a nucleic acid amplification test; a DNA hybridization probe test (such as the BD Affirm™ VPIII Microbial Identification System from Becton Dickinson in Sparks, MD, USA); a multiplex PCR panel test (such as BD MAX™ CT/GC/TV Assay using the BD MAX™ System from Becton Dickinson in Sparks, MD, USA); an antigen-detection test (such as OSOM® *Trichomonas* Rapid Test from Sekisui Diagnostics in Framingham, MA, USA); a *T. vaginalis* culture; a wet mount test; a trichomoniasis diagnostic test using broth culture technique (such as the InPouch® TV test from BioMed Diagnostics, Inc. in White City, OR, USA); or a combination thereof. In some embodiments, the trichomoniasis diagnostic test requires a vaginal sample, an endocervical sample, a urine sample, a vaginal swab, a urethral swab, a penile-meatal swab, or a combination thereof from the subject. In some embodiments, the primary endpoint of microbiological cure is a negative *T. vaginalis* culture, a negative nucleic acid amplification test result, a negative DNA hybridization probe test result, a negative multiplex PCR panel test result, a negative antigen-detection test result, a negative wet mount test result, or a combination thereof. In some embodiments, the subject also has bacterial vaginosis, is HIV-positive, or a combination thereof. In some embodiments, the rate of the primary endpoint of microbiological cure is at least 0.5%, at least 2%, at least 10%, at least 50%, at least 90%, at least 92%, at least 95%, or at 100%.

In some embodiments, a method of treating trichomoniasis in a subject in need thereof, the method comprising the steps of:
- (a) confirming the subject has trichomoniasis by positive *T. vaginalis* culture;
- (b) randomizing whether the subject receives a single oral dose of SYM-1219 (microgranule formulation of 2 grams of secnidazole) or a placebo;
- (c) administering to the subject the single oral dose of SYM-1219 (microgranule formulation of 2 grams of secnidazole) or the placebo;
- (d) within 6 days to 12 days after step (c), evaluating the subject for a primary endpoint of microbiological cure;
- (e) administering the opposite treatment of step (c) to the subject; and
- (f) discharging the subject from treatment if the subject shows negative *T. vaginalis* culture.

In some embodiments, the method further comprises the step of, within 7 days to 12 days after step (e), assessing the subject with positive *T. vaginalis* culture obtained in step (d) for the primary endpoint of microbiological cure. In some embodiments, the primary endpoint of microbiological cure is a negative *T. vaginalis* culture. In some embodiments, the rate of primary endpoint of microbiological cure is higher in the single oral dose of SYM-1219 group than the placebo group. In some embodiments, the subject also has bacterial vaginosis, is HIV-positive, or a combination thereof. In some embodiments, the rate of the primary endpoint of microbiological cure is at least 0.5%, at least 2%, at least 10%, at least 50%, at least 90%, at least 92%, at least 95%, or at 100%.

In some embodiments, the method includes wherein the positive or negative *T. vaginalis* culture is determined by a trichomoniasis diagnostic test using broth culture technique (such as the InPouch® TV test).

In some embodiments, a method of treating trichomoniasis in subjects in need thereof, the method comprising the steps of:
- (a) confirming the diagnosis of trichomoniasis by a positive *T. vaginalis* culture result in each subject (which is Visit 1);
- (b) randomizing (1:1) the subjects to receive either a single oral dose of SYM-1219 (formulation of 2 grams of secnidazole) or a placebo, and administering to each subject the single oral dose of SYM-1219 (formulation of 2 grams of secnidazole) or the placebo based on randomization;
- (c) evaluating each subject 6 days to 12 days after step (b) (which is Visit 2) for a primary endpoint of microbiological cure (which is a Test of Cure ("TOC") at Visit 2);
- (d) administering to each subject at Visit 2 the opposite treatment received at step (b);
- (e) discharging the subjects from treatment who have a negative *T. vaginalis* culture result obtained in step (c); and
- (f) assessing the remaining subjects 7 days to 12 days after step (d) (which is Visit 3) for the primary endpoint of microbiological cure, wherein the remaining subjects had a positive *T. vaginalis* culture result obtained in step (c).

In some embodiments, the primary endpoint of microbiological cure is a negative *T. vaginalis* culture. In some embodiments, the rate of primary endpoint of microbiological cure is higher in the single oral dose of SYM-1219 group than the placebo group. In some embodiments, the rate of primary endpoint of microbiological cure at step (c) is higher in the single oral dose of SYM-1219 group than the placebo group. In some embodiments, the subjects comprise subjects also having bacterial vaginosis, are HIV-positive or a combination thereof. In some embodiments, the subjects are in a modified intent-to-treat ("mITT") population. In some embodiments, the rate of primary endpoint of microbiological cure in the mITT population at step (c) is higher in the single oral dose of SYM-1219 group than the placebo group.

In some embodiments, the mITT population includes all randomized patients who are culture positive for *T. vaginalis* and negative for other sexually transmitted infections. In some embodiments, the rate of primary endpoint of microbiological cure in the mITT population at step (c) is at least about 0.5%, about 2%, about 10%, about 50%, about 90%, about 92%, or about 95%. In some embodiments, the rate of primary endpoint of microbiological cure in the mITT population at step (c) is in the range of at least about 0.5% (or about 2%, or about 10%, or about 50%, or about 90%, or about 92%) to about 95%; at least about 0.5% to about 2%; at least about 0.5% (or about 2%) to about 10%; at least about 0.5% (or about 2%, or about 10%) to about 50%; at least about 0.5% (or about 2%, or about 10%, or about 50%) to about 90%; or at least about 0.5% (or about 2%, or about 10%, or about 50%, or about 90%) to about 92%.

In some embodiments, the subjects comprise subjects are HIV-positive. In some embodiments, the rate of primary endpoint of microbiological cure in the mITT population at step (c) is at least about 0.5%, about 10%, about 50%, about 90%, or about 100%. In some embodiments, the rate of primary endpoint of microbiological cure in the mITT population at step (c) is in the range of at least about 0.5% (or about 10%, or about 50%, or about 90%) to about 100%; at least 0.5% to about 10%; or at least 0.5% (or about 10% or about 50%) to about 90%.

In some embodiments, further comprising a treatment delay for the subjects originally randomized to a placebo.

In some embodiments, the sexual partner of the subject is a male or a female.

This invention and embodiments illustrating the method and materials used may be further understood by reference to the following non-limiting examples.

EXAMPLES

Example 1—Safety and Pharmacokinetics of SYM-1219

This study evaluated the safety and pharmacokinetics (PK) of a 1 g or 2 g dose of a microgranule formulation (formulation shown in Table 1) known as "SYM-1219," which contains a 5-nitroimidazole derivative (secnidazole), being developed for the treatment of women with trichomoniasis or *T. vaginalis* infection.

TABLE 1

Composition of SYM-1219 Drug Product

| Component | Function | Quality Standard | Quantity, mg/1 g Dose | Quantity, mg/2 g Dose |
|---|---|---|---|---|
| Secnidazole | Active Ingredient | Manufacturer's specifications | 1000.00 | 2000.00 |
| Sugar Spheres (size 35-40 mesh) | Inert core | National Formulary ("NF") | 940.00 | 1880.00 |
| Povidone (Plasdone ™ K-29/32) | Dispersion and binding | United States Pharmacopeia ("USP") | 100.82 | 201.63 |
| Polyethylene Glycol 4000 | Seal coating | NF | 41.50 | 83.00 |
| Eudragit ® NE30D (Ethyl Acrylate-Methyl Methacrylate Copolymer) | Delayed release coating | NF | 138.30 | 273.60 |
| Talc | Anti-tacking agent | USP | 138.30 | 273.60 |
| Total | | | 2365.00 | 4730.00 |

Methods: 28 healthy female subjects (14/group) ages 18-65 years were randomized to receive a single oral dose of SYM-1219 (1 g or 2 g), mixed into 4 oz. of applesauce. Serial blood samples were collected over 168 hours to determine SYM-1219 plasma concentrations. A non-compartmental analysis was performed and the PK parameters for each treatment group are reported. Safety was evaluated by recording adverse events, vital signs, ECGs and laboratory tests.

The pharmacokinetics and safety of a single oral dose of SYM-1219 (1 g or 2 g) were evaluated. Of the 28 healthy adult female subjects who participated in the studies, 14 received a single dose of SYM-1219 1-gram and the other 14 received a single dose of SYM-1219 2-gram. Serial plasma samples were collected for the assessment of secnidazole pharmacokinetics over 168 hours after dosing from each subject. Blood was obtained for determination of SYM-1219 plasma concentrations at the following times: pre-dose (within 30 minutes of dosing), and then at 0.25 hour, 0.5 hour, 1 hour, 1.5 hours, 2 hours, 3 hours, 4 hours, 6 hours, 8 hours, 10 hours, 12 hours, 16 hours, 18 hours, 24 hours, 36 hours, 48 hours, 72 hours, 96 hours, 120 hours, 144 hours, and 168 hours post-dose.

Plasma concentrations of SYM-1219 were determined by using validated analytical procedures. The following plasma pharmacokinetic parameters were determined for secnidazole via noncompartmental analysis methods: $C_{max}$, $T_{max}$, area under the plasma concentration curve from time 0 to the last timepoint ("$AUC_{0-t}$"), area under the plasma concentration curve from time 0 extrapolated to infinity ("$AUC_{0-inf}$"), half-life ("$t_{1/2}$") and apparent terminal rate constant ($\lambda_z$).

Figure 1:
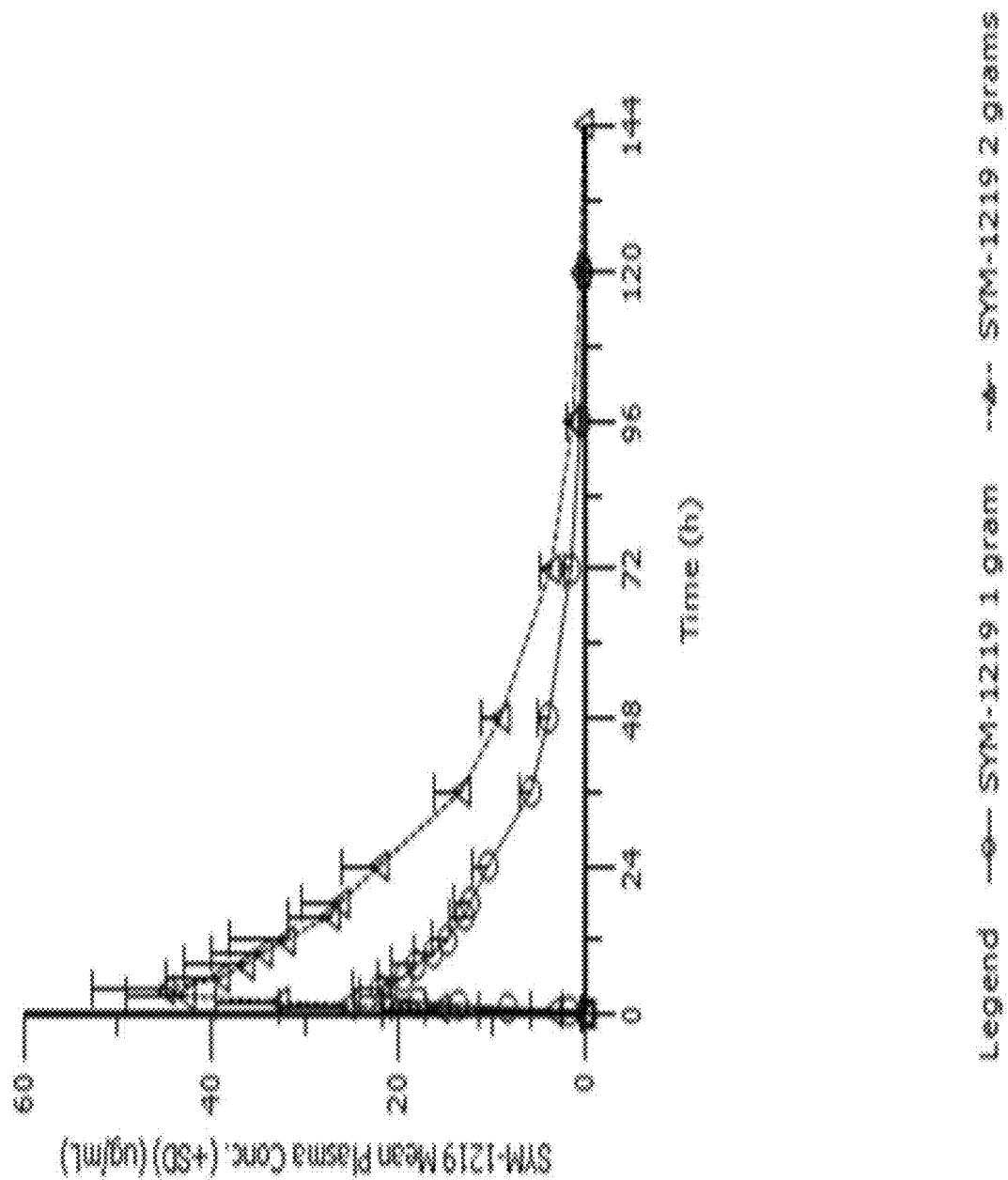
FIG. 1 illustrates the mean standard deviation ("(±SD)") SYM-1219 plasma concentration (µg/mL) for the 1 g dose (circle markers) and the 2 g dose (triangle markers) over time.

Mean (±SD) plasma concentrations of secnidazole by dose and time point are displayed graphically in FIG. 1, which illustrates the mean (±SD) SYM-1219 plasma concentration for the 1-gram dose and the 2-grams dose over time. The time points plotted in FIG. 1 correspond to the sample collection times described above, i.e., pre-dose (within 30 minutes of dosing), and then at 0.25 hour, 0.5 hour, 1 hour, 1.5 hours, 2 hours, 3 hours, 4 hours, 6 hours, 8 hours, 10 hours, 12 hours, 16 hours, 18 hours, 24 hours, 36 hours, 48 hours, 72 hours, 96 hours, 120 hours, 144 hours, and 168 hours post-dose. Descriptive statistics and secnidazole plasma pharmacokinetic parameters by dose are provided in Table 2 below.

The experimental methods described above are based on the FDA's Guidance for Industry—Bioavailability and Bioequivalence Studies Submitted in NDAs or INDs—General Considerations, March 2014 ("FDA's Guidance for Industry"). For example, the FDA's Guidance for Industry recommends using blood samples and measuring in serum or plasma. Here, blood samples were collected from each subject and SYM-1219 plasma concentrations were determined. In addition, the FDA's Guidance for Industry recommends, at a minimum, 12 to 18 samples be collected per subject per dose. Here, 22 samples from each subject including a pre-dose were collected, which is more than the recommended minimum number of samples. Further, the FDA's Guidance for Industry recommends that the sample collection should be spaced in such a way that the $C_{max}$ of the drug in the blood and terminal elimination rate constant ($\lambda_z$) can be estimated accurately. The time intervals for sample collection in the method described above are sufficiently spaced that the $C_{max}$ of SYM-1219 and $\lambda_z$ are estimated with reasonable accuracy.

Results: All subjects (N=28; "N" meaning number of subjects) completed the study and were evaluable for PK and safety. Table 2 below discloses the plasma pharmacokinetics of SYM-1219 (1 g or 2 g) administered according to methods described in this Example to fasted healthy female subjects. Table 4 below discloses the urine pharmacokinetics of SYM-1219 (1 g or 2 g) administered according to methods described in this Example to fasted healthy female subjects. FIG. 1 illustrates the mean (+SD) SYM-1219 plasma concentration (ug/mL) for the 1 g dose (circle markers) and the 2 g dose (triangle markers) over time.

The PK of SYM-1219 was consistent between individuals, as demonstrated by low coefficients of variation ("% CV") estimates. Mean maximum concentrations were 22.6 mcg/mL for the 1 g dose and 45.4 mcg/mL for the 2 g dose and were achieved by approximately 4 hrs. in both dose groups. Exposure estimates ("AUCinf") were 619 mcg*hr./mL for the 1 g dose and 1331 mcg*hr./mL for the 2 g dose. The pharmacokinetics of SYM-1219 was dose proportional when comparing the 1 g and 2 g doses. The intersubject variability was low (<20% CV) for $C_{max}$ and AUC. Urinary excretion of unchanged SYM-1219 accounted for 13.6% (1 g dose) and 15.3% (2 g dose) of the administered dose. The amount excreted into the urine increased in proportion to dose. Renal clearance was similar after 1 g and 2 g doses and the renal clearance is only a small percentage (i.e., <5%) of the glomerular filtration rate typically found in healthy subjects with normal renal function.

SYM-1219 was safe and well-tolerated. The most common adverse events were headache and nausea. All adverse events were mild and resolved without sequelae. There were no significant changes in vital signs, electrocardiogram ("ECG") or laboratory parameters.

TABLE 2

Plasma Pharmacokinetics of SYM-1219 After a Single Oral Dose Administered to Fasted Healthy Female Subjects (Part A) Pharmacokinetic Population

| Parameter | SYM-1219, 1 gram (N = 14) | SYM-1219, 2 grams (N = 14) |
|---|---|---|
| $C_{max}$ (μg/mL) | | |
| n | 14 | 14 |
| Mean (SD) | 22.62 (2.871) | 45.43 (7.642) |
| % CV | 12.69 | 16.82 |
| Geometric Mean (SD) | 22.45 (2.938) | 44.84 (7.467) |
| Median | 22.75 | 45.05 |
| Min, Max | 17.4, 26.5 | 34.5, 58.3 |
| $T_{max}$ (h) | | |
| n | 14 | 14 |
| Median | 3.060 | 4.000 |
| Min, Max | 2.00, 6.00 | 3.00, 4.05 |
| $AUC_{0-t}$ (h*μg/mL) | | |
| n | 14 | 14 |
| Mean (SD) | 609.66 (96.685) | 1322.40 (230.256) |
| % CV | 15.86 | 17.41 |
| Geometric Mean (SD) | 602.94 (92.067) | 1305.35 (214.383) |
| Median | 587.42 | 1290.41 |
| Min, Max | 487.6, 832.5 | 1048.5, 1899.5 |
| $AUC_{0-\infty}$ (h*μg/mL) | | |
| n | 14 | 14 |
| Mean (SD) | 618.89 (98.093) | 1331.63 (230.159) |
| % CV | 15.85 | 17.28 |
| Geometric Mean (SD) | 612.09 (93.248) | 1314.74 (214.081) |
| Median | 595.25 | 1299.10 |
| Min, Max | 498.5, 847.0 | 1055.1, 1911.9 |
| $t_{1/2}$ (h) | | |
| n | 14 | 14 |
| Mean (SD) | 17.05 (1.611) | 16.86 (2.649) |
| Median | 16.79 | 17.13 |
| Min, Max | 14.7, 20.4 | 11.3, 20.4 |
| λz (1/h) | | |
| n | 14 | 14 |
| Mean (SD) | 0.04099 (0.003757) | 0.04220 (0.007544) |
| Median | 0.04129 | 0.04047 |
| Min, Max | 0.0339, 0.0471 | 0.0340, 0.0613 |

Source: Table 14.1.2.4, Listing 16.2.1.11.2

TABLE 3

Urine Pharmacokinetics of SYM-1219 After a Single Oral Dose Administered to Fasted Healthy Female Subjects (Part A) Pharmacokinetic Population

| Parameter | SYM-1219, 1 gram (N = 14) | SYM-1219, 2 grams (N = 14) |
|---|---|---|
| $Ae_{0-168}$ (g) | | |
| n | 14 | 14 |
| Mean (SD) | 0.136 (0.0238) | 0.306 (0.0711) |
| % CV | 17.478 | 23.234 |
| Geometric Mean (SD) | 0.134 (0.0241) | 0.300 (0.0602) |
| Median | 0.140 | 0.299 |
| Min, Max | 0.10, 0.18 | 0.22, 0.52 |
| CLr (mL/min) | | |
| n | 14 | 14 |
| Mean (SD) | 3.742 (0.8255) | 3.935 (1.0568) |
| % CV | 22.060 | 26.859 |
| Geometric Mean (SD) | 3.650 (0.8701) | 3.801 (1.0532) |
| Median | 3.965 | 3.962 |
| Min, Max | 2.37, 4.89 | 2.23, 6.19 |
| % FE | | |
| n | 14 | 14 |
| Mean (SD) | 13.602 (2.3773) | 15.300 (3.5549) |
| % CV | 17.478 | 23.234 |
| Geometric Mean (SD) | 13.403 (2.4100) | 14.991 (3.0081) |
| Median | 13.981 | 14.943 |
| Min, Max | 10.19, 17.56 | 11.03, 26.20 |

Source: Table 14.1.2.5, Listing 16.2.1.12.1

Conclusions: This study characterized the single dose PK of a 1 g and 2 g dose of a new microgranule formulation of a 5-nitroimidazole derivative (secnidazole), SYM-1219. SYM-1219 was safe and well-tolerated. The consistent PK and resulting exposure, with low variability between subjects, makes this a promising new therapeutic option. Ongoing studies will further evaluate the safety and efficacy of SYM-1219 for the treatment of women with trichomoniasis.

Example 2—SYM-1219's Effect on PK of Ethinyl Estradiol (EE2) and Norethindrone (NET)

Background: This study evaluated the effect of a single 2 g dose of SYM-1219, a new microgranule formulation containing a 5-nitroimidazole derivative (secnidazole) in development to treat women with trichomoniasis or *T. vaginalis* infection, on the PK of EE2 and NET.

Methods: Fifty-four (54) healthy female subjects, ages 18-65, received EE2/NET alone and in combination, where SYM-1219+ EE2/NET were co-administered on Day 1 (Group B1; N=27) or SYM-1219 on Day 1 and EE2/NET on Day 2 (Group B2; N=27). Serial blood samples were drawn to measure plasma concentrations of EE2/NET. A non-compartmental analysis was performed and the PK parameters for each treatment group are reported. Safety was evaluated by recording of adverse events, vital signs, ECGs and standard laboratory tests.

Figure 2:
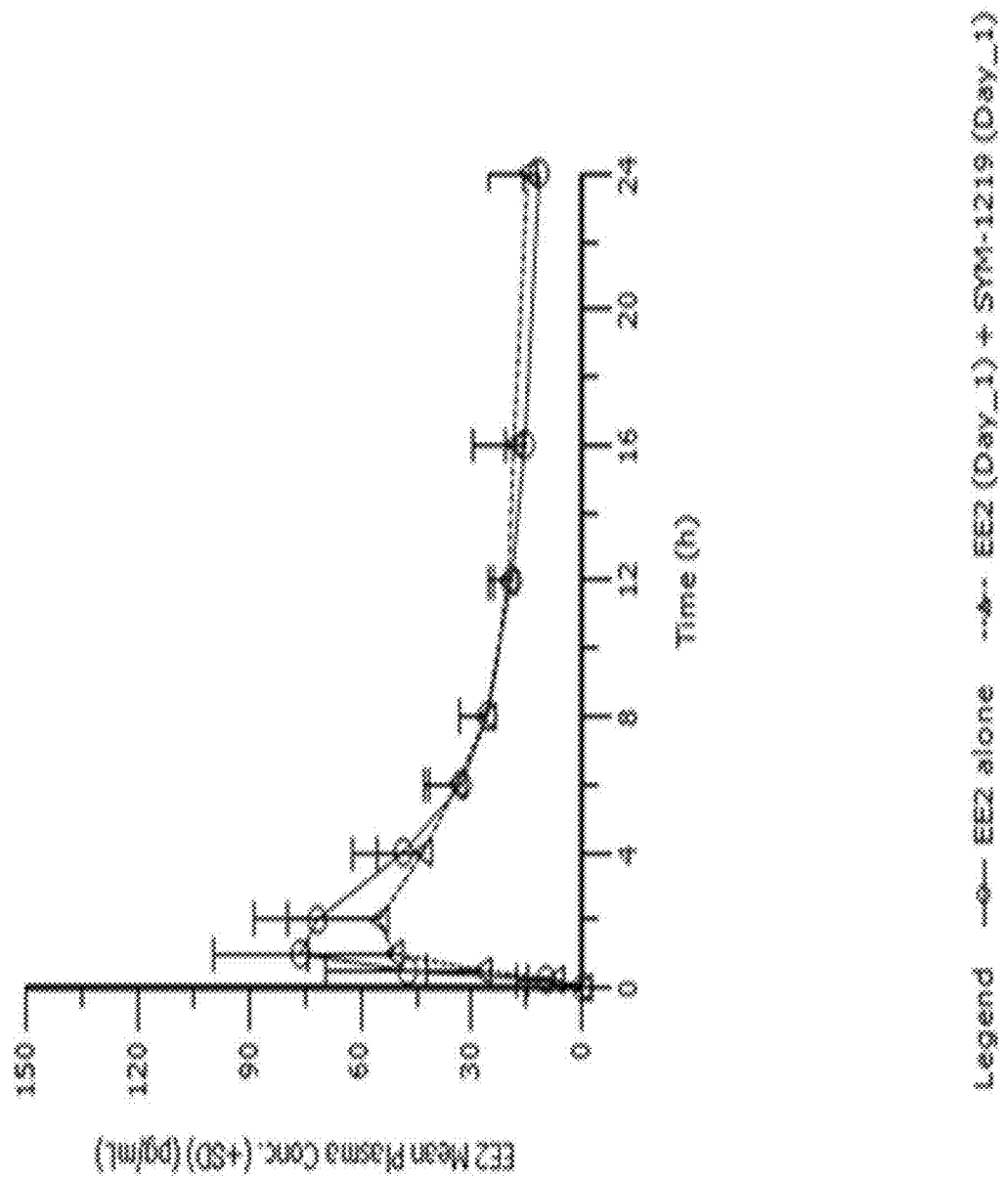
FIG. 2 illustrates the mean (±SD) EE2 plasma concentrations (pg/mL) for Group B1 over time where (1) EE2 was administered alone (circle markers) on Day 1 of Period 1.

Results: Fifty-one (N=26 for B1 and N=25 for B2) subjects completed the study. FIG. 2 illustrates the mean (+SD) EE2 plasma concentrations (pg/mL) over time when EE2 was administered alone (circle markers) on Day 1 of Period 1 and when EE2 was administered in conjunction with 2 grams microgranule formulation SYM-1219 on Day 1 of Period 2 (triangle markers) (Group B1). FIG. 3 illustrates the mean (+SD) EE2 plasma concentrations (pg/mL) over time when (1) EE2 was administered alone (circle markers) on Day 1 of Period 1; and (2) when 2 grams microgranule formulation SYM-1219 was administered on Day 1 of Period 2 and EE2 was administered on Day 2 of Period 2 (triangle markers) (Group B2). FIG. 4 illustrates the mean (+SD) net plasma levels (ng/mL) over time when (1) NET alone was administered on Day 1 of Period 1 (circle markers), and (2) NET followed by 2 grams microgranule formulation of SYM-1219 was administered on Day 1 of Period 2 (triangle markers) (Group B1). FIG. 5 illustrates the mean (+SD) net plasma levels (ng/mL) over time when (1) NET alone was administered on Day 1 of Period 1 (circle markers), and (2) 2 grams microgranule formulation of SYM-1219 was administered on Day 1 of Period 2 and NET was administered on Day 2 of Period 2 (triangle markers) (Group B2). Table 4 below is a summary of the NET plasma pharmacokinetic parameters for Group B1 where (1) EE2/NET was administered on Day 1 of Period 1, and (2) EE2/NET was administered followed by SYM-1219 on Day 1 of Period 2; and Group B2 where (1) EE2/NET were administered on Day 1 of Period 1, and (2) 2 grams microgranule formulation of SYM-1219 was administered followed by on Day 1 of Period 2 and EE2/NET was administered on Day 2 of Period 2. Table 5 below is a summary of the percent of relative bioavailability for EE2 plasma pharmacokinetic parameters $C_{max}$, $AUC_{0-t}$, and $AUC_{0-\infty}$, for Group B1 where (1) EE2/NET was administered on Day 1 of Period 1, and (2) EE2/NET followed by 2 grams microgranule formulation of SYM-1219 was administered on Day 1 of Period 2; and Group B2 where (1) EE2/NET was administered on Day 1 of Period 1, and (2) 2 grams microgranule formulation of SYM-1219 was administered on Day 1 and EE2/NET was administered on Day 2 of Period 2. Table 6 is a summary of the percent of relative bioavailability for NET plasma pharmacokinetic parameters $C_{max}$, $AUC_{0-t}$, and $AUC_{0-\infty}$, for Group B1 where (1) EE2/NET was administered on Day 1 of Period 1, and (2) EE2/NET followed by 2 grams microgranule formulation of SYM-1219 was administered on Day 1 of Period 2; and Group B2 where (1) EE2/NET was administered on Day 1 of Period 1, and (2) 2 grams microgranule formulation of SYM-1219 was administered on Day 1 and EE2/NET was administered on Day 2 of Period 2.

TABLE 4

Summary of NET Plasma Pharmacokinetic Parameters by Period and Treatment-Pharmacokinetic Population (Part B)

| Parameter | Group B1[a] (N = 26) | | Group B2[a] (N = 25) | |
| --- | --- | --- | --- | --- |
| | Period 1 | Period 2 | Period 1 | Period 2 |
| $C_{max}$ (ng/mL) | | | | |
| n | 26 | 26 | 25 | 25 |
| Mean (SD) | 9.18 (5.148) | 10.07 (4.394) | 9.63 (5.419) | 10.69 (5.169) |
| % CV | 56.07 | 43.62 | 56.25 | 48.34 |
| Median | 8.00 | 9.45 | 8.16 | 9.39 |
| Min, Max | 2.7, 23.0 | 4.3, 20.7 | 3.6, 22.7 | 4.8, 28.6 |
| $T_{max}$ (h) | | | | |
| n | 26 | 26 | 25 | 25 |
| Median | 1.000 | 1.000 | 1.000 | 1.000 |
| Min, Max | 1.00, 4.00 | 0.50, 4.00 | 0.50, 2.08 | 0.25, 2.00 |
| $AUC_{0-t}$ (h*ng/mL) | | | | |
| n | 26 | 26 | 25 | 25 |
| Mean (SD) | 49.37 (34.588) | 53.45 (24.132) | 61.35 (56.872) | 61.16 (40.799) |
| % CV | 70.06 | 45.15 | 92.70 | 66.70 |
| Median | 38.67 | 48.94 | 41.66 | 44.53 |
| Min, Max | 16.7, 151.0 | 17.6, 117.6 | 17.4, 261.5 | 22.9, 185.9 |
| $AUC_{0-\infty}$ (h*ng/mL) | | | | |
| n | 26 | 26 | 25 | 25 |
| Mean (SD) | 57.79 (43.184) | 62.39 (29.937) | 74.98 (81.529) | 71.53 (51.804) |
| % CV | 74.72 | 47.98 | 108.73 | 72.42 |
| Median | 45.33 | 54.33 | 47.35 | 51.59 |
| Min, Max | 18.0, 196.9 | 20.2, 144.5 | 20.3, 397.1 | 26.2, 224.6 |
| $t_{1/2}$ (h) | | | | |
| n | 26 | 26 | 25 | 25 |
| Mean (SD) | 9.60 (2.826) | 9.60 (2.922) | 10.04 (2.829) | 9.51 (2.430) |
| Median | 8.71 | 9.12 | 9.29 | 9.19 |
| Min, Max | 6.2, 17.8 | 5.1, 16.4 | 6.8, 17.3 | 6.1, 16.6 |
| $\lambda z$ (1/h) | | | | |
| n | 26 | 26 | 25 | 25 |
| Mean (SD) | 0.07709 (0.018293) | 0.07886 (0.023816) | 0.07369 (0.017781) | 0.07685 (0.016908) |
| Median | 0.07966 | 0.07642 | 0.07458 | 0.07539 |
| Min, Max | 0.0389, 0.1125 | 0.0422, 0.1366 | 0.0401, 0.1022 | 0.0418, 0.1146 |

[a]Group B1 = EE2/NET on Day 1 of Period 1, then EE2/NET followed by SYM-1219 2 grams on Day 1 of Period 2.
Group B2 = EE2/NET on Day 1 of Period 1, then SYM-1219 2 grams on Day 1 and EE2/NET on Day 2 of Period 2.
Source: Table 14.2.2.13; Listings 16.2.2.12.4-16.2.2.12.6

TABLE 5

Summary of the Percent of Relative Bioavailability for EE2 Plasma Pharmacokinetic Parameters $C_{max}$, $AUC_{0-t}$, and $AUC_{0-\infty}$ by Treatment (Part B)

| Parameter Treatment | Period | n | Mean (% CV) | Geometric Least Squares (LS) Means (SE)[b] | % Ratio: 100*Test/Reference[c] Geometric LSMean % Ratio (SE)[b] | 90% C.I.[b] |
|---|---|---|---|---|---|---|
| $C_{max}$ (pg/mL) | | | | | | |
| Group B1[a] | Period 2 | 26 | 59.88 (42.19) | 55.38 (2.728) | 71.07 (4.951) | (63.09, 80.05) |
|  | Period 1 | 26 | 80.63 (26.84) | 77.92 (3.839) |  |  |
| Group B2[a] | Period 2 | 25 | 92.60 (34.77) | 87.16 (2.369) | 104.96 (4.034) | (98.28, 112.09) |
|  | Period 1 | 25 | 89.12 (36.36) | 83.04 (2.257) |  |  |
| $AUC_{0-t}$ (h*pg/mL) | | | | | | |
| Group B1[a] | Period 2 | 26 | 615.55 (31.20) | 590.74 (11.892) | 94.26 (2.683) | (89.78, 98.95) |
|  | Period 1 | 26 | 643.67 (23.85) | 626.75 (12.617) |  |  |
| Group B2[a] | Period 2 | 25 | 668.63 (26.22) | 643.74 (10.529) | 99.04 (2.291) | (95.20, 103.04) |
|  | Period 1 | 25 | 680.48 (28.91) | 649.96 (10.631) |  |  |
| $AUC_{0-\infty}$ (h*pg/mL) | | | | | | |
| Group B1[a] | Period 2 | 25 | 954.35 (28.75) | 924.75 (28.869) | 105.37 (4.565) | (97.84, 113.48) |
|  | Period 1 | 26 | 911.11 (29.39) | 877.60 (26.363) |  |  |
| Group B2[a] | Period 2 | 25 | 937.42 (33.60) | 882.24 (23.866) | 93.32 (3.570) | (87.41, 99.63) |
|  | Period 1 | 25 | 994.55 (28.91) | 945.39 (25.575) |  |  |

[a] Group B1 = EE2/NET on Day 1 of Period 1, then EE2/NET followed by SYM-1219 2 grams on Day 1 of Period 2. Group B2 = EE2/NET on Day 1 of Period 1, then SYM-1219 2 grams on Day 1 and EE2/NET on Day 2 of Period 2.
[b] From an ANOVA model for the log-transformed results with effects treatment (Period 1: EE2/NET alone, Period 2: EE2/NET in combination with SYM-1219) and subject.
[c] Test is Period 2 [EE2/NET followed by SYM-1219 2 grams on Day 1 (Group B2) or SYM-1219 2 grams on Day 1 and EE2/NET on Day 2 (Group B2)]; Reference is Period 1 (EE2/NET Alone)
Source: Table 14.2.2.15

TABLE 6

Summary of the Percent of Relative Bioavailability for NET Plasma Pharmacokinetic Parameters $C_{max}$, $AUC_{0-t}$, and $AUC_{0-\infty}$ by Treatment (Part B)

| Parameter Treatment | Period | n | Mean (% CV) | Geometric LSMeans (SE)[b] | % Ratio: 100*Test/Reference[c] Geometric LSMean % Ratio (SE)[b] | 90% C.I.[b] |
|---|---|---|---|---|---|---|
| $C_{max}$ (ng/mL) | | | | | | |
| Group B1[a] | Period 2 | 26 | 10.07 (43.62) | 9.16 (0.455) | 113.18 (7.958) | (100.37, 127.63) |
|  | Period 1 | 26 | 9.18 (56.07) | 8.09 (0.402) |  |  |
| Group B2[a] | Period 2 | 25 | 10.69 (48.34) | 9.74 (0.483) | 116.46 (8.178) | (103.27, 131.32) |
|  | Period 1 | 25 | 9.63 (56.25) | 8.36 (0.415) |  |  |
| $AUC_{0-t}$ (h*ng/mL) | | | | | | |
| Group B1[a] | Period 2 | 26 | 53.45 (45.15) | 48.72 (1.738) | 115.52 (5.828) | (105.99, 125.92) |
|  | Period 1 | 26 | 49.37 (70.06) | 42.17 (1.504) |  |  |
| Group B2[a] | Period 2 | 25 | 61.16 (66.70) | 51.94 (1.361) | 110.78 (4.104) | (103.97, 118.03) |
|  | Period 1 | 25 | 61.35 (92.70) | 46.88 (1.228) |  |  |
| $AUC_{0-\infty}$ (h*ng/mL) | | | | | | |
| Group B1[a] | Period 2 | 26 | 62.39 (47.98) | 56.42 (2.070) | 116.27 (6.032) | (106.41, 127.04) |
|  | Period 1 | 26 | 57.79 (74.72) | 48.53 (1.780) |  |  |
| Group B2[a] | Period 2 | 25 | 71.53 (72.42) | 59.95 (1.640) | 108.75 (4.207) | (101.78, 116.19) |
|  | Period 1 | 25 | 74.98 (108.73) | 55.13 (1.508) |  |  |

[a] Group B1 = EE2/NET on Day 1 of Period 1, then EE2/NET followed by SYM-1219 2 grams on Day 1 of Period 2. Group B2 = EE2/NET on Day 1 of Period 1, then SYM-1219 2 grams on Day 1 and EE2/NET on Day 2 of Period 2.
[b] From an ANOVA model for the log-transformed results with effects treatment (Period 1: EE2/NET alone, Period 2: EE2/NET in combination with SYM-1219) and subject.
[c] Test is Period 2 [EE2/NET followed by SYM-1219 2 grams on Day 1 (Group B2) or SYM-1219 2 grams on Day 1 and EE2/NET on Day 2 (Group B2)]; Reference is Period 1 (EE2/NET Alone)
Source: Table 14.2.2.16

EE2 $C_{max}$ was reduced by 29% (90% CI 63.09, 80.05) for Group B1; no change in EE2 AUC was seen. EE2 PK was not altered for Group B2. NET $C_{max}$ and AUC increased (13%) slightly for Group B1. NET $C_{max}$ increased by 16% for Group B2; no change was seen for NET AUC. There was no effect (90% CIs within 80-125%) on $AUC_{0-t}$ or $AUC_{0-\infty}$ when SYM-1219 was administered immediately after EE2/NET administration. When EE2/NET was administered 1 day after SYM-1219 administration, there was no effect (90% CIs within 80-125%) from SYM-1219 on EE2 $C_{max}$, $AUC_{0-t}$ or $AUC_{0-\infty}$.

Simultaneous co-administration of EE2/NET and SYM-1219 appears to decrease the rate but not the extent of EE2 absorption. Administration of EE2/NET one day after SYM-1219 appears to have no effect on EE2 absorption.

NET $C_{max}$, $AUC_{0-t}$ or $AUC_{0-\infty}$ were increased by 13-16% and the upper value of 90% CIs were just above 125% when SYM-1219 was administered immediately after EE2/NET administration. When EE2/NET was administered 1 day after SYM-1219 administration the NET $C_{max}$, $AUC_{0-t}$ or $AUC_{0-\infty}$, were increased by 9-16%. The NET upper value of the 90% CI for $C_{max}$ was 131% and there was no effect (90% CIs within 80-125%) from SYM-1219 on $AUC_{0-t}$ or $AUC_{0-\infty}$.

Simultaneous co-administration of EE2/NET and SYM-1219 may result in small (13-16%) increases in the rate and the extent of NET absorption. Administration of EE2/NET one day after SYM-1219 may result in a small (16%) increase in the rate but not the extent of NET absorption.

SYM-1219 was safe and well-tolerated when taken alone or in combination with EE2/NET. The most common adverse events were headache and nausea. All adverse events were mild and resolved without sequelae. There were no significant changes in vital signs, ECG or laboratory parameters. Concomitant administration of SYM-1219 with EE2/NET is not expected to have an effect on contraceptive efficacy.

Conclusions: This study characterized the PK of EE2/NET with SYM-1219 co-administration. Minor, clinically insignificant, reductions in EE2 exposure were seen when SYM-1219 and EE2/NET were co-administered on the same day. No change in EE2 exposure was seen when the SYM-1219 and EE2/NET doses were staggered by one day. No reductions in drug exposure were evident for NET for either treatment group. These in vivo data indicate that contraceptive efficacy for EE2/NET will not be altered by SYM-1219 administration. This was surprising in light of in vitro metabolism data indicating that concentrations of EE2 and NET may be lowered and contraceptive efficacy may be adversely affected by co-administration of SYM-1219.

Example 3—Microbiology—Susceptibility Testing

Susceptibility testing was conducted with one hundred (100) clinical isolates of *T. vaginalis*. These clinical isolates were obtained by culture from women in Birmingham, AL from 2015 to 2016, and grown in vitro for three passages according to CDC protocol (Ghosh, et al., "In vitro study of the Susceptibility of Clinical Isolates of *Trichomonas vaginalis* to metronidazole and secnidazole," *Antimicrob. Agents Chemother.*, 62(2):e02329-17 (2018)).

Archived, de-identified, clinical isolates of *T. vaginalis* that were banked in liquid nitrogen were used for this study. The samples had been collected between July 2015 and June 2017, in accordance with institutional review board guidelines, and all patients had consented to the storage and use of their samples for subsequent testing. Isolates were assayed for metronidazole ("MTZ") and secnidazole susceptibility under aerobic conditions, according to the method described previously in Meingassner, et. al., "Strain of *Trichomonas vaginalis* resistant to metronidazole and other 5-nitroimidazoles," *Antimicrob Agents Chemother.*, 15:254-257 (1979), using serial drug concentrations from 400 µg/ml to 0.2 µg/ml. In brief, trichomonads were grown in Diamond's medium 1025 (containing trypticase soy broth, yeast extract, maltose, and calf serum) adjusted to pH 5.9 and supplemented with streptomycin at 1 g/liter and penicillin G at 100 U/ml. A hemocytometer was used to count the trichomonad population and to adjust it to a concentration of 66,666 cells/ml. Isolates were tested in microtiter plates under aerobic conditions. Minimal lethal concentrations ("MLCs") for metronidazole and secnidazole were tested in triplicate. Plates were then incubated at 37° C. for 46 hours to 50 hours and read with a Zeiss Axiovert inverted microscope. The concentration of drug in the microplate wells in which no motile trichomonads were observed was reported as the MLC. Control strains included CDC252 (resistant) and CDC520 (sensitive) and an archived sample (isolate 009) that had previously exhibited in vitro resistance to both metronidazole and tinidazole ("TNZ"). Low-level resistance was defined as an aerobic MLC of 50 µg/ml to 100 µg/ml, moderate-level resistance as an aerobic MLC of 200 µg/ml, and high-level resistance as an aerobic MLC of >400 µg/ml. The MLCs for metronidazole and secnidazole were analyzed using the Wilcoxon signed-rank test to evaluate the differences between treatments.

Parasite-infected growth media were treated for 48 hours with secnidazole or metronidazole (0.2 µg/mL to 400 µg/mL). Generally, the clinical isolates of *T. vaginalis* had a lower MLC for secnidazole compared to metronidazole.

Each well of a 96-well plate was filled with 150 µL of *T. vaginalis* suspension in Diamond's growth media ($10^4$ trichomonads). Samples were treated with secnidazole (0.2 µg/mL to 400 µg/mL), metronidazole (0.2 tg/mL to 400 tg/mL), CDC control 520 (susceptible), CDC control 252 (resistant), and clindamycin (a drug with no known efficacy against *T. vaginalis*; 0.03 µg/mL to 32 µg/mL) for 48 hours. Cultures were visually assessed for survival, defined by observation of motility, through a 100× inverted microscope. The MLC of each drug was defined as the lowest treatment concentration that resulted in no motility in all samples tested.

Of the 100 clinical *T. vaginalis* isolates tested, 96 (96%) demonstrated a lower MLC for secnidazole than for metronidazole. The mean (±SD) MLC values for metronidazole and secnidazole among all isolates were 13.5±26.9 µg/mL and 5.9±13.2 µg/mL, respectively. The median MLC for metronidazole was 6.3 µg/mL while that for secnidazole was 1.6 µg/mL (FIG. 6). Ninety-six (96%) of the 100 clinical *Trichomonas* isolates tested demonstrated a lower MLC for secnidazole than for metronidazole, while 3 of the isolates had similar MLCs for metronidazole and secnidazole (P<0.0001, Wilcoxon signed-rank test) (FIG. 7). One isolate demonstrated a higher MLC for secnidazole (3.1 µg/ml) than for metronidazole (1.6 µg/ml). The prevalence of low-level metronidazole resistance was 7%, while 1% of the isolates exhibited moderate metronidazole resistance. Four percent of the isolates exhibited low-level resistance to secnidazole, while none of the isolates demonstrated moderate- or high-level secnidazole resistance. Correlation analysis revealed a strong relationship between the MLC for metronidazole and the MLC for secnidazole (r=0.9496; P<0.0001), indicating that the isolates with increased resistance to metronidazole also demonstrated decreased sensitivity to secnidazole (FIG. 8). Several clinical isolates that were resistant to metronidazole were sensitive to significantly lower concentrations of secnidazole (p<0.0001).

Interestingly, 5 clinical isolates were identified to exhibit low-level metronidazole resistance, and all of those isolates responded to significantly lower concentrations of secnidazole. We also identified 1 clinical isolate with moderate-level metronidazole resistance, which had a significantly lower ("MLC") for secnidazole. Interestingly, our control isolates with established high-level resistance to metronidazole responded to significantly lower levels of secnidazole. In view of the increasing incidence of metronidazole-resistant *T. vaginalis* infections and the sole reliance on 5-nitroimidazoles to treat *T. vaginalis*, a therapeutic alternative to metronidazole is needed. While secnidazole may not be effective for all patients with metronidazole-resistant *T. vaginalis* infections, the increased sensitivity of metronidazole-resistant trichomonads to secnidazole suggests that patients with infections that are refractory to metronidazole treatment may still respond to secnidazole, as indicated by previous studies with patients with *T. vaginalis* infections who failed treatment with metronidazole and responded to tinidazole.

Thus, the above data shows that secnidazole has superior efficacy in vitro in comparison with metronidazole, and that the concentration of secnidazole needed for therapeutic efficacy may be lower than of metronidazole.

Additionally, for male subjects, the plasma concentration values for secnidazole at ≥24 hours postdose and/or $T_{last}$ (i.e., the final PK sample collection timepoint) are reported in Table 7 below. The concentrations are normalized to the dose of 2 grams secnidazole. Plasma secnidazole concentrations remain well above the mean MLC for *T. vaginalis* of 5.9 µg/mL at 24 hours postdose. At 96 hours, mean dose-normalized (to 2 grams) concentrations of secnidazole are approximately 2 µg/mL based on the published studies in men (Wei et al., "Bioequivalent study of secnidazole in healthy volunteers," *Clin. J. Infect. Chemother.*, 6(3): 159-162 (2006); Zhu et al., "Evaluation of the bioequivalence and pharmacokinetics of two formulations of secnidazole after single oral administration in healthy volunteers," *Arzneimittel-Forschung Drug Res.*, 57(11):723-726 (2007)). A similar value is estimated from the results in Table 7 below for SYM-1219 for the 2-gram dose of secnidazole oral microgranules (i.e., assuming a $T_{1/2}$ of 24 hours in men, and extrapolating from the 24-hour mean concentration of 18.0 m/mL, the mean concentration at 96 hours is estimated at approximately 2.25 µg/mL). Such data demonstrates that efficacious secnidazole concentrations, greater than the median MLC of 1.6 µg/mL, are maintained up to at least 96 hours postdose in men.

Example 4—Clinical Studies

A Phase 3 multi-center, prospective, randomized, placebo-controlled, delayed treatment, double-blind study of a single oral dose of SYM-1219 (2 grams of secnidazole) for the treatment of trichomoniasis in adult women was conducted at 10 clinical sites in the U.S. The study was conducted to evaluate the efficacy and safety of SYM-1219 (2 grams of secnidazole) compared to placebo on adult women patients with trichomoniasis. A total of 147 female patients with trichomoniasis were enrolled in the study and 143 patients (97.3%) completed the Test of Cure ("TOC") visit. The Modified Intent-To-Treat ("mITT") population (131 patients) included all randomized patients who met all inclusion/exclusion criteria. Patients with trichomoniasis and comorbid conditions of HIV and/or bacterial vaginosis were also included in the study. Average age of the patients in the mITT population was 37.7 (Standard Deviation ("SD")+/−11.2 years) years old with the youngest patient at 15 years old and the oldest patient at 65 years old. 90.8% were black or African American in the mITT population.

The trial demonstrated a clinically and statistically significant response rate, or microbiological cure, in patients dosed with SYM-1219 (2 grams of secnidazole) as compared to placebo (p<0.001). Patients were dosed in a double-blind manner with SYM-1219 (2 grams of secnidazole) or placebo, orally administered, under direct observation, as a single 2-gram dose with approximately 4 ounces of unsweetened applesauce.

This study included a treatment delay for the patients originally randomized to placebo. As described in FDA's "Draft Guidance for Industry: Uncomplicated Urinary Tract Infections: Developing Drugs for Treatment (May 2018)," a treatment-delay study design allows for a finding of superiority of the investigational drug compared to placebo at a time point early in therapy, after which patients randomized to treatment delay receive antibacterial drug treatment. This study design principle was applied to the trichomoniasis indication, which allowed for a placebo comparison and rapid follow-up treatment for patients originally randomized to placebo.

Inclusion criteria for this study included:
Adult female or post-menarche adolescent girl≥12 years of age in general good health;

TABLE 7

Concentration Values at ≥24 Hours Postdose or $T_{last}$ in Males with MLC for *T. vaginalis*

| Formulation | Dose | Time (hr) | Mean Concentration (µg/mL) | Mean Concentration Normalized to 2 grams (µg/mL) | MLC for Secnidazole (µg/mL) |
|---|---|---|---|---|---|
| SYM-1219, oral microgranules | 4 grams of secnidazole | 24[a] | 39.1 | 19.6 | Mean: 5.9 |
| | 6 grams of secnidazole | 24[a] | 70.2 | 23.4 | |
| SYM-1219, oral microgranules | 2 grams of secnidazole | 24[a] | 18.0 | 18.0 | Median: 1.6 |
| | 6 grams of secnidazole | 24[a] | 57.7 | 19.2 | |

MLC = minimal lethal concentration;
NR = not reported
[a]$T_{last}$

Has a diagnosis of trichomoniasis at the screening visit as determined by one of the following:
  Positive *T. vaginalis* nucleic acid amplification test ("NAAT") test within 30 days of screening for which treatment has not been initiated,
  Positive OSOM® Rapid test, or
  Positive wet mount assessment;
Agrees to abstain from vaginal intercourse or vaginal penetration by any vaginal products (e.g., spermicides, tampons, vaginal douches, lubricants) until the final study visit;
Agrees not to have any vaginal penetration or use of any vaginal products for the duration of the study; and
HIV-positive patients and patients with bacterial vaginosis (based on Amsel criteria) were eligible.
Exclusion criteria for this study included:
Is pregnant, lactating, or planning to become pregnant during the study;
Is suspected clinically (or confirmed diagnostically) of having alternative causes of vaginal symptoms including symptomatic vulvovaginal candidiasis, chlamydia, gonorrhea, or an active genital herpes outbreak;
Is suspected clinically of having an acute urinary tract infection;
Has active genital lesions, including primary syphilitic chancres and herpes simplex virus lesions, or other vaginal or vulvar conditions which could confound the interpretation of the clinical response, as determined by the Investigator (patients with genital warts may be enrolled); and
Has received systemic antibacterial therapy or topical antimicrobial/antifungal/immunomodulatory therapies in the genital area (vagina, vulva and surrounding soft tissue), within 14 days prior to the Baseline Visit (Day 1).

As trichomoniasis is a STD requiring treatment upon diagnosis, a treatment-delay placebo-controlled trial was incorporated to prevent the patient from spreading the disease to other sexual partners. In the treatment delay study, patients testing positive for *T. vaginalis*, determined as a positive test for *T. vaginalis* on InPouch® TV test, OSOM® Trichomoniasis Rapid Test, wet mount, or a positive NAAT test within 30 days of screening (and have not been treated) were enrolled.

For wet mount analysis, the study used the KOH Whiff Test and Vaginal Saline Wet Mount. To obtain a vaginal discharge sample from a subject, Investigator, or designee, used sterile polyester-tipped swabs to swab the lateral vaginal walls with a polyester-tipped applicator; placed polyester tip in a tube with approximately 6 drops of saline (~100 µl; enough to keep the swab moist, but not dilute the sample); and removed the swab from the tube and placed a liberal amount of discharge on each of the two glass slides immediately before testing as follows:
  A. Slide #1—KOH Whiff Test: The Investigator, or designee, mixed approximately two drops of 10% potassium hydroxide (KOH) with the vaginal discharge sample and immediately smell the slide to assess for a fishy, amine-like odor (record as Positive or Negative; a Positive result indicated the presence of the odor).
  B. Slide #2—Vaginal Saline Wet Mount: The Investigator, or designee, examined the second vaginal sample slide under a light microscope at 100× magnification and at 400× magnification for the presence or absence of clue cells and motile trichomonads:
    Clue cells: A minimum of 5 representative fields containing squamous epithelial cells was examined and the ratio of clue cells to vaginal epithelial cells determined at 400× magnification. Clue cells were identified as vaginal epithelial cells with such a heavy coating of bacteria surrounding them, which obscured their peripheral borders. Clue cells were recorded as ≥20% of the total epithelial cells, or <20% of the total epithelial cells.
    *Trichomonads*: The Investigator, or designee recorded motile trichomonads as Present or Absent.

Eligible patients were randomized 1:1 to SYM-1219 (2 grams of secnidazole) or matching placebo (as recommended by the FDA). Randomization was stratified by site and clinical symptoms of trichomoniasis (present or absent). Patients were evaluated at a baseline Visit 1 ("V1") and 6-12 days later at Visit 2 ("V2"). The primary efficacy endpoint was microbiology cure by culture at V2 (test-of-cure; TOC). At the TOC visit, patients received the opposite treatment from baseline (i.e., SYM-1219 (2 grams of secnidazole) if they had received placebo at baseline or placebo if they had received SYM-1219 (2 grams of secnidazole) at baseline) and were followed for resolution of infection at subsequent visits, with additional treatment provided as needed.

Upon meeting eligibility criteria, patients were evaluated at the baseline V1. Demographics, medical history (including presence of genital symptoms), vital signs, urine pregnancy testing, and a physical examination were performed. A pelvic examination was also performed to assess genital signs and to collect vaginal samples for OSOM® *Trichomonas* Rapid Test, *T. vaginalis* culture (BioMed InPouch® TV test), vaginal wet mount, KOH whiff test, pH of vaginal fluid and STI testing. Patients were screened for chlamydia and gonorrhea using NAAT. Patients were dosed in a double-blind manner with SEC or placebo, orally administered, under direct observation, as a single 2-g dose with approximately 4 ounces of unsweetened applesauce. Women were counseled to refrain from any sexual activity until the final study visit and to notify all sexual partners within the past 60 days to be treated as contacts to trichomoniasis. Patients returned to the clinic for V2 (6-12 days post V1) for TOC. At that time, the clinician queried patient for adverse events, assessed her for clinical symptoms of trichomoniasis, and collected a vaginal sample for *T. vaginalis* culture. At the TOC visit, patients received the opposite treatment from baseline (i.e., SYM-1219 (2 grams of secnidazole) if they had received placebo at baseline or placebo if they had received SYM-1219 (2 grams of secnidazole) at baseline). Patients with V2 cultures that were positive for *T. vaginalis* were asked to return to the clinic for Visit 3 ("V3"), 7-12 days post V2, for an additional assessment, including determination of need for additional therapy. An additional Visit 4 (7-12 days post V3) was scheduled at the investigator's discretion if a repeat *T. vaginalis* culture at V3 was positive. Assessments at Visits 3 and 4 were the same as at V2.

The primary endpoint in this clinical efficacy study was microbiological cure, defined as a negative *T. vaginalis* culture, at the TOC visit. To reduce the possibility of re-infection from unprotected sex after a patient is cured, the TOC visit was specifically selected during Day 6 to Day 12. As required by the FDA, the primary population for efficacy analysis was the modified intent-to-treat ("mITT") population, defined as all randomized patients who had a positive *T. vaginalis* culture at baseline as well as a negative chlamydia and gonorrhea NAAT test. The secondary population for efficacy analysis was the Per-Protocol ("PP") population, defined as patients in the mITT population who received study medication as randomized, had a TOC visit and had no major protocol violations. The composition of the PP population was finalized and documented in a review of the data conducted prior to unblinding the study database. The PP population was used for supportive efficacy analyses. Intent-to-Treat ("ITT") population included all randomized patients.

Secondary post hoc efficacy analyses of the microbiological cure rate at TOC, compared SYM-1219 (2 grams of secnidazole) and placebo: (1) among patients with trichomoniasis who were symptomatic and those who were asymptomatic, (2) among patients who were infected with HIV, and (3) among patients who had bacterial vaginosis at baseline (based on Amsel criteria). Additional exploratory endpoints included symptom resolution in the subgroup of patients who have baseline symptoms (e.g., vaginal itching, discharge, and odor) attributable to trichomoniasis.

Safety analyses, including the evaluation of adverse events, physical examinations, pelvic examinations, collection of vital signs (blood pressure, temperature, and pulse), and clinical laboratory assessments (serum chemistry, hematology, and urinalysis) was conducted at all study visits. Adverse event information was also collected on the phone call between study V2 and V3.

The primary efficacy endpoint, Microbiological Cure (i.e., InPouch™ TV test negative for *T. vaginalis*) at the TOC visit, was compared between the active and placebo treatment groups using a two-sided Cochran-Mantel-Haesnzel ("CMH") test (stratified by the presence/absence of clinical symptoms of trichomoniasis at baseline, HIV status and bacterial vaginosis status) at the α=0.05 level of significance. All analyses were performed using SAS® software version 9.4 (Cary, NC).

The primary efficacy endpoint was evaluated at the TOC Visit for the subgroup of patients who have clinical symptoms of trichomoniasis at baseline: Outcome Responder, which means complete resolution of trichomoniasis symptoms (i.e., itching, discharge, and odor recorded as normal) and culture results (InPouch™ TV test) negative for *T vaginalis*.

Overall, the above trial met its primary endpoint of microbiological cure at the TOC visit on study Day 6-12, defined as a negative *T. vaginalis* culture for the mITT population. The predefined primary efficacy endpoint, defined as microbiological cure (i.e., InPouch™ TV test negative for *T. vaginalis*) at the TOC visit (Day 6-12) in the mITT population (all randomized subjects who were culture positive for *T. vaginalis* and negative for gonorrhea and chlamydia at baseline), was about 92.2% (59/64) for SYM-1219 (2 grams of secnidazole) versus about 1.5% (1/67) for placebo (p<0.001). See Table 8 below.

TABLE 8

Summary of Microbiological Cure at TOC Visit by Treatment in Modified Intent-To-Treat ("mITT") Population

| | SYM-1219 (2 grams) (N = 64)* | Placebo (N = 67)* |
|---|---|---|
| Microbiological Cure[a] [n (%)] | 59 (92.19%) | 1 (1.49%) |
| Number Imputed[b] | 1 | 3 |
| 95% Exact Binomial Confidence Interval ("95% CI") | 82.70, 97.41 | 0.04, 8.04 |
| P-value[c] | <0.001 | |

[a] InPouch™ TV test negative for *T. vaginalis*.
[b] Subjects with no test results are assumed to be positive.
[c] P-value versus placebo from a Cochran-Mantel-Haenszel ("CMH") test adjusted for clinical symptoms (present/absent) of trichomoniasis at baseline.
*N = number of patients in treatment group (modified intent-to-treat population defined as all randomized patients who were culture positive for *T. vaginalis* and negative for other sexually transmitted infections)

As shown in Table 8 above, statistically significant (p<0.001) microbiological cure rates at the TOC visit were also observed with the mITT sensitivity analysis [SYM-1219 (2 grams of secnidazole) group (59/64 patients; 92.19%) as compared to the placebo group (1/67 patients; 1.49%)].

As shown in Table 9 below, statistically significant (p<0.001) microbiological cure rates at the TOC visit were observed with the PP population analysis [SYM-1219 (2 grams of secnidazole) group (56/59 patients; 94.92%) as compared to the placebo group (1/60 patients; 1.67%)].

TABLE 9

Summary of Microbiological Cure at TOC Visit by Treatment in PP Population

| | SYM-1219 (2 grams) (N = 59)* | Placebo (N = 60)* |
|---|---|---|
| Microbiological Cure[a] [n (%)] | 56 (94.92%) | 1 (1.67%) |
| 95% CI | 85.85, 98.94 | 0.04, 8.94 |
| P-value[b] | <0.001 | |

[a] InPouch™ TV test negative for *T. vaginalis*.
[b] P-value versus placebo from a CMH test adjusted for clinical symptoms (present/absent) of trichomoniasis at baseline.

As shown in Table 10 below, microbiological cure rates were analyzed in each of the two symptom strata (presence/absence of trichomoniasis symptoms at baseline). In the mITT analysis population, the microbiological cure rate at the TOC visit was significantly higher in the SYM-1219 (2 grams of secnidazole) group as compared to the placebo group in both baseline clinical symptom strata [92.9% (52/56 patients) vs 0% (0/55 patients) with trichomoniasis symptoms and 87.5% (7/8 patients) vs 8.3% (1/12 patients) without trichomoniasis symptoms in the SYM-1219 (2 grams of secnidazole) group vs placebo group, respectively (p<0.001)].

TABLE 10

Summary of Microbiological Cure at TOC Visit by Clinical Symptoms Strata and Treatment (mITT Population)

|  | SYM-1219 (2 grams) (N = 64) | Placebo (N = 67) |
|---|---|---|
| Presence of Clinical Symptoms[a] | | |
| Microbiological Cure[b] [n/N (%)] | 52/56 (92.9%) | 0/55 (0%) |
| Number Imputed[c] | 0 | 3 |
| 95% CI | 82.7, 98.0 | 0.00, 6.49 |
| P-Value[d] | <0.001 | |
| Absence of Clinical Symptoms[a] | | |
| Microbiological Cure[b] [n/N (%)] | 7/8 (87.5%) | 1/12 (8.3%) |
| Number Imputed[c] | 1 | 0 |
| 95% CI | 47.4, 99.7 | 0.2, 38.5 |
| P-Value[d] | <0.001 | |

[a] inching, discharge, odor attributed to *T. vaginalis*, as determined by a provider, at baseline.
[b] InPouch™ test negative for *T. vaginalis*.
[c] Subjects with no test results are assumed to be positive.
[d] From a Fisher's Exact test.

As shown in Table 11 below, statistically significant (p<0.001) microbiological cure rates were also observed in both baseline clinical symptom strata in the PP population analysis. In the PP analysis population, the microbiological cure rate at TOC visit was significantly higher in the SYM-1219 (2 grams of secnidazole) group as compared to the placebo group in both baseline clinical symptom strata [about 94.23% (49/52 patients) vs 0% (0/49 patients) with trichomoniasis symptoms and 100% (7/7 patients) vs about 9.09% (1/11 patients)) without trichomoniasis symptoms in the SYM-1219 (2 grams of secnidazole) group vs placebo group, respectively (p<0.001)]. This data reaffirms what is shown in the mITT data shown in Table 10 above.

TABLE 11

Summary of Microbiological Cure at TOC Visit by Clinical Symptoms Strata and Treatment (PP Population)

|  | SYM-1219 (2 grams) (N = 59) | Placebo (N = 60) |
|---|---|---|
| Presence of Clinical Symptoms[a] | | |
| Microbiological Cure[b] [n/N (%)] | 49/52 (94.23%) | 0/49 (0%) |
| 95% CI | 84.05, 98.79 | 0.00, 7.25 |
| P-Value[d] | <0.001 | |
| Absence of Clinical Symptoms[a] | | |
| Microbiological Cure[b] [n/N (%)] | 7/7 (100.0%) | 1/11 (9.09%) |
| 95% CI | 59.04, 100.00 | 0.23, 41.28 |
| P-Value[d] | <0.001 | |

[a] inching, discharge, odor attributed to *T. vaginalis*, as determined by a provider, at baseline.
[b] InPouch™ test negative for *T. vaginalis*.
[c] From a Fisher's Exact test.

As shown in Table 12 below, in patients with *T. vaginalis* and bacterial vaginosis at baseline, the microbiological cure rate at the TOC visit was significantly higher (p<0.001) in the SYM-1219 (2 grams of secnidazole) group (20/21 patients; about 95.24%) as compared to the placebo group (0/17 patients; 0%). Patients with bacterial vaginosis presented 4 out of 4 Amsel criteria (abnormal vaginal discharge (e.g., thin, homogenous vaginal discharge), a positive KOH Whiff test, vaginal fluid pH greater than or equal to 4.7, and the presence of clue cells greater than 20% of total epithelial cells). Microbiological cure was defined as InPouch™ test negative for *T. vaginalis* at Visit 2.

TABLE 12

Summary of Microbiological Cure at TOC Visit in Patients with HIV or Bacterial Vaginosis ("BV")-(mITT Population)

| Analysis | SYM-1219 (2 grams) (N = 64) | Placebo (N = 67) | P value[c] |
|---|---|---|---|
| Microbiologic Cure in Patients with HIV | 5/5 (100%) | 0/4 (0%) | NC |
| Microbiologic Cure in Patients with BV | | | <0.001 |
| Microbiological Cure[a] [n/N (%)] | 20/21 (95.24%) | 0/17 (0%) | |
| Number imputed[b] | 0 | 1 | |
| 95% CI | 76.18%, 99.88% | 0%, 19.51% | |

CI = confidence interval;
HIV = human immunodeficiency virus;
NC = not calculated

[a] InPouch™ TV test negative for *T. vaginalis* for bacterial vaginosis subjects, defined as those meeting all four Amsel criteria at baseline (any abnormal discharge, clue cells greater than or equal to 20% of total epithelial cells, positive KOH whiff test, and vaginal pH greater than or equal to 4.7).
[b] Subjects with no test results are assumed to be positive.
[c] P-value versus placebo from a CMH test adjusted for clinical symptoms (present/absent) of trichomoniasis at baseline.

Also, as shown in Table 12 above, in patients with *T. vaginalis* and HIV-positive at baseline, the microbiological cure rate at the TOC visit was significantly higher in the SYM-1219 (2 grams of secnidazole) group (4/4 patients; 100%) as compared to the placebo group (0/5 patients; 0%). Microbiological cure was defined as InPouch™ test negative for *T. vaginalis* at Visit 2.

Table 13 below provides a summary of treatment-emergent adverse events ("TEAEs") by treatment for this study.

TABLE 13

Summary of Treatment-Emergent Adverse Events by Treatment-(Safety Population)

| System Organ Class Preferred Term | Secnidazole 2 grams (N = 74) Patient[a] n (%) | Events n | Placebo (N = 73) Patient[a] n (%) | Events n |
|---|---|---|---|---|
| *Any Adverse Event* | | | | |
| Overall | 11 (14.9%) | 13 | 16 (21.9%) | 20 |
| *Gastrointestinal disorders* | | | | |
| Overall | 4 (5.4%) | 5 | 6 (8.2%) | 7 |
| Nausea | 2 (2.7%) | 2 | 3 (4.1%) | 3 |
| Abdominal pain | 1 (1.4%) | 1 | 1 (1.4%) | 1 |
| Diarrhea | 1 (1.4%) | 1 | 2 (2.7%) | 2 |
| Vomiting | 1 (1.4%) | 1 | 1 (1.4%) | 1 |
| *Infections and infestations* | | | | |
| Overall | 3 (4.1%) | 3 | 2 (2.7%) | 2 |
| Vulvovaginal candidiasis | 2 (2.7%) | 2 | 0 | 0 |
| Vulvovaginal mycotic infection | 1 (1.4%) | 1 | 0 | 0 |
| Trichomoniasis | 0 | 0 | 2 (2.7%) | 2 |
| *Respiratory, thoracic and mediastinal disorders* | | | | |
| Overall | 2 (2.7%) | 2 | 0 | 0 |
| Productive cough | 1 (1.4%) | 1 | 0 | 0 |
| Upper-airway cough syndrome | 1 (1.4%) | 1 | 0 | 0 |
| *Musculoskeletal and connective tissue disorders* | | | | |
| Overall | 1 (1.4%) | 1 | 1 (1.4%) | 1 |
| Myalgia | 1 (1.4%) | 1 | 0 | 0 |
| Back pain | 0 | 0 | 1 (1.4%) | 1 |
| *Nervous system disorders* | | | | |
| Overall | 1 (1.4%) | 1 | 5 (6.8%) | 5 |
| Headache | 1 (1.4%) | 1 | 5 (6.8%) | 5 |
| *Reproductive system and breast disorders* | | | | |
| Overall | 1 (1.4%) | 1 | 3 (4.1%) | 3 |
| Vulvovaginal pruritus | 1 (1.4%) | 1 | 0 | 0 |
| Dysmenorrhoea | 0 | 0 | 2 (2.7%) | 2 |
| Menstruation irregular | 0 | 0 | 1 (1.4%) | 1 |
| *General disorders and administration site conditions* | | | | |
| Overall | 0 | 0 | 1 (1.4%) | 1 |
| Thirst | 0 | 0 | 1 (1.4%) | 1 |
| *Skin and subcutaneous tissue disorders* | | | | |
| Overall | 0 | 0 | 1 (1.4%) | 1 |
| Pruritus | 0 | 0 | 1 (1.4%) | 1 |

Note:
Includes all TEAEs during the primary phase (start date on or before the TOC visit).
[a]Patients experiencing multiple adverse events are only counted once within a given cell.

The safety and tolerability of SYM-1219 (2 grams of secnidazole) was evaluated in all 147 patients (74 SYM-1219 (2 grams of secnidazole); 73 placebo) in the safety population. As shown in Table 13 above, the SYM-1219 (2 grams of secnidazole) was well tolerated. Adverse events were lower in the SYM-1219 (2 grams of secnidazole) group compared to the placebo group. All adverse events were mild; none were severe. Only one patient in the SYM-1219 (2 grams of secnidazole) was discontinued due to adverse events (mild nausea and productive cough). The most frequent adverse events were vulvovaginal candidiasis and nausea (each 2.7%). No deaths or serious or severe adverse events were observed.

Overall, SYM-1219 (2 grams of secnidazole) was safe and had a significantly high microbiological cure, about 92%-95%, compared to placebo, and was effective in treating women with trichomoniasis, including those with HIV or bacterial vaginosis. In the mITT population, the analysis of the microbiological cure rate at the TOC visit (primary efficacy endpoint) demonstrated that the SYM-1219 (2 grams of secnidazole) group (59/64 patients; 92.19%) was superior to placebo (1/67 patients; 1.49%) (p<0.001).

All additional endpoints demonstrated that the SYM-1219 (2 grams of secnidazole) group was superior to placebo in the mITT population including:

The microbiological cure rate at the TOC visit in each of the two baseline symptom strata [92.9% (52/56 patients) vs 0% (0/55 patients) with trichomoniasis symptoms and 87.5% (7/8 patients) vs 8.3% (1/12 patients) without trichomoniasis symptoms in the SYM-1219 (2 grams of secnidazole) vs placebo groups, respectively (p<0.001)]. The outcome responder rate at the TOC visit [SYM-1219 (2 grams of secnidazole) group (41/56 patients; 73.21%) as compared to the placebo group (0/55 patients; 0%) (p<0.001)].

Analysis of the PP population demonstrated similar results [SYM-1219 (2 grams of secnidazole) group (56/59 patients; 94.92%) as compared to the placebo group (1/60 patients; 1.67%) (p<0.001)].

High microbiological cure rates were also observed with SYM-1219 (2 grams of secnidazole) group compared to the placebo in patients with co-existing baseline conditions of BV [95.24% vs 0% (p<0.001)] and HIV [100% vs 0%].

Also, SYM-1219 (2 grams of secnidazole)'s high microbiological cure rate for a single dose treatment is much higher than the 83.2% cure rate for single dose metronidazole for HIV-positive women with trichomoniasis. See Kissinger, et al., "A randomized treatment trial: single versus 7-day dose of metronidazole for the treatment of *Trichomonas vaginalis* among HIV-infected women," *J. Acquir. Immune Defic. Syndr.*, 55:565-71 (2010)).

Additionally, patients with trichomoniasis and bacterial vaginosis at baseline, SYM-1219 (2 grams of secnidazole) was also highly efficacious with a cure rate of 95.2% (20/21) versus 0% (0/17) for placebo (P<0.001). The coexistence of bacterial vaginosis and *T. vaginalis* is common, with coinfection rates of 60% to 80%. Sobel, et al., "Mixed vaginitis-more than coinfection and with therapeutic implications," *Curr. Infect. Dis. Rep.* 15(2):104-108 (2013). Further, a single treatment for both bacterial vaginosis and trichomoniasis would be an efficient and effective way to deal with these diseases.

Further, single-dose regimens are likely to improve adherence overall, especially in populations that may be at risk for noncompliance. Compliance with oral metronidazole is reported to be low at 50-63%. See Bartley, et al., "Personal digital assistants used to document compliance of bacterial vaginosis treatment," *Sex Transm. Dis.*, 31(8):488-491 (2004). Factors affecting adherence include gastrointestinal complaints (nausea, stomach cramps, and diarrhea), dosing length and lifestyle restrictions. In a 2018 comparative metronidazole study, 23% of patients reported nausea in both the single-dose and 7-day groups. Kissinger et al., "Single-dose versus 7-day-dose metronidazole for the treatment of trichomoniasis in women: an open-label, randomised controlled trial," *Lancet Infect. Dis.* 18(11):1251-1259 (2018). In contrast, only 2.7% of patients reported nausea with SYM-1219 (2 grams of secnidazole). Additionally, SYM-1219 (2 grams of secnidazole) does not have an alcohol restriction based on in vitro studies, which differs from the potential alcohol-drug interactions associated with metronidazole. See, e.g., Pentikis et al., "In vitro metabolic profile and drug-drug interaction assessment of secnidazole, a high-dose 5-nitroimidazole antibiotic for the treatment of bacterial vaginosis," *Pharmacol. Res. Perspect.*, 8(4): e00634 (2020).

Additionally, a Phase I, randomized, placebo-controlled, single-blind, two-group study, which assessed the safety, tolerability, and PK of single oral doses of SYM-1219 granules containing either 4 grams or 6 grams of secnidazole administered in approximately 8 ounces of applesauce to 16 healthy male and female subjects, was conducted to determine the supratherapeutic dose for a potential Thorough QT ("TQT") study. Subjects were randomized 3:1, such that a total of 12 subjects received secnidazole and 4 subjects received placebo. 3 male and 3 female subjects were treated at each secnidazole dose level (i.e., 4 grams or 6 grams). Blood samples for PK assessments were collected at the following timepoints: 30 minutes prior to dosing and 3 hours, 6 hours, 8 hours and 24 hours post dose. Plasma concentrations were summarized by timepoint using descriptive statistics; noncompartmental PK parameters were not calculated.

Eligible subject were admitted to the clinical site on Day −1 and were discharged following a safety evaluation on Day 2; the in-house period was approximately 2 days. Randomization occurred after the assessments of Day −1 determined that subjects remained eligible for the study. All subject were asked to return on Day 7+/2 days for a final study visit. The maximum study duration was approximately 4 weeks to 5 weeks (including the study screening period).

Group A received a single oral dose of SYM-1219 microgranules, containing 4 grams of secnidazole (N=6) (2 packets of SYM-1219 microgranules, 2 grams of secnidazole/packet), or a placebo (N=2) (2 packets of placebo) in approximately 8 oz. of applesauce. Group B received a single oral dose of SYM-1219 microgranules, containing 6 grams of secnidazole (N=6) (3 packets of SYM-1219 microgranules, 2 grams of secnidazole/packet) or placebo (N=2) (3 packets of placebo) in approximately 8 oz. applesauce. The study drug, SYM-1219, was administered in the fasted state (i.e., after an overnight fast of at least 10 hours).

Blood samples for PK analysis were collected: 30 minutes prior to dosing and 3 hours, 6 hours, 8 hours and 24 hours postdose. Blood samples were collected via direct venipuncture or by the use of an indwelling catheter. If an indwelling catheter was utilized, saline flushes were used. Plasma secnidazole concentrations were determined by Celerion, Inc., using validated analytical procedures. The PK analysis for each treatment group (Group A or Group B) consisted of descriptive statistics to assess the secnidazole concentration data as related to SYM 1219 treatment administration. The PK data for these subjects in this study are summarized by gender in Table 14 below.

TABLE 14

Summary of Secnidazole Plasma Concentration (μ/mL) by Treatment, Timepoint, and Gender

| Postdose Timepoint | SYM-1219 4 grams | | SYM-1219 6 grams | |
|---|---|---|---|---|
| | Males (N = 3) | Females (N = 3) | Males (N = 3) | Females (N = 3) |
| Hour 3 | | | | |
| n | 3 | 3 | 3 | 3 |
| Mean (SD) | 57.033 (11.7509) | 88.833 (13.7871) | 80.967 (18.9136) | 114.667 (14.5029) |
| % CV | 20.604 | 15.520 | 23.360 | 12.648 |
| Hour 6 | | | | |

TABLE 14-continued

Summary of Secnidazole Plasma Concentration
(μ/mL) by Treatment, Timepoint, and Gender

| Postdose Timepoint | SYM-1219 4 grams | | SYM-1219 6 grams | |
|---|---|---|---|---|
| | Males (N = 3) | Females (N = 3) | Males (N = 3) | Females (N = 3) |
| n | 3 | 3 | 3 | 3 |
| Mean (SD) | 65.233 (7.5639) | 87.100 (15.7267) | 99.367 (5.0123) | 121.333 (12.5033) |
| % CV | 11.595 | 18.056 | 5.044 | 10.105 |
| Hour 8 | | | | |
| n | 3 | 3 | 3 | 3 |
| Mean (SD) | 59.667 (7.9027) | 83.100 (20.7877) | 91.800 (3.9850) | 109.267 (11.0821) |
| % CV | 13.245 | 25.015 | 4.341 | 10.142 |
| Hour 24 | | | | |
| n | 3 | 3 | 3 | 3 |
| Mean (SD) | 39.100 (3.9962) | 52.033 (15.1215) | 70.200 (1.7000) | 69.557 (3.6019) |
| % CV | 10.221 | 29.061 | 2.422 | 5.178 |

CV = coefficient of variation;
SD = standard deviation;
n or N = number of subjects For Group A, SYM-1219 containing 4 grams of secnidazole was determined to be not tolerated if the subjects in the SYM-1219 group met the following criteria: 1) if ≥2 out of 6 subjects experience emesis within 4 hours of dosing (approximately $T_{max}$ for secnidazole), 2) if ≥2 out of 6 subjects experience the same adverse event ("AE") that was considered severe in intensity and related to study medication, or 3) if any subject experienced a Serious AE that was considered related to study medication. If any of the above occurred, SYM-1219 containing 2 grams of secnidazole was used in the TQT study.

For Group B, SYM-1219 containing 6 grams of secnidazole was determined to be not tolerated if the subjects in the SYM-1219 group met the following criteria: 1) if ≥2 out of 6 subjects experience emesis within 4 hours of dosing (approximately $T_{max}$ for secnidazole), 2) if ≥2 out of 6 subjects experience the same AE that was considered severe in intensity and related to study medication, or 3) if any subject experienced a Serious AE that was considered related to study medication. If any of the above occurred, SYM-1219 containing 4 grams of secnidazole was used in the TQT study.

Overall, SYM-1219 granules containing either 4 grams or 6 grams of secnidazole were safe and well-tolerated by this population of healthy adult male and female subjects. The overall incidence rate of TEAEs was low; 3 subjects reported TEAEs, all unrelated to study drug. The incidence rate of TEAEs was 16.7% in the SYM-1219, 4-gram group compared to 33.3% in the SYM-1219, 6-gram group. No TEAEs were reported in the placebo group. The TEAEs in the SYM-1219, 4-gram group vs. the SYM-1219, 6-gram group were headache (16.7% vs 16.7%) and upper respiratory infection (0% vs 16.7%), respectively. All of the TEAEs were reported as being mild in severity. No subjects discontinued from the study due to a TEAE and no SAEs were reported. There were no clinically meaningful trends noted based on safety laboratory assessments, vital sign measurements, laboratory values, or ECG findings during this study.

Plasma concentrations increased from 4 grams to 6 grams of secnidazole and were essentially dose-proportional. The variability in plasma concentrations was approximately 4% to 29% across the limited sampling times in this study. The observed secnidazole plasma concentrations and exposures in males appeared to be slightly lower than those observed in females.

A TQT study was also conducted. The TQT study was a double-blind, randomized, placebo-controlled, 4-period, single-dose, crossover design in 52 healthy male and female subjects. The primary objective of this study was to demonstrate that SYM-1219 containing 2 grams of secnidazole did not have an effect on the QTc interval exceeding>10 ms compared to placebo. Subjects were randomized to a treatment sequence that included all four of the following treatments, separated by a washout period:

Treatment A: SYM-1219 oral microgranules containing 2 grams of secnidazole (therapeutic dose)

Treatment B: SYM-1219 oral microgranules containing 6 grams of secnidazole (supratherapeutic dose)

Treatment C: Placebo, matching SYM-1219, oral microgranules

Treatment D: Moxifloxacin, 400 mg, oral

Blood samples for PK analysis were collected within 30 minutes prior to dosing, and 1 hour, 2 hours, 3 hours, 4 hours, 5 hours, 6 hours, 8 hours, 12 hours, and 24 hours post-dose. A total of 50 subjects (29 males and 21 females) were included in the PK population. Noncompartmental PK parameters for these subjects are summarized by gender in Table 15 below.

TABLE 15

Summary of Secnidazole Pharmacokinetic Parameters by Treatment and Gender (TQT Study)

| Parameter | SYM-1219 2 grams | | SYM-1219 6 grams | |
|---|---|---|---|---|
| | Males (N = 29) | Females (N = 20) | Males (N = 28) | Females (N = 21) |
| $C_{max}$ (µg/mL) | | | | |
| n | 29 | 20 | 28 | 21 |
| Mean (SD) | 32.16 (5.856) | 47.29 (8.871) | 94.53 (13.227) | 137.81 (22.236) |
| % CV | 18.21 | 18.65 | 13.99 | 16.14 |
| Geometric Mean (SD) | 31.63 (5.902) | 46.56 (8.352) | 93.64 (13.099) | 136.23 (20.926) |
| $T_{max}$ (h) | | | | |
| n | 29 | 20 | 28 | 21 |
| Median | 4.130 | 4.130 | 5.120 | 4.130 |
| Min, Max | 3.12, 2.43 | 4.13, 6.12 | 3.12, 8.13 | 1.12, 6.12 |
| $AUC_{0-24}$ (hu*µg/mL) | | | | |
| n | 29 | 20 | 28 | 21 |
| Mean (SD) | 517.11 (9.237) | 757.76 (80.313) | 1672.08 (218.434) | 296.73 (256.139) |
| % CV | 18.29 | 10.60 | 13.06 | 10.69 |
| Geometric Mean (SD) | 528.63 (95.749) | 753.53 (82.913) | 1657.41 (228.632) | 2383.13 (263.488) |

CV = coefficient of variation;

SD = standard deviation;

n or N = number of subjects

Overall, SYM-1219 did not have a clinically meaningful effect on cardiac conduction (i.e., the PR and QRS intervals). SYM-1219 did not have a clinically relevant effect on heart rate or cardiac conduction (PR and QRS intervals). Both the QTc analysis and PK/QTc analysis demonstrate that SYM-1219 does not have aclinically relevant effect on the QTc interval and correspond to a negative TQT study, as defined by the ICH E14 guidance. There were no clinically meaningful trends noted in vital sign measurements or safety electrocardiogram data.

Here, plasma concentrations increased from 2 grams to 6 grams of secnidazole and were essentially dose-proportional; the variability in plasma concentrations was approximately 21% to 57% across the sampling times in this study; and the observed secnidazole plasma concentrations and exposures in males appeared to be slightly lower than those observed in females.

All of the TEAEs were reported as being mild or moderate in severity. No severe TEAEs or SAEs were reported. No deaths were reported in the study. One subject discontinued due to a non-treatment-related TEAE (atrial fibrillation) after administration of SYM-1219, 2 grams of secnidazole. The overall incidence rate of TEAEs was higher after administration of SYM-1219 (24.0% and 20.0% for 6 grams and 2 grams treatments, respectively) compared to the controls (8.3% and 4.3% for the placebo and Moxifloxacin treatments, respectively). The most frequently reported events included: headache, dizziness, and nausea.

Regardless of whether the comparison is based on the mean concentration-by-time data from the Phase I study discussed above or mean PK parameters from the TQT study discussed above, secnidazole exposure over the 24-hour sampling period appears to be approximately 1.5-fold lower (range 1.0-fold to 1.6-fold) in male subjects as compared to female subjects. However, it is clear that concentrations sufficient for efficacy (i.e., that exceed the median MLC of 1.6 µg/mL as discussed in the "Example 3—Microbiology—Susceptibility Testing" section above) are maintained over this time period in men suggesting that this difference is not clinically meaningful. Additionally, SYM-1219 safety in male is comparable to that achieved in female patients, and that SYM-1219 efficacy in the male population is at least more than 90% cure rate.

Further, as shown in Table 16 below, there is no remarkable difference in the exposure parameters ($C_{max}$ and AUC) between males and females with respect to SYM-1219 oral microgranules. Thus, the PK data suggests no clinically meaningful difference in systemic exposure to secnidazole between men and women, and indicate that secnidazole levels are maintained above the MLC for *T. vaginalis* for a sufficient duration of time post dose. Thus, SYM-1219 can be administered to both females and their respective male sexual partners to decrease transmission of trichomonasis.

TABLE 16

Overview of Plasma PK Data of SYM 1219 After a Single Oral Dose Administered to Fasted Healthy Males and Females

| | | PK Parameters | | | | | Exposure Parameters Dose-Adjusted to 1 gram (Mean) | | |
|---|---|---|---|---|---|---|---|---|---|
| | | $C_{max}$ (μg/mL) | $T_{max}$ (hr) | $AUC_{0\text{-}24}$ | $AUC_{0\text{-}\infty}$ | $T_{1/2}$ (hr) | | | |
| Formulation (Dose) | Population | Mean (SD) | Median (Min-Max) | (μg·hr/mL) Mean (SD) | (μg·hr/mL) Mean (SD) | Mean (SD) | $C_{max}$ (μg/mL) | $AUC_{0\text{-}24}$ (μg·hr/mL) | $AUC_{0\text{-}\infty}$ (μg·hr/mL) |
| Female | | | | | | | | | |
| SYM-1219, oral microgranules (secnidazole, 1 gram, single dose) | 14 HV[e] | 22.62 (2.871) | 3.0[b] (2.0-6.0)[b] | NR | 618.89 (98.093) | 17.05 (1.611) | 22.6 | NR | 618.9 |
| SYM-1219, oral microgranules (secnidazole, 2 grams, single dose) | 14 HV[e] | 45.43 (7.642) | 4.0[b] (3.0-4.0) | NR | 1331.6 (230.2) | 16.86 (2.649) | 22.7 | NR | 665.8 |
| SYM-1219, oral microgranules (secnidazole, 2 grams, single dose) | 20 HV[a,d] (for secnidazole 2 grams group) | 47.29 (8.821) | 4.130[b] (4.13-6.12)[b] | 757.76 (80.313) | NR | NR | 23.7 | 378.9 | NR |
| SYM-1219, oral microgranules (secnidazole, 6 grams, single dose) | 21 HV[a,d] (for secnidazole 6 grams group) | 137.81 (22.236) | 4.130[b] (3.12-6.12)[b] | 2396.73 (256.139) | NR | NR | 23.0 | 399.5 | NR |
| Male | | | | | | | | | |
| SYM-1219, oral microgranules (secnidazole, 2 grams, single dose) | 29 HV[a,d] | 32.16 (5.856) | 4.130[b] (3.12-24.13) | 537.11 (98.237) | NR | NR | 16.1 | 268.6 | NR |
| SYM-1219, oral microgranules (secnidazole, 6 grams, single dose) | | 94.53 (13.227) | 5.120[b] (3.12-8.13) | 1672.08 (218.434) | NR | NR | 15.8 | 278.7 | NR |

HV = healthy volunteers;
NR = not reported;
SD = standard deviation
[a] = Crossover study.
[b] = Median (range).
[c] = Mean (range).
[d] = From TQT study discussed above.
[e] = See Example 1 & Table 3 above.

Example 6—High Drug Loading Formulations

The methods and uses described herein also involve a pharmaceutical composition comprising a plurality of microgranules containing secnidazole as shown in Table 17 below. The experimental microgranule composition described in Table 17 allow for increased drug loading (70%) versus drug loading a conventional secnidazole-coated sugar sphere formulation (about 49%) described in Table 18 below. The ability to increase drug loading of the microgranules for use in the methods and uses described herein enables a therapeutic dose of a nitroimidazole compound, for example, 2 grams of secnidazole, to be administered in a composition with a substantially reduced mass (about 3,315 mg) compared with the mass of a secnidazole-coated sugar sphere formulation (about 4,600 mg) while maintaining substantially the same PK profile upon administration of a 2-gram dose to a subject. In some embodiments, a 2-gram dose as in Table 17 can be incorporated into a 4 size "00" capsule compared with 6 size "00" capsules for the secnidazole-coated sugar sphere formulation of Table 18. In some embodiments, drug loading of the microgranules may exceed 70%, such as, for example, 90% drug loading in which case, a 2-gram dose of secnidazole may be incorporated into about 4 size "0EL" capsules.

TABLE 17

Experimental High Drug Loading Formulation

| Material | mg/dose | % w/w |
|---|---|---|
| Drug Core | | |
| Secnidazole | 2000.00 | 60.33 (70.00% of core) |
| Avicel ® PH-101 | 757.00 | 22.84 (26.50% of core) |
| Methocel ™ AV15LV | 100.00 | 3.02 (3.50% of core) |
| Finish Coating | | |
| Eudragit ® NE30D | 192.00 | 5.79 |
| PEG 4000 | 58.00 | 1.75 |
| Talc USP | 192.00 | 5.79 |
| Blending | | |
| Talc USP | 16.00 | 0.48 |
| Total Weight | 3315.00 | 100.00 |

In some embodiments, the pharmaceutical compositions described herein comprise the secnidazole microgranules may exhibit a similar PK profile as a secnidazole-coated sugar sphere formulated as shown in Table 18 below.

TABLE 18

Coated Secnidazole-Coated Sugar Sphere Formulation

| Material | mg/dose | % w/w |
|---|---|---|
| Secnidazole | 2000.00 | 43.48 |
| Sugar Spheres (size 40-50 mesh) | 2000.00 | 43.48 |
| Povidone (Plasdone ™ K-29/32) | 81.63 | 1.77 |
| Polyethylene Glycol 4000 | 83.3 | 1.81 |
| Ethyl Acrylate-Methyl Methacrylate Copolymer (Eudragit ® NE30D) | 277.6621 | 6.04 |
| Talc | 138.831 | 3.02 |
| Collodial Silicon Dioxide (Aerosil ® 200) | 18.577 | 0.4 |
| Total | 4600.00 | 100 |

In some embodiments, the pharmaceutical compositions described herein may have a PK profile comparable to the profiles shown in the "SYM-1219, 2 grams (N=14)" column in Tables 2 & 3, which display the PK profiles of the composition of Table 9. More specifically, the "SYM-1219, 2 grams (N=14)" column of Table 2 shows the expected plasma PK of 2-gram secnidazole microgranule formulation (70% drug in microgranule core) after a single oral dose administered to fasted healthy female subjects, and the "SYM-1219, 2 grams (N=14)" column of Table 4 shows the expected urine PK of 2-gram secnidazole microgranule formulation (70% drug in microgranule core) after a single oral dose administered to fasted healthy female subjects.

Specific modes of administration of the pharmaceutical compositions described herein depends on the indication. The selection of the specific route of administration and the dose regimen may be adjusted or titrated by the clinician according to methods known to the clinician to obtain the optimal clinical response. The amount of nitroimidazole compound, such as secnidazole, may be that amount that is therapeutically effective. The dosage to be administered may depend on the characteristics of the subject being treated, e.g., the particular animal or human subject treated, age, weight, body mass index, body surface area, health, types of concurrent treatment, if any, and frequency of treatments, and can be determined by one of skill in the art (e.g., by the clinician).

In the embodiments described herein, the therapeutically effective amount of a nitroimidazole compound may be administered in a pharmaceutical composition. Each of the pharmaceutical compositions described herein may be used in any of the methods or dosage regimens described herein.

In some embodiments, administering a therapeutically effective amount of a nitroimidazole compound may include administering a nitroimidazole compound or a pharmaceutically acceptable salt thereof in a controlled release form. In some embodiments, the coating described herein may delay disintegration and absorption in the gastrointestinal tract and thereby providing a controlled and/or sustained action over a longer period than an immediate release composition. Additionally, such coatings may be adapted for release of a nitroimidazole compound in a predetermined pattern (e.g., in order to achieve a controlled release composition) or it may be adapted not to release the active compound until after passage of the stomach (enteric coating). Suitable coatings encompassed by such embodiments may include, but not limited to, sugar coating, film coating (e.g., hydroxypropyl methylcellulose, methylcellulose, methyl hydroxyethyl cellulose, hydroxypropyl cellulose, carboxymethylcellulose, acrylate copolymers, polyethylene glycols and/or polyvinylpyrrolidone), or an enteric coating (e.g., methacrylic acid copolymer, cellulose acetate phthalate, hydroxypropylmethylcellulose phthalate, hydroxypropyl methylcellulose acetate succinate, polyvinyl acetate phthalate, shellac, and/or ethyl cellulose). Furthermore, a time delay material such as, for example, glyceryl monostearate or glyceryl distearate may be incorporated into the coatings of some embodiments. In still other embodiments, the coating may be adapted to protect the composition from unwanted chemical changes, for example, to reduce chemical degradation prior to the release of the active drug substance.

It is also known in the art that the active ingredients may be contained in such compositions with pharmaceutically acceptable diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, G. S. Banker & C. T. Rhodes, $4^{th}$ Edition, CRC Press (2002); *Goodman & Gilman's The Pharmaceutical Basis of Therapeutics*, L. L. Brunton, R. Hilal-Dandan & B. C. Knollmann, 13th Edition, McGraw-Hill Education (2018); *Remington's Pharmaceutical Sciences* by E. W. Martin; and *Remington: The Science and Practice of Pharmacy*, Loyd V. Allen (Ed.), $22^{nd}$ Edition, Pharmaceutical Press (2013) can be consulted.

Examples of Experimental High Drug Loading Cores

Experimental drug cores of Table 19 below were prepared by the following process:
1. Wet granulation: In a planetary mixer or high shear granulator, water is sprayed on a mixture of secnidazole, the product cellulose microcrystalline sold under the trademark Avicel® PH-101 and the product methyl cellulose sold under the trademark Methocel® A15LV until the Methocel® is completely hydrated.
2. Extrusion: The granulation is passed through a Niro Extruder fitted with a 0.8 mm screen.
3. Spheronization: The extrudates are spheronized using a Niro Spheronizer.
4. Drying and Screening: The spheres are dried in a Glatt fluid bed and screened to remove fines and oversize material.

5. Wurster coating: A PEG 4000, Eudragit NE30D and talc dispersion is sprayed on the spheres using a Glatt fluid bed.
6. Drying and Screening: The coated spheres are dried in a Glatt fluid bed and screened to remove fines and oversize material.
7. Blending and Curing: The coated spheres are blended with talc in a V-blender and cured in a tray dryer at 40° C. for 24 hours.

TABLE 19

Experimental High Drug Loading Core Specification and Characteristics

| Batch # | 21155-01-39A | 21155-01-39B | 21155-01-39C |
|---|---|---|---|
| Drug Load (Core) | 90% | 82% | 70% |
| Avicel ® Level | 8% | 14.6% | 26.5% |
| Binder Level | 2% | 3.55% | 3.5% |
| Water Quantity | 30% | 30% | 45% |
| Yield After Drying (g) | 335 | 572 | 555 |
| Fines (30 mesh) | 77.5 grams (23%) | 53 grams (11%) | 77 grams (13.9%) |
| Retentions (16 mesh) | 2 grams (0.6%) | 30 grams (5.2%) | 15 grams (2.7%) |
| Acceptable Pellets | 253 grams | 486 grams | 460 grams |

Experimental high drug loading cores were coated with a PEG 4000, Eudragit® NE30D and talc dispersion. Samples were pulled after 5.1%, 6.7% and 7.9% polymer weight gain, cured at 40° C. for 24 hours and tested for dissolution. The results are shown in Table 20 below, with f2 values calculated relative to the profile of a drug-coated sugar sphere coated with a PEG 4000, Eudragit® NE30D and talc dispersion (control core). The 6.7% coating is closest to the clinical batch and has an acceptable f2 value.

TABLE 20

Dissolution Characteristics of Experimental High Drug Loading Cores with Different Coating Weight Gain

| Time (mins) | Control Core | 5.1% Coat | 6.7% Coat | 7.9% Coat |
|---|---|---|---|---|
| | % dissolved in pH 6.8 phosphate buffer USP 1, 50 rpm | | | |
| 30 | 20 | 24 | 13 | 9 |
| 60 | 38 | 55 | 37 | 27 |
| 90 | 57 | 81 | 62 | 47 |
| 120 | 72 | 93 | 79 | 64 |
| 150 | 84 | 98 | 90 | 78 |
| 180 | 92 | 99 | 96 | 87 |
| f2 | | 39 | 63 | 52 |

The invention described and claimed herein have many attributes and embodiments including, but not limited to, those set forth or described or referenced in this Detailed Disclosure of the Invention. It is not intended to be all-inclusive and the invention described and claimed herein are not limited to or by the features or embodiments identified in this Detailed Disclosure of the Invention, which is included for purposes of illustration only and not restriction. A person having ordinary skill in the art will readily recognize that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, and in embodiments or examples of the invention, any of the terms "comprising," "consisting essentially of," and "consisting of" may be replaced with either of the other two terms in the specification. The methods and processes illustratively described herein suitably may be practiced in differing orders of steps, and that they are not necessarily restricted to the orders of steps indicated herein or in the claims. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicant. Furthermore, titles, headings, or the like are provided to enhance the reader's comprehension of this document, and should not be read as limiting the scope of the invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method of treating trichomoniasis in a human in need thereof comprising orally administering to the human a microgranule formulation comprising a therapeutically effective amount of secnidazole or a pharmaceutically acceptable salt thereof that exhibits a maximum plasma concentration (Cmax) of 29.15 μg/ml to 31.05 μg/ml and a time to maximum plasma concentration ($T_{max}$) of 6.6 hours to 24 hours in the human, wherein the microgranule formulation comprises a plurality of microgranules, each microgranule comprises secnidazole and has a particle diameter in the range of 400 micrometers to 841 micrometers, wherein secnidazole or the pharmaceutically acceptable salt thereof is the sole drug in the microgranule formulation.

2. The method of claim 1, wherein the therapeutically effective amount of secnidazole or a pharmaceutically acceptable salt thereof is a total daily dose of 2 grams, 4 grams or 6 grams of secnidazole or a pharmaceutically acceptable salt thereof in a microgranule formulation for a period of 1 day to 14 days.

3. The method of claim 1, wherein the human in need thereof is a sexual partner to a person with trichomoniasis, and the therapeutically effective amount of secnidazole or a pharmaceutically acceptable salt thereof is a total daily dose of 2 grams, 4 grams or 6 grams of secnidazole or a pharmaceutically acceptable salt thereof in a microgranule formulation.

4. The method of claim 1, wherein the microgranule formulation is a taste-masked microgranule formulation.

5. The method of claim 1, wherein each microgranule comprises a sugar core or a microcrystalline cellulose core, and a layer outside of the sugar core or the microcrystalline cellulose core, the layer comprising secnidazole or the pharmaceutically acceptable salt thereof.

6. The method of claim 1, wherein the microgranule formulation further comprises at least one compound selected from the group consisting of sugar spheres, povidone, polyethylene glycol with an average molecular weight of 4000 g/mol, ethyl acrylatemethyl methacrylate copolymer and, talc, or a combination thereof.

7. The method of claim 1, wherein the microgranule formulation is integrated with a food substance prior to administration to the human.

8. The method of claim 7, wherein the food substance is a liquid, semisolid or a soft food.

9. The method of claim 7, wherein the food substance is applesauce, yogurt, or pudding.

10. The method of claim 7, wherein the integration is mixing the microgranule formulation into the food substance.

11. The method of claim 1, wherein the human is a female.

12. The method of claim 1, wherein the human is an adult or child.

13. The method of claim 11, wherein the human is a pregnant female.

14. The method of claim 1, wherein the human is a female who is also suffering from bacterial vaginosis.

15. The method of claim 1, wherein the human is a HIV-positive male or HIV-positive female.

16. The method of claim 1, wherein the human is a HIV-positive female who is also suffering from bacterial vaginosis.

17. The method of claim 1, wherein the human is infected with metronidazole-resistant trichomoniasis or tinidazole-resistant trichomoniasis.

18. The method of claim 1, wherein the human is also HIV-positive, suffering from bacterial vaginosis or a combination thereof.

19. The method of claim 1, wherein the microgranule formulation is administered as a single dose.

20. The method of claim 1, wherein the microgranule formulation is administered with an additional compound selected from ethinyl estradiol (EE2), norethindrone (NET), or a combination thereof.

21. The method of claim 1, wherein the microgranule formulation is administered with paromomycin, tinidazole, metronidazole, boric acid or a combination thereof.

22. The method of claim 20, wherein the additional compound is administered on the same day as the microgranule formulation.

23. The method of claim 20, wherein the additional compound is administered on a different day as the microgranule formulation.

24. The method of claim 1, wherein the microgranule formulation is administered as a single dose and is the only dose required to be administered to the human to achieve a post-treatment clinical outcome by resolution of one or more symptoms of trichomoniasis.

25. The method of claim 1, wherein the therapeutically effective amount of secnidazole or the pharmaceutically acceptable salt thereof is 2 grams.

26. The method of claim 1, wherein the microgranule formulation does not affect the contraceptive efficacy of an additional compound selected from ethinyl estradiol (EE2), norethindrone (NET) or a combination thereof.

27. A method of treating trichomoniasis in a human in need thereof comprising orally administering to the human a therapeutically effective amount of secnidazole or a pharmaceutically acceptable salt thereof in a microgranule formulation, wherein the microgranule formulation comprises a plurality of microgranules, wherein the therapeutically effective amount of secnidazole or the pharmaceutically acceptable salt thereof is an amount of secnidazole or the pharmaceutically acceptable salt thereof that exhibits a maximum plasma concentration ($C_{max}$) of 29.15 μg/ml to 31.05 μg/ml and a time to maximum plasma concentration ($T_{max}$) of 6.6 hours to 24 hours in the human, and wherein secnidazole or the pharmaceutically acceptable salt thereof is the sole drug in the microgranule formulation, wherein the plurality of microgranules has a volume-weighted particle size distribution within a microgranule population, and wherein the volume-weighted particle size distribution as measured by mean diameter using laser diffraction from a representative sample of the microgranule population comprises at least 10% of the microgranule population having a volume-weighted particle size equal to or greater than 470 micrometers.

28. A method of treating trichomoniasis in a human in need thereof, comprising orally administering to the human a therapeutically effective amount of secnidazole or a pharmaceutically acceptable salt thereof in a microgranule formulation, wherein the microgranule formulation comprises a plurality of microgranules, wherein the therapeutically effective amount of secnidazole or the pharmaceutically acceptable salt thereof is an amount of secnidazole or the pharmaceutically acceptable salt thereof that exhibits a maximum plasma concentration ($C_{max}$) of about 29.15 µg/ml to about 31.05 µg/ml and a time to maximum plasma concentration ($T_{max}$) of 6.6 hours to 24 hours in the human, and wherein secnidazole or the pharmaceutically acceptable salt thereof is the sole drug in the microgranule formulation,
  wherein the plurality of microgranules has a volume-weighted particle size distribution within a microgranule population, and
  wherein the volume-weighted particle size distribution as measured by mean diameter using laser diffraction from a representative sample of the microgranule population further comprises 50% of the microgranule population having a volume-weighted particle size between about 640 micrometers and about 810 micrometers.

29. A method of treating trichomoniasis in a human in need thereof, comprising orally administering to the human a therapeutically effective amount of secnidazole or a pharmaceutically acceptable salt thereof in a microgranule formulation, wherein the microgranule formulation comprises a plurality of microgranules, wherein the therapeutically effective amount of secnidazole or the pharmaceutically acceptable salt thereof is an amount of secnidazole or the pharmaceutically acceptable salt thereof that exhibits a maximum plasma concentration ($C_{max}$) of about 29.15 µg/ml to about 31.05 µg/ml and a time to maximum plasma concentration (T max) of 6.6 hours to 24 hours in the human, and wherein secnidazole or the pharmaceutically acceptable salt thereof is the sole drug in the microgranule formulation,
  wherein the plurality of microgranules has a volume-weighted particle size distribution within a microgranule population, and
  wherein the volume-weighted particle size distribution as measured by mean diameter using laser diffraction from a representative sample of the microgranule population further comprises 90% of the microgranule population having a volume-weighted particle size about no more than 1170 micrometers.

* * * * *